US009885086B2

(12) United States Patent
Byrd et al.

(10) Patent No.: US 9,885,086 B2
(45) Date of Patent: Feb. 6, 2018

(54) PHOSPHOLIPASE C GAMMA 2 AND RESISTANCE ASSOCIATED MUTATIONS

(71) Applicant: Pharmacyclics LLC, Sunnyvale, CA (US)

(72) Inventors: John C. Byrd, Columbus, OH (US); Jennifer A. Woyach, Columbus, OH (US)

(73) Assignee: Pharmacyclics LLC, Sunnyvale, CA (US)

( * ) Notice: Subject to any disclaimer, the term of this patent is extended or adjusted under 35 U.S.C. 154(b) by 76 days.

(21) Appl. No.: 14/664,663

(22) Filed: Mar. 20, 2015

(65) Prior Publication Data

US 2015/0267261 A1    Sep. 24, 2015

Related U.S. Application Data

(60) Provisional application No. 61/968,315, filed on Mar. 20, 2014, provisional application No. 62/002,743, filed on May 23, 2014.

(51) Int. Cl.
*C12Q 1/68* (2006.01)
*G01N 33/574* (2006.01)
*A61K 31/519* (2006.01)

(52) U.S. Cl.
CPC .......... *C12Q 1/6886* (2013.01); *A61K 31/519* (2013.01); *G01N 33/57426* (2013.01); *C12Q 2600/106* (2013.01); *C12Q 2600/156* (2013.01); *G01N 2333/916* (2013.01); *G01N 2800/52* (2013.01)

(58) Field of Classification Search
None
See application file for complete search history.

(56) References Cited

U.S. PATENT DOCUMENTS

| | | |
|---|---|---|
| 3,547,119 A | 12/1970 | Farb |
| 4,311,137 A | 1/1982 | Gerard |
| 4,360,019 A | 11/1982 | Portner et al. |
| 4,487,603 A | 12/1984 | Harris |
| 4,531,937 A | 7/1985 | Yates |
| 4,683,202 A | 7/1987 | Mullis |
| 4,692,147 A | 9/1987 | Duggan |
| 4,725,852 A | 2/1988 | Gamblin et al. |
| 4,755,173 A | 7/1988 | Konopka et al. |
| 4,843,155 A | 6/1989 | Chomczynski |
| 5,033,252 A | 7/1991 | Carter |
| 5,052,558 A | 10/1991 | Carter |
| 5,323,907 A | 6/1994 | Kalvelage |
| 5,384,261 A | 1/1995 | Winkler et al. |
| 5,397,787 A | 3/1995 | Buzzetti et al. |
| 5,445,934 A | 8/1995 | Fodor et al. |
| 5,593,997 A | 1/1997 | Dow et al. |
| 5,643,207 A | 7/1997 | Rise |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,807,876 A | 9/1998 | Armistead et al. |
| 5,820,589 A | 10/1998 | Torgerson et al. |
| 5,854,033 A | 12/1998 | Lizardi |
| 5,856,174 A | 1/1999 | Lipshutz et al. |
| 5,874,219 A | 2/1999 | Rava et al. |
| 5,922,591 A | 7/1999 | Anderson et al. |
| 6,001,839 A | 12/1999 | Calderwood et al. |
| 6,017,328 A | 1/2000 | Fischell et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 6,054,472 A | 4/2000 | Armistead et al. |
| 6,160,010 A | 12/2000 | Uckun et al. |
| 6,198,966 B1 | 3/2001 | Heruth |
| 6,221,900 B1 | 4/2001 | Uckun et al. |

(Continued)

FOREIGN PATENT DOCUMENTS

| CA | 2663116 A1 | 4/2008 |
|---|---|---|
| CA | 2847852 A1 | 4/2008 |

(Continued)

OTHER PUBLICATIONS

ClinicalTrials.gov archive (NCT01105247 on Apr. 15, 2010).*
Maddock et al (JAMA Oncology, 2015, vol. 1, pp. 80-87).*
Woyach et al (Leukemia, 2012, vol. 26, pp. 1442-1444).*
ACS 2015 (http://www.cancer.org/cancer/non-hodgkinlymphoma/detailedguide/non-hodgkin-lymphoma-types-of-non-hodgkinlymphoma).
Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).
Advani, R.H., et al., 2013, "Bruton tyrosine kinase inhibitor Ibrutinib (PCI-32765) ha significant activity in patients with relapsed/refractory B-cell malignancies", Journal of Clinical Oncology, vol. 21, No. 1 ,pp. 88-94.

(Continued)

*Primary Examiner* — Karen Canella
(74) *Attorney, Agent, or Firm* — Foley Hoag LLP

(57) ABSTRACT

Described herein is a mutation that confers resistance to the treatment with a BTK inhibitor. Described herein is a modified PLCγ2 polypeptide that is modified at amino acid position 742, 845, or 1140 and the modified PLCγ2 polypeptide exhibits decreased inhibition (e.g., resistance) to a covalent and/or irreversible BTK inhibitor. Described herein are diagnostic methods for detecting the modified polypeptide and nucleic acid encoding the modified polypeptide and applications of the methods thereof. Described herein are compositions, combinations, and kits containing the modified polypeptide and methods of using the modified polypeptide. Also described herein are methods of using the modified polypeptide as screening agents for the identification and design of inhibitors of PLCγ2.

56 Claims, 13 Drawing Sheets

(56) References Cited

U.S. PATENT DOCUMENTS

| | | |
|---|---|---|
| 6,306,897 B1 | 10/2001 | Uckun et al. |
| 6,326,469 B1 | 12/2001 | Ullrich et al. |
| 6,344,316 B1 | 2/2002 | Lockhart et al. |
| 6,344,465 B1 | 2/2002 | Armistead et al. |
| 6,498,178 B2 | 12/2002 | Stamos et al. |
| 6,506,769 B2 | 1/2003 | Snow et al. |
| 6,660,744 B1 | 12/2003 | Hirst et al. |
| 6,673,333 B1 | 1/2004 | Meade et al. |
| 6,753,348 B2 | 6/2004 | Uckun et al. |
| 6,770,639 B2 | 8/2004 | Snow et al. |
| 6,824,768 B2 | 11/2004 | Stalgis et al. |
| 6,893,638 B2 | 5/2005 | Anderson et al. |
| 6,921,763 B2 | 7/2005 | Hirst et al. |
| 6,950,493 B2 | 9/2005 | Besson |
| 7,083,784 B2 | 8/2006 | Dall'Acqua et al. |
| 7,116,749 B2 | 10/2006 | Besson |
| 7,138,420 B2 | 11/2006 | Bentzien et al. |
| 7,332,497 B2 | 2/2008 | Hirst et al. |
| 7,514,444 B2 | 4/2009 | Honigberg et al. |
| 7,547,689 B2 | 6/2009 | Sessler et al. |
| 7,599,542 B2 | 10/2009 | Brockway et al. |
| 7,700,075 B2 | 4/2010 | Weichert et al. |
| 7,718,662 B1 | 5/2010 | Chen et al. |
| 7,732,454 B2 | 6/2010 | Honigberg et al. |
| 7,741,330 B1 | 6/2010 | Chen et al. |
| 7,825,118 B2 | 11/2010 | Honigberg et al. |
| 7,960,396 B2 | 6/2011 | Honigberg et al. |
| 8,008,309 B2 | 8/2011 | Honigberg et al. |
| 8,058,249 B2 | 11/2011 | Krieg et al. |
| 8,088,781 B2 | 1/2012 | Honigberg et al. |
| 8,158,786 B2 | 4/2012 | Honigberg et al. |
| 8,232,280 B2 | 7/2012 | Honigberg et al. |
| 8,236,812 B2 | 8/2012 | Honigberg et al. |
| 8,306,897 B2 | 11/2012 | Yolles |
| 8,377,946 B1 | 2/2013 | Chen et al. |
| 8,399,470 B2 | 3/2013 | Honigberg et al. |
| 8,476,284 B2 | 7/2013 | Honigberg et al. |
| 8,497,277 B2 | 7/2013 | Honigberg et al. |
| 8,501,724 B1 | 8/2013 | Chen et al. |
| 8,501,751 B2 | 8/2013 | Honigberg et al. |
| 8,552,010 B2 | 10/2013 | Honigberg et al. |
| 8,557,803 B2 | 10/2013 | Yamamoto et al. |
| 8,563,563 B2 | 10/2013 | Honigberg et al. |
| 8,568,653 B2 | 10/2013 | Thillen et al. |
| 8,633,311 B2 | 1/2014 | Prestwich et al. |
| 8,642,604 B2 | 2/2014 | Knight et al. |
| 8,658,653 B2 | 2/2014 | Honigberg et al. |
| 8,691,546 B2 | 4/2014 | Honigberg et al. |
| 8,697,711 B2 | 4/2014 | Honigberg et al. |
| 8,703,780 B2 | 4/2014 | Honigberg et al. |
| 8,735,403 B2 | 5/2014 | Honigberg et al. |
| 8,735,404 B2 | 5/2014 | Honigberg et al. |
| 8,741,908 B2 | 6/2014 | Honigberg et al. |
| 8,748,438 B2 | 6/2014 | Honigberg et al. |
| 8,748,439 B2 | 6/2014 | Honigberg et al. |
| 8,754,090 B2 | 6/2014 | Buggy et al. |
| 8,754,091 B2 | 6/2014 | Honigberg et al. |
| 8,759,516 B2 | 6/2014 | Honigberg et al. |
| 8,809,273 B2 | 8/2014 | Honigberg et al. |
| 8,883,435 B2 | 11/2014 | Honigberg et al. |
| 8,883,803 B2 | 11/2014 | Honigberg et al. |
| 8,940,750 B2 | 1/2015 | Honigberg et al. |
| 8,952,015 B2 | 2/2015 | Honigberg et al. |
| 8,957,079 B2 | 2/2015 | Honigberg et al. |
| 8,975,266 B2 | 3/2015 | Honigberg et al. |
| 8,987,233 B2 | 3/2015 | Pan et al. |
| 8,999,999 B2 | 4/2015 | Buggy et al. |
| 9,012,463 B2 | 4/2015 | Chen et al. |
| 9,079,908 B2 | 7/2015 | Honigberg et al. |
| 9,107,924 B2 | 8/2015 | Buggy et al. |
| 9,117,924 B2 | 8/2015 | Kitagawa et al. |
| 9,125,889 B2 | 9/2015 | Buggy |
| 9,127,012 B2 | 9/2015 | Honigberg et al. |
| 9,133,198 B2 | 9/2015 | Honigberg et al. |
| 9,133,201 B2 | 9/2015 | Honigberg et al. |
| 9,133,202 B2 | 9/2015 | Honigberg et al. |
| 9,139,591 B2 | 9/2015 | Honigberg et al. |
| 9,181,257 B2 | 11/2015 | Honigberg et al. |
| 9,181,263 B2 | 11/2015 | Honigberg et al. |
| 9,193,735 B2 | 11/2015 | Honigberg et al. |
| 9,206,189 B2 | 12/2015 | Honigberg et al. |
| 9,212,185 B2 | 12/2015 | Honigberg et al. |
| 9,266,893 B2 | 2/2016 | Honigberg et al. |
| 9,273,051 B2 | 3/2016 | Chen et al. |
| 9,278,100 B2 | 3/2016 | Honigberg et al. |
| 9,296,753 B2 | 3/2016 | Smyth et al. |
| 9,409,911 B2 | 8/2016 | Honigberg et al. |
| 9,415,050 B2 | 8/2016 | Chen et al. |
| 9,540,382 B2 | 1/2017 | Purro et al. |
| 9,540,385 B2 | 1/2017 | Chen et al. |
| 9,556,182 B2 | 1/2017 | Honigberg et al. |
| 2002/0004584 A1 | 1/2002 | Laughlin |
| 2002/0016460 A1 | 2/2002 | Snow et al. |
| 2002/0127203 A1 | 9/2002 | Albrecht |
| 2002/0155505 A1 | 10/2002 | Wells et al. |
| 2003/0013118 A1 | 1/2003 | Edge et al. |
| 2003/0013125 A1 | 1/2003 | Braisted et al. |
| 2003/0035833 A1 | 2/2003 | He |
| 2003/0040461 A1 | 2/2003 | McAtee |
| 2003/0103938 A1 | 6/2003 | Jinquan et al. |
| 2003/0125235 A1 | 7/2003 | Foxwell |
| 2004/0006083 A1 | 1/2004 | Hirst et al. |
| 2004/0136954 A1 | 7/2004 | Grusby et al. |
| 2004/0241651 A1* | 12/2004 | Olek .................. C07K 14/4703 435/6.16 |
| 2004/0264627 A1 | 12/2004 | Besson |
| 2005/0008640 A1 | 1/2005 | Waegell et al. |
| 2005/0064464 A1 | 3/2005 | Punnonen et al. |
| 2005/0084905 A1 | 4/2005 | Prescott et al. |
| 2005/0090499 A1 | 4/2005 | Currie et al. |
| 2005/0101604 A1 | 5/2005 | Currie et al. |
| 2005/0196851 A1 | 9/2005 | Uckun |
| 2005/0209255 A1 | 9/2005 | Jimenez et al. |
| 2005/0220265 A1 | 10/2005 | Besson |
| 2006/0079494 A1 | 4/2006 | Santi et al. |
| 2006/0167090 A1 | 7/2006 | Uckun et al. |
| 2006/0178367 A1 | 8/2006 | Currie et al. |
| 2006/0211112 A1 | 9/2006 | Harris et al. |
| 2006/0292181 A1 | 12/2006 | Brayden |
| 2007/0032457 A1 | 2/2007 | Blatt |
| 2007/0065449 A1 | 3/2007 | Verschraegen |
| 2007/0105136 A1 | 5/2007 | Staudt et al. |
| 2007/0122417 A1 | 5/2007 | Holt et al. |
| 2007/0281907 A1 | 12/2007 | Watkins |
| 2007/0293499 A1 | 12/2007 | Flynn et al. |
| 2008/0076921 A1 | 3/2008 | Honigberg et al. |
| 2008/0108636 A1 | 5/2008 | Honigberg et al. |
| 2008/0139582 A1 | 6/2008 | Honigberg et al. |
| 2008/0146555 A1 | 6/2008 | Caligiuri et al. |
| 2008/0153877 A1 | 6/2008 | Adimoolam et al. |
| 2008/0214501 A1 | 9/2008 | Pan et al. |
| 2009/0010911 A1 | 1/2009 | Andreotti et al. |
| 2009/0039734 A1 | 2/2009 | Takahashi et al. |
| 2009/0047353 A1 | 2/2009 | O'Hagan |
| 2009/0098137 A1 | 4/2009 | Burke et al. |
| 2009/0105209 A1 | 4/2009 | Dewdney et al. |
| 2009/0149389 A1 | 6/2009 | Panitch et al. |
| 2009/0181987 A1 | 7/2009 | Honigberg et al. |
| 2009/0186898 A1 | 7/2009 | Dewdney et al. |
| 2009/0197853 A1 | 8/2009 | Magda |
| 2009/0297551 A1 | 12/2009 | Sattentau et al. |
| 2009/0317836 A1 | 12/2009 | Kuhn et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0041677 A1 | 2/2010 | Honigberg et al. |
| 2010/0087482 A1 | 4/2010 | Haber et al. |
| 2010/0158866 A1 | 6/2010 | Zhu |
| 2010/0185419 A1 | 7/2010 | Singh et al. |
| 2010/0222325 A1 | 9/2010 | Berthel et al. |
| 2010/0254905 A1 | 10/2010 | Honigberg et al. |
| 2010/0266589 A1 | 10/2010 | Hedrick et al. |
| 2010/0324050 A1 | 12/2010 | Honigberg et al. |
| 2011/0039868 A1 | 2/2011 | Honigberg et al. |

(56) References Cited

U.S. PATENT DOCUMENTS

| | | |
|---|---|---|
| 2011/0059854 A1 | 3/2011 | Gordon et al. |
| 2011/0086866 A1 | 4/2011 | Chen et al. |
| 2011/0125628 A1 | 5/2011 | Marchegiani |
| 2011/0177011 A1 | 7/2011 | Currie et al. |
| 2011/0209230 A1 | 8/2011 | Korman et al. |
| 2011/0224235 A1 | 9/2011 | Honigberg et al. |
| 2011/0244465 A1 | 10/2011 | Harvey et al. |
| 2011/0281322 A1 | 11/2011 | Honigberg et al. |
| 2011/0281850 A1 | 11/2011 | Flynn et al. |
| 2011/0288032 A1 | 11/2011 | Ganji |
| 2011/0306599 A1 | 12/2011 | Inoue et al. |
| 2012/0039850 A1 | 2/2012 | McNair et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129853 A1 | 5/2012 | Elmore et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0178753 A1 | 7/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0214826 A1 | 8/2012 | Honigberg et al. |
| 2012/0219522 A1 | 8/2012 | Xi |
| 2012/0252821 A1 | 10/2012 | Honigberg et al. |
| 2012/0252822 A1 | 10/2012 | Honigberg et al. |
| 2012/0277225 A1 | 11/2012 | Honigberg et al. |
| 2012/0277254 A1 | 11/2012 | Honigberg et al. |
| 2012/0277255 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0329130 A1 | 12/2012 | Honigberg et al. |
| 2013/0005745 A1 | 1/2013 | Honigberg et al. |
| 2013/0005746 A1 | 1/2013 | Honigberg et al. |
| 2013/0012525 A1 | 1/2013 | Honigberg et al. |
| 2013/0018060 A1 | 1/2013 | Honigberg et al. |
| 2013/0029984 A1 | 1/2013 | Castro et al. |
| 2013/0035334 A1 | 2/2013 | Honigberg et al. |
| 2013/0041013 A1 | 2/2013 | Lavitrano et al. |
| 2013/0041014 A1 | 2/2013 | Lavitrano et al. |
| 2013/0079327 A1 | 3/2013 | Yamamoto et al. |
| 2013/0172314 A1 | 7/2013 | Chen et al. |
| 2013/0184223 A1 | 7/2013 | Land et al. |
| 2013/0184342 A1 | 7/2013 | Mills et al. |
| 2013/0195852 A1 | 8/2013 | Buggy et al. |
| 2013/0202611 A1 | 8/2013 | Buggy et al. |
| 2013/0217880 A1 | 8/2013 | Yamamoto et al. |
| 2013/0231328 A1 | 9/2013 | Harriman et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0016306 A1 | 1/2014 | de Blois |
| 2014/0018414 A1 | 1/2014 | Brosnan |
| 2014/0039186 A1 | 2/2014 | Honigberg et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0128413 A1 | 5/2014 | Honigberg et al. |
| 2014/0128414 A1 | 5/2014 | Honigberg et al. |
| 2014/0134265 A1 | 5/2014 | Buggy et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194417 A1 | 7/2014 | Greenwood et al. |
| 2014/0194446 A1 | 7/2014 | Buggy et al. |
| 2014/0206681 A1 | 7/2014 | Kim et al. |
| 2014/0212485 A1 | 7/2014 | Honigberg et al. |
| 2014/0243355 A1 | 8/2014 | Honigberg et al. |
| 2014/0249215 A1 | 9/2014 | Pimont-Garro et al. |
| 2014/0275125 A1 | 9/2014 | Honigberg et al. |
| 2014/0303191 A1 | 10/2014 | Buggy et al. |
| 2014/0336203 A1 | 11/2014 | Smyth et al. |
| 2014/0336206 A1 | 11/2014 | Honigberg et al. |
| 2014/0371241 A1 | 12/2014 | Buggy et al. |
| 2014/0377258 A1 | 12/2014 | Stern et al. |
| 2014/0378446 A1 | 12/2014 | Chen et al. |
| 2015/0018336 A1 | 1/2015 | Chen et al. |
| 2015/0031710 A1 | 1/2015 | Buggy et al. |
| 2015/0031711 A1 | 1/2015 | Buggy et al. |
| 2015/0038518 A1 | 2/2015 | Balasubramanian |
| 2015/0072988 A1 | 3/2015 | Carducci et al. |
| 2015/0105409 A1 | 4/2015 | Quayle et al. |
| 2015/0118222 A1 | 4/2015 | Levy et al. |
| 2015/0133661 A1 | 5/2015 | Honigberg et al. |
| 2015/0140036 A1 | 5/2015 | Mannick et al. |
| 2015/0152115 A1 | 6/2015 | Honigberg et al. |
| 2015/0158871 A1 | 6/2015 | Purro et al. |
| 2015/0184249 A1 | 7/2015 | Chang et al. |
| 2015/0210769 A1 | 7/2015 | Freeman et al. |
| 2015/0238490 A1 | 8/2015 | Burger |
| 2015/0239897 A1 | 8/2015 | Chen et al. |
| 2015/0265618 A1 | 9/2015 | Honigberg et al. |
| 2015/0267261 A1 | 9/2015 | Byrd et al. |
| 2015/0306103 A1 | 10/2015 | Honigberg et al. |
| 2015/0306106 A1 | 10/2015 | Honigberg et al. |
| 2015/0307500 A1 | 10/2015 | Honigberg et al. |
| 2016/0000792 A1 | 1/2016 | Buggy et al. |
| 2016/0009714 A1 | 1/2016 | Sun et al. |
| 2016/0159905 A1 | 6/2016 | Abdiche et al. |
| 2016/0175312 A1 | 6/2016 | Buggy et al. |
| 2016/0243033 A1 | 8/2016 | Buggy et al. |
| 2016/0324859 A1 | 11/2016 | Buggy et al. |
| 2017/0071962 A1 | 3/2017 | Lannutti et al. |

FOREIGN PATENT DOCUMENTS

| | | |
|---|---|---|
| CN | 101610676 A | 12/2009 |
| CN | 101626758 A | 1/2010 |
| CN | 103923084 A | 7/2014 |
| EP | 1038392 A1 | 9/2000 |
| EP | 1046399 A1 | 10/2000 |
| EP | 1240899 A2 | 9/2002 |
| EP | 1132393 B1 | 4/2003 |
| EP | 1473039 A1 | 11/2004 |
| EP | 2220116 A1 | 8/2010 |
| JP | H01167840 A | 7/1989 |
| JP | 2003509428 A | 3/2003 |
| JP | 2004/518615 A | 6/2004 |
| JP | 2005/089352 A | 4/2005 |
| JP | 2007520559 A | 7/2007 |
| JP | 2010526768 A | 8/2010 |
| JP | 2011/508749 A | 3/2011 |
| JP | 4934197 B2 | 5/2012 |
| JP | 2013507448 A | 3/2013 |
| JP | 5717109 B2 | 5/2015 |
| JP | 5841998 B2 | 1/2016 |
| WO | WO-1994/014436 A1 | 7/1994 |
| WO | WO-9728161 A1 | 8/1997 |
| WO | WO-1997/040028 A1 | 10/1997 |
| WO | WO-9749706 A1 | 12/1997 |
| WO | WO-1998/040381 A1 | 9/1998 |
| WO | WO-9841525 A1 | 9/1998 |
| WO | WO-9954286 A2 | 10/1999 |
| WO | WO-0000823 A1 | 1/2000 |
| WO | WO-2000/056331 A1 | 9/2000 |
| WO | WO-0056737 A2 | 9/2000 |
| WO | WO-0119829 A2 | 3/2001 |

(56) References Cited

FOREIGN PATENT DOCUMENTS

| | | |
|---|---|---|
| WO | WO-0125238 A2 | 4/2001 |
| WO | WO-0129058 A1 | 4/2001 |
| WO | WO-0141754 A2 | 6/2001 |
| WO | WO-0144258 A1 | 6/2001 |
| WO | WO-0119829 A3 | 9/2001 |
| WO | WO-0238797 A2 | 5/2002 |
| WO | WO-02076986 A1 | 10/2002 |
| WO | WO-02078731 A1 | 10/2002 |
| WO | WO-02080926 A1 | 10/2002 |
| WO | WO-2003/000187 A2 | 1/2003 |
| WO | WO-2003/004053 A1 | 1/2003 |
| WO | WO-03000187 A2 | 1/2003 |
| WO | WO-03013540 A1 | 2/2003 |
| WO | WO-03046200 A2 | 6/2003 |
| WO | WO-03097645 A1 | 11/2003 |
| WO | WO-2004/060319 A2 | 7/2004 |
| WO | WO-2004074290 A1 | 9/2004 |
| WO | WO-2004096253 A1 | 11/2004 |
| WO | WO-2004100868 A2 | 11/2004 |
| WO | WO-2005000197 A2 | 1/2005 |
| WO | WO-2005005429 A1 | 1/2005 |
| WO | WO-2005014599 A1 | 2/2005 |
| WO | WO-2005037836 A2 | 4/2005 |
| WO | WO-2005037843 A1 | 4/2005 |
| WO | WO-2004100868 A3 | 7/2005 |
| WO | WO-2005060956 A1 | 7/2005 |
| WO | WO-2005074603 A2 | 8/2005 |
| WO | WO-2006002871 A1 | 1/2006 |
| WO | WO-2006012422 A1 | 2/2006 |
| WO | WO-2006/036788 A2 | 4/2006 |
| WO | WO-2006036527 A1 | 4/2006 |
| WO | WO-2006036941 A2 | 4/2006 |
| WO | WO-2006050946 A1 | 5/2006 |
| WO | WO-2006053121 A2 | 5/2006 |
| WO | WO-2006071017 A1 | 7/2006 |
| WO | WO-2006099075 A2 | 9/2006 |
| WO | WO-2006124462 A2 | 11/2006 |
| WO | WO-2007002325 A1 | 1/2007 |
| WO | WO-2007058832 A2 | 5/2007 |
| WO | WO-2007087068 A2 | 8/2007 |
| WO | WO-2007136790 A2 | 11/2007 |
| WO | WO-2008039218 A2 | 4/2008 |
| WO | WO-2008/063727 A2 | 5/2008 |
| WO | WO-2008054827 A2 | 5/2008 |
| WO | WO-2008069881 A2 | 6/2008 |
| WO | WO-2008108636 A1 | 9/2008 |
| WO | WO-2008/121742 A2 | 10/2008 |
| WO | WO-2008/124138 A1 | 10/2008 |
| WO | WO-2008127659 A2 | 10/2008 |
| WO | WO-2009051822 A1 | 4/2009 |
| WO | WO-2009/118523 A1 | 10/2009 |
| WO | WO-2009/140853 A1 | 11/2009 |
| WO | WO-2009/149179 A2 | 12/2009 |
| WO | WO-2009158571 A1 | 12/2009 |
| WO | WO-2010009342 A2 | 1/2010 |
| WO | WO-2010/034670 A2 | 4/2010 |
| WO | WO-2010009342 A3 | 5/2010 |
| WO | WO-2010/065824 A2 | 6/2010 |
| WO | WO-2010/069809 A1 | 6/2010 |
| WO | WO-2010065898 A2 | 6/2010 |
| WO | WO-2010/093843 A2 | 8/2010 |
| WO | WO-2010126960 A1 | 11/2010 |
| WO | WO-2011034907 A2 | 3/2011 |
| WO | WO-2011/046771 A1 | 4/2011 |
| WO | WO-2011046964 A2 | 4/2011 |
| WO | WO-2011/068560 A1 | 6/2011 |
| WO | WO-2011/160206 A1 | 12/2011 |
| WO | WO-2011152351 A1 | 12/2011 |
| WO | WO-2011153514 A2 | 12/2011 |
| WO | WO-2011162515 A2 | 12/2011 |
| WO | WO-2012/001090 A1 | 1/2012 |
| WO | WO-2012021444 A1 | 2/2012 |
| WO | WO-2012158764 A1 | 11/2012 |
| WO | WO-2013/036994 A1 | 3/2013 |
| WO | WO-2013/059738 A2 | 4/2013 |
| WO | WO-2013/085893 A1 | 6/2013 |
| WO | WO-2013184572 A1 | 12/2013 |
| WO | WO-2014/004707 A1 | 1/2014 |
| WO | WO-2014004376 A2 | 1/2014 |
| WO | WO-2014018567 A1 | 1/2014 |
| WO | WO-2014/135669 A1 | 9/2014 |
| WO | WO-2014/159745 A1 | 10/2014 |
| WO | WO-2014/168975 A1 | 10/2014 |
| WO | WO-2015/013579 A1 | 1/2015 |
| WO | WO-2015/018522 A1 | 2/2015 |
| WO | WO-2015/048689 A1 | 4/2015 |
| WO | WO-2015/127234 A1 | 8/2015 |
| WO | WO-2016/161347 A1 | 10/2016 |

OTHER PUBLICATIONS

Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).
Agency for Toxic Substances and Disease Registry, Public Health Assessment Guidance Manual, (2005).
Ahn et al. Michael acceptors as a tool for anticancer drug design. Current Pharmaceutical Design 2(3):247-262 (1996).
American Cancer Society Melanoma Guidelines (Last Revised Sep. 5, 2014), p. 37.
Anderson. The process of structure-based drug design. Chem and Biol 10:787-797 (2003).
Apsel et al. Targeted Polypharmacology: Discovery of Dual Inhibitors of Tyrosine and Phosphoinositide Kinases. Nature Chem. Bio., 4(11):691-699 (2008).
Baselga. Targeting tyrosine kinases in cancer: the second wave. Science 312(5777):1175-1178 (2006).
Biospace, Dec. 8, 2009, pharmacyclics, Inc. (PCYC) announces presentation of interim results from phase I trial of its first-in-human btk inhibitor PCI-32765.
Brown et al. Phase Ib trial of AVL-292, a covalent inhibitor of Bruton's tyrosine kinase (Btk), in chronic lymphocytic leukemia (CLL) and B-non-Hodgkin lymphoma (B-NHL). J Clin. Oncol. 30(suppl):abstract 8032 (2012); [online][retrieved on Oct. 4, 2012] Retrieved from the Internet: < http://www.asco.org/ASCOv2/Meetings/Abstracts?&vmview=abst_detail_view&confID=114&abstractID=98841>.
Burger et al. CXCR4 antagonists: targeting the microenvironment in leukemia and other cancers, Leukemia 23:43-52 (2009).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Burger. Targeting the microenvironment in chronic lymphocytic leukemia is changing the therapeutic landscape. Curr. Opin. Oncol. 24(6):643-649 (Epub Sep. 6, 2012/Nov. 2012).
Byrd et al. Targeting BTK with Ibrutinib in relapsed chronic lymphocytic leukemia, NEJM 369(1):32-42 (Jul. 4, 2013).
Byrd, J.C., et al., 2013, "Targeting BTK with Ibrutinib in relapsed chronic lymphocytic leukemia", New England Journal of Medicine, vol. 369, No. 1, pp. 32-42.
Cannon. Chapter Nineteen in Burger's Medicinal Chemistry and Drug Discovery, Fifth Edition, vol. I: Principles and Practice, Wiley-Interscience 1995, pp. 783-802.
Carmi et al. Clinical perspectives for irreversible tyrosine kinase inhibitors in cancer. Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Chang et al. Egress of CD19+CD5+ cells into peripheral blood following treatment with the Bruton tyrosine kinase inhibitor inbrutinib in mantel cell lymphoma patients. Blood, 122:2412-2424 (2013).
Chang et al. PCI-45292, a Novel Btk Inhibitor with Optimized Pharmaceutical Properties, Demonstrates Potent Activities in Rodent Models of Arthritis. ACR/ARHP Scientific Meeting, Nov. 6-11, 2010, Poster #286.

(56) References Cited

OTHER PUBLICATIONS

Chavez et al. Ibrutinib: An Evidence-Based Review of Its Potential in the Treatment of Advanced Chronic Lymphocytic Leukemia. Core Evidence 8:37-45 (2013).
Chen et al. SYK-dependent tonic B-cell receptor signaling is a rational treatment target in diffuse large B-cell lymphoma. Blood 111(4):2230-2237 (2008) [E-pub Nov. 15, 2007].
Clinical Trial Report: NCT01105247 (NIH, USA), "Safety of PCI-32765 in Chronic Lymphocytic Leukemia."
Co-pending U.S. Appl. No. 14/855,270, filed Sep. 15, 2015.
Co-pending U.S. Appl. No. 14/856,217, filed Sep. 16, 2015.
Dana-Farber Cancer Institute. A Phase II Study of Ibrutinib Plus FCR in Previously Untreated, Younger Patients With Chronic Lymphocytic Leukemia (iFCR). In: ClinicalTrials.gov [Internet]. Bethesda (MD): National Library of Medicine (US). Sep. 23, 2014 [cited Feb. 5, 2015] Available from: https://clinicaltrial.gov/ct2/show/NCT02251548?term=NCT02251548 NLM Identifier: NCT02251548.
Dana-Farber Cancer Institute. Ibrutinib (PCI-32765) in Waldenstrom's Macroglobulinemia. In: ClinicalTrials.gov [Internet]. Bethesda (MD): National Library of Medicine (US). May 17, 2012—[cited Nov. 22, 2013]. Available from: http://clinicaltrials.gov/ct2/show/NCT01614821 NLM Identifier: NCT01614821.
Davids et al. Targeting the B Cell Receptor Pathway in Chronic Lymphocytic Leukemia. Leuk. Lymphoma (Epub May 23, 2012), 53(12):2362-2370 (Dec. 2012).
Davis et al. Chronic active B-cell receptor signalling in diffuse large B-cell lymphoma. Nature 463(7277):88-92 (2010).
Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).
Dias et al. Ibrutinib: A New Frontier in the Treatment of Chronic Lymphocytic Leukemia by Bruton's Tyrosine Kinase Inhibition. Cardiovascular & Hematological Agents in Medicinal Chemistry 11:265-271 (2013).
Edwards. BTK inhibition in myeloma: targeting the seed and the soil. Blood 120(9):1757-1759 (Aug. 2012).
Expert Scientific Group on Phase One Clinical Trials. Final Report. Nov. 2006, pp. C1, C35-38.
Fedorak et al. A novel colon-specific steroid prodrug enhances sodium chloride absorption in rat colitis. Am. J. Physiol. 269:G210-218 (1995).
Friedberg et al. Inhibition of Syk with fostamatinib disodium has significant clinical activity in non-Hodgkin lymphoma and chronic lymphocytic leukemia. Blood 115(13):2578-2585 (2010) [E-pub Nov. 17, 2009].
Gazitt et al. Differential mobilization of CD34+ Cells and lymphoma cells in non-Hodgkin's lymphoma patients mobilized with different growth factors, J of Hematotherapy & Stem Cell Research 10:167-176 (2001).
Giuliani. Multiple myeloma bone disease: pathophysiology of osteoblast inhibition. Blood (Epub Aug. 17, 2006) 108(13):3992-3996 (2006).
Glassman et al. The value of fluorescence in situ hybridization in the diagnosis and prognosis of chronic lymphocytic leukemia, Cancer Genetics and Cytogenetics 158:88-91 (2005).
Gordon et al. Somatic hypermutation of the B cell receptor genes B29 (Igb, CD79b) and mb1 (Iga, CD79a). PNAS 100(7):4126-4131 (2003).
Grosheck et al. Molecular Target Class Is Predictive of In vitro Response Profile. Cancer Res. 70:3677-3686 (2010).
Gura. Systems for Identifiying New Drugs Are Often Faulty. Science 278(5340):1041-1042 (1997).
Hagemeister. Rituximab for the treatment of non-Hodgkin's lymphoma and chronic lymphocytic leukaemia. Drugs 70(3):261-272 (2010).
Hata et al. Bruton's tyrosine kinase-mediated Interleukin-2 gene activation in mast cells. J. Biol. Chem. 273(18): 10979-10987 (1998).

Hiddeman et al. Rituximab Plus Chemotherapy in Follicular and Mantle Cell Lymphomas, Seminars in Oncology 30(1)Suppl.2:16-20 (Feb. 2003).
Higuchi et al. Pro-drugs as Novel Delivery Systems, vol. 14 of the A.C.S. Symposium Series (1975).
Hochhaus et al. A selective HPLC/RIA for dexamethasone and its prodrug dexamethasone-21-sulphobenzoate sodium in biological fluids. Biomed. Chrom., 6:283-286 (1992).
Honigberg et al. Targeting Btk in lymphoma: PCI-32765 inhibits tumor growth in mouse lymphoma models and a fluorescent analog of PCI-32765 is an active-site probe that enables assessment of Btk inhibition in vivo. ASH Annual Meeting Abstracts 1592. 110(11): 475A (Nov. 16, 2007).
Honigberg et al. Targeting Btk in Lymphoma: PCT-32765 Inhibits Tumor Growth in Mouse Lymphoma Models and a Fluorescent Analog of PCT-32765 Is an Active-Site Probe that Enables Assessment of Btk Inhibition In Vivo. Blood (Ash Annual Meeting Abstracts). 2007. 110:Abstract 1592.
Honigberg et al. The Bruton tyrosine kinase inhibitor PCI-32765 blocks B-cell activation and is efficacious in models of autoimmune disease and B-cell malignancy. PNAS USA 107:13075-13080 (2010).
Huhn et al. Rituximab therapy of patients with B-cell chronic lymphocytic leukemia. Blood 98(5):1326-1331 (Sep. 1, 2001).
Jaffe. The 2008 WHO classification of lymphomas: implications for clinical practice and translational research. Hematology 1:523-531 (2009).
Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013—[cited Nov. 22, 2013]. Available from: http://clinicaltrials.gov/ct2/show/NCT01833039 NLM Identifier: NCT01833039.
Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012—[cited Nov. 22, 2013]. Available from: http://clinicaltrials.gov/ct2/show/NCT01704963 NLM Identifier: NCT01704963.
Janssen Pharmaceutical K.K. Study of the Bruton's Tyrosine Kinase (BTK) Inhibitor Ibrutinib in Participants With Relapsed or Refractory Mantle Cell Lymphoma. In: ClinicalTrials.gov [Internet]. Bethesda (MD): National Library of Medicine (US). Jun. 19, 2014—[cited Feb. 5, 2015] Available from: https://clinicaltrial.gov/ct2/show/NCT02169180?term=NCT02169180 NLM Identifier: NCT02169180.
Janssen Research & Development, LLC. A Study to Evaluate the Effects of Ibrutinib on Cardiac Repolarization in Healthy Participants. In: ClinicalTrials.gov [Internet]. Bethesda (MD): National Library of Medicine (US). Oct. 20, 2014 [cited Feb. 5, 2015] Available from: https://clinicaltrial.gov/ct2/show/NCT02271438?term=NCT02271438 NLM Identifier: NCT02271438.
Janssen Research & Development, LLC. Pharmacokinetic and Pharmacodynamic Study to Evaluate Safety and Efficacy of the Combination of Ibrutinib With Nivolumab in Participants With Hematologic Malignancies. In: ClinicalTrials.gov [Internet]. Bethesda (MD): National Library of Medicine (US). Dec. 30, 2014 [cited Feb. 5, 2015] Available from: https://clinicaltrial.gov/ct2/show/NCT02329847?term=NCT02329847 NLM Identifier: NCT02329847.
Janssen Research and Development, LLC. A long-term extension study of PCI-32765 (Ibrutinib). In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01804686 NLM Identifier: NCT01804686.
Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US).

(56) References Cited

OTHER PUBLICATIONS

Aug. 19, 2013—[cited Nov. 22, 2013]. Available from: http://clinicaltrials.gov/ct2/show/NCT01969266 NLM Identifier: NCT01969266.

Janssen Research and Development, LLC. A study combining Ibrutinib with rituximab, cyclophosphamide, doxorubicin, vincristine, and prednisone in patients with CD20-positive B-cell non Hodgkin lymphoma. In: ClinicalTrials.gov [Internet]. Bethesda (MD): National Library of Medicine (US). Mar. 30, 2012—[cited Nov. 22, 2013]. Available from: http://clinicaltrials.gov/ct2/show/NCT01569750 NLM Identifier: NCT01569750.

Janssen Research and Development, LLC. A study of ibrutinib in combination with bendamustine and rituximab in patients with relapsed or refractory chronic lymphocytic leukemia or small lymphocytic lymphoma. In: ClinicalTrials.gov [Internet]. Bethesda (MD): National Library of Medicine (US). May 15, 2012—[cited Nov. 22, 2013]. Available from: http://clinicaltrials.gov/ct2/show/NCT01611090 NLM Identifier: NCT01611090.

Janssen Research and Development, LLC. A study of PCI-32765 (Ibrutinib) in combination with either bendamustine and rituximab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013—[cited Nov. 22, 2013]. Available from: http://clinicaltrials.gov/ct2/show/NCT01974440 NLM Identifier: NCT01974440.

Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013—[cited Nov. 22, 2013]. Available from: http://clinicaltrials.gov/ct2/show/NCT01779791 NLM Identifier: NCT01779791.

Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013—[cited Nov. 22, 2013]. Available from: http://clinicaltrials.gov/ct2/show/NCT01776840 NLM Identifier: NCT01776840.

Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013—[cited Nov. 22, 2013]. Available from: http://clinicaltrials.gov/ct2/show/NCT01973387 NLM Identifier: NCT01973387.

Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicalTrials.gov [Internet]. Bethesda (MD): National Library of Medicine (US). May 14, 2013—[cited Nov. 22, 2013]. Available from: http://clinicaltrials.gov/ct2/show/NCT01855750 NLM Identifier: NCT01855750.

Janssen Research and Development, LLC. A study to assess the absolute bioavailability of Oral PCI-32765 and the effect of grapefruit juice on the bioavailability of PCI-32765 in healthy participants. In: ClinicalTrials.gov [Internet]. Bethesda (MD): National Library of Medicine (US). May 28, 2013—[cited Nov. 22, 2013]. Available from: http://clinicaltrials.gov/ct2/show/study/NCT01866033 NLM Identifier: NCT01866033.

Janssen Research and Development, LLC. A study to assess the effect of ketoconazole on the pharmacokinetics of ibrutinib in healthy participants. In: ClinicalTrials.gov [Internet]. Bethesda (MD): National Library of Medicine (US). Jun. 18, 2012—[cited Nov. 22, 2013]. Available from: http://clinicaltrials.gov/ct2/show/NCT01626651 NLM Identifier: NCT01626651.

Janssen Research and Development, LLC. A study to assess the effect of rifampin on the pharmacokinetics of PCI-32765 in healthy participants. In: ClinicalTrials.gov [Internet]. Bethesda (MD): National Library of Medicine (US). Jan. 4, 2013—[cited Nov. 22, 2013]. Available from: http://clinicaltrials.gov/ct2/show/NCT01763021 NLM Identifier: NCT01763021.

Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine (US). Aug. 9, 2012—[cited Nov. 22, 2013]. Available from: http://clinicaltrials.gov/ct2/show/NCT01674322 NLM Identifier: NCT01674322.

Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01820936 NLM Identifier: NCT01820936.

Janssen Research and Development, LLC. A study to evaluate the efficacy and safety of ibrutinib, in patients with mantel cell lymphoma who progress after bortezomib therapy. In: ClinicalTrials.gov [Internet]. Bethesda (MD): National Library of Medicine (US). May 14, 2012—[cited Nov. 22, 2013]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: ClinicalTrials.gov [Internet]. Bethesda (MD): National Library of Medicine (US). Jan. 9, 2013—[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have received at least one prior therapy. In: ClinicalTrials.gov [Internet]. Bethesda (MD): National Library of Medicine (US). Jul. 18, 2012—[cited Nov. 22, 2013]. Available from: http://clinicaltrials.gov/ct2/show/NCT01646021 NLM Identifier: NCT01646021.

Kamb. What's wrong with our cancer models? Nature Reviews Drug Discovery 4:161-165 (2005).

Kola et al. Can the pharmaceutical industry reduce attrition rates? Nature Reviews Drug Discover 3:711-715 (2004).

Korade-Mirnics et al. Src kinase-mediated signaling in leukocytes. J. Leukoc. Bio., 68(5):603-613 (Nov. 2000).

Kozaki et al. Development of a Bruton's tyrosine kinase (Btk) inhibitor—ONO-WG-307, a potential treatment for B-cell malignancies. 53rd American Society of Hematology Annual Meeting and Exposition, San Diego, CA, Poster #857 (Dec. 10-13, 2011).

Kuglstatter et al. Insights into the conformational flexibility of Bruton's tyrosine kinase from multiple ligand complex structures. Protein Science 20(2):428-436 (2011) [E-pub Dec. 17, 2010].

Larsen et al. Int. J. Pharmaceutics. 47:103 (1988).

Larsen et al.Prodrug forms for the sulfonamide group. I. Evaluation of N-acyl derivatives, N-sulfonylaminades, N-sulfonylsulfilimines and sulfonylureas as possible prodrug derivatives. Int. J. Pharmaceutics 37:87-95 (1987).

Le Tourneau et al. Dose Escalation Methods in Phase I Cancer Clinical Trials. J. Natl Cancer 101:708-720 (2009).

Leaf. Why Are We Losing the War on Cancer (and How to Win It). Health Admin. V. XVII, No. 1, pp. 172-183 (2005).

Li et al. Activation of Bruton's Tyrosine Kinase (BTK) by a Point Mutation in its Pleckstrin Homology (PH) domain. Immunity 2:451-460 (1995).

Lichtman. Battling the hematological malignancies: The 200 years' war. The Oncologist 13:126-138 (2008).

Lin et al. Selective Itk inhibitors block T-cell activation and murine lung inflammation, Biochemistry 43:11056-11062 (2004).

Lossos. Molecular Pathogenesis of Diffuse Large B-Cell Lymphoma. J. Clin. Oncol. 23(26):6351-6357 (Sep. 10, 2005).

Lou et al. Bruton's tyrosine kinase inhibitors: approaches to potent and selective inhibition, preclinical and clinical evaluation for inflammatory diseases and B cell malignancies. J Med Chem. May 24, 2012;55(10):4539-50 Publication Date (Web): Mar. 6, 2012.

(56) References Cited

OTHER PUBLICATIONS

MacPartlin et al. Bruton's tyrosine kinase is not essential for Bcr-Abl-mediated transformation of lymphoid or myeloid cells. Leukemia 22:1354-1360 (2008).
Maddocks et al. Ibrutinib in B-cell lymphomas. Current Treatment Options in Oncology 15:226-237 (2014) (Epub: Feb. 1, 2014).
Mallis et al. Structural characterization of a proline-driven conformational switch within the Itk SH2 domain. Nat. Struct. Biol., 9(12):900-905 (2002).
Marina et al. Biology and Therapeutic Advances for Pediatric Osteosarcoma. The Oncologist 9:422-441 (2004).
Martin et al. Novel therapeutic targets in mantle cell lymphoma. Expert Opin. In Therapeutic Targets 11:929-940 (2007).
McConathy et al. Stereochemistry in Drug Action. J Clinical Psychiatry. 5:70-73 (2003).
McLoed et al. Gastroenterol, 106:405-413 (1994).
M.D. Anderson Cancer Center. A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). Dec. 17, 2014 [cited Feb. 5, 2015] Available from: https://clinicaltrial.gov/ct2/show/NCT02321540?term=NCT02321540 NLM Identifier: NCT02321540.
M.D. Anderson Cancer Center. A Phase I/II Trial of PCI-32765 (BTK Inhibitor) in Combination With Carfilzomib in Relapse/Refractory Mantle Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269085 NLM Identifier: NCT02269085.
M.D. Anderson Cancer Center. Ibrutinib Post Stem Cell Transplantation (SCT) in Double-Hit B-Cell Lymphoma. In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272686?term=NCT02272686 NLM Identifier: NCT02272686.
M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013—[cited Apr. 15, 2014]. Available from: http://clinicaltrials.gov/ct2/show/NCT02007044 NLM Identifier: NCT02007044.
M.D. Anderson Cancer Center. Phase 2 ibrutinib + rituximab in relapsed/refractory mantel cell lymphoma (R/R MCL). In: ClinicalTrials.gov [Internet]. Bethesda (MD): National Library of Medicine (US). Jun. 14, 2013—[cited Nov. 22, 2013]. Available from: http://clinicaltrials.gov/ct2/show/NCT01880567 NLM Identifier: NCT01880567.
M.D. Anderson Cancer Center. Phase 2 study of the combination of Bruton's tyrosine kinase inhibitor PCI-32765 and rituximab in high-risk chronic lymphocytic leukemia and small lymphocytic lymphoma patients. In: ClinicalTrials.gov [Internet]. Bethesda (MD): National Library of Medicine (US). Jan. 25, 2012—[cited Nov. 22, 2013]. Available from: http://clinicaltrials.gov/ct2/show/NCT01520519 NLM Identifier: NCT01520519.
M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012 [cited Nov. 22, 2013]. Available from: http://clinicaltrials.gov/ct2/show/NCT01752426 NLM Identifier: NCT01752426.
Memorial Sloan-Kettering Cancer Center. Bruton's Tyrosine Kinase (BTK) Inhibitor, Ibrutinib, in Patients With Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US). Dec. 9, 2014 [cited Feb. 5, 2015] Available from: https://clinicaltrial.gov/ct2/show/NCT02315326?term=NCT02315326 NLM Identifier: NCT02315326.
Mendel et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9(1):327-337 (2003).
Middendorp et al. Function of Bruton's Tyrosine Kinase during B Cell Development is Partially Independent of its Catalytic Activity. J Immunol 171:5988-5996 (2003).
Middendorp et al. Tumor Suppressor Function of Bruton Tyrosine Kinase is Independent of its catalytic activity. Blood 105(1):259-261 (2005).
Mukoyama et al. Preparation of imidazol [1,5-a]pyrazine derivatives, pharmaceutical compositions containing them, and their uses for prevention or treatment of protein tyrosine kinase-related diseases, retrieved from STN Database Accession No. 2005:299462 Patent No. JP2005089352, Apr. 7, 2005, *abstract*.
National Cancer Institute. Ibrutinib and Combination Chemotherapy in Treating Patients With Relapsed or Refractory Diffuse Large B-Cell Lymphoma. In: ClinicalTrials.gov [Internet]. Bethesda (MD): National Library of Medicine (US). Jul. 16, 2014 [cited Feb. 5, 2015] Available from: https://clinicaltrial.gov/ct2/show/NCT02219737?term=NCT02219737 NLM Identifier: NCT02219737.
National Cancer Institute. Ibrutinib and Palbociclib Isethionate in Treating Patients With Previously Treated Mantle Cell Lymphoma. In: ClinicalTrials.gov [Internet]. Bethesda (MD): National Library of Medicine (US). Jun. 9, 2014—[cited Feb. 5, 2015] Available from: https://clinicaltrial.gov/ct2/show/NCT02159755?term=NCT02159755 NLM Identifier: NCT02159755 .
National Cancer Institute. Ibrutinib in Treating Patients With Relapsed or Refractory B-cell Acute Lymphoblastic Leukemia. In: ClinicalTrials.gov [Internet]. Bethesda (MD): National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.
National Cancer Institute. Ibrutinib in Treating Relapsed or Refractory B-cell Non-Hodgkin Lymphoma in Patients With HIV infection. In: ClinicalTrials.gov [Internet]. Bethesda (MD): National Library of Medicine (US). Apr. 7, 2014 [ cited Feb. 5, 2015]. Available from: https://clinicaltrial.gov/ct2/show/NCT02109224?term=NCT02109224. NLM Identifier: NCT02109224 .
National Cancer Institute. Lenalidomide, Ibrutinib, and Rituximab in Treating Patients With Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://clinicaltrial.gov/ct2/show/NCT02160015?term=NCT02160015 NLM Identifier: NCT02160015.
National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US). Nov. 2, 2013—[cited Nov. 22, 2013]. Available from: http://clinicaltrials.gov/ct2/show/NCT01981512 NLM Identifier: NCT01981512.
National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014—[cited Apr. 15, 2014]. Available from: http://clinicaltrials.gov/ct2/show/NCT02048813 NLM Identifier: NCT02048813.
National Cancer Institute (NCI). Ibrutinib in treating patients with relapsed hairy cell leukemia. In: ClinicalTrials.gov [Internet]. Bethesda (MD): National Library of Medicine (US). Apr. 24, 2013—[cited Nov. 22, 2013]. Available from: http://clinicaltrials.gov/ct2/show/NCT01841723 NLM Identifier: NCT01841723.

(56) References Cited

OTHER PUBLICATIONS

National Cancer Institute (NCI). Ibrutinib in treating patients with relapsed or refractory follicular lymphoma. In: ClinicalTrials.gov [Internet]. Bethesda (MD): National Library of Medicine (US). May 6, 2013—[cited Nov. 22, 2013]. Available from: http://clinicaltrials.gov/ct2/show/NCT01849263 NLM Identifier: NCT01849263.

National Cancer Institute (NCI). Lenalidomide and ibrutinib in treating patients with relapsed or refractory B-Cell non-Hodgkin lymphoma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01955499 NLM Identifier: NCT01955499.

National Cancer Institute (NCI). Rituximab and bendamustine hydrochloride, rituximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886872 NLM Identifier: NCT01886872.

National Cancer Institute (NCI). Rituximab, lenalidomide, and ibrutinib in treating patients with previously untreated stage II-IV follicular lymphoma. In: ClinicalTrials.gov [Internet]. Bethesda (MD): National Library of Medicine (US). Apr. 9, 2013—[cited Nov. 22, 2013]. Available from: http://clinicaltrials.gov/ct2/show/NCT01829568 NLM Identifier: NCT01829568.

National Cancer Institute. Phase 1 Study of Ibrutinib and Immuno-Chemotherapy Using Dose-Adjusted-Temozolomide, Etoposide, Doxil, Dexamethasone, Ibrutinib,Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.

National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886859 NLM Identifier: NCT01886859.

National Heart, Lung, and Blood Institute (NHLBI). PCI-32765 for special cases of chronic lymphocytic leukemia or small lymphocytic lymphoma. In: ClinicalTrials.gov [Internet]. Bethesda (MD): National Library of Medicine (US). Dec. 22, 2011—[cited Nov. 22, 2013]. Available from: http://clinicaltrials.gov/ct2/show/NCT01500733 NLM Identifier: NCT01500733.

Neidle. Cancer Drug Design and Discovery. Elsevier/Academic Press. pp. 427-431 (2008).

Nogrady (1985) Medicinal Chemistry a Biochemical Approach, Oxford University Press, New York, pp. 388-392.

Northwestern University. Ibrutinib After Intensive Induction in Treating Patients With Previously Untreated Mantle Cell Lymphoma. In: ClinicalTrials.gov [Internet]. Bethesda (MD): National Library of Medicine (US). Sep. 12, 2014 [cited 2-15 Feb. 5] Available from: https://clinicaltrial.gov/ct2/show/NCT02242097?term=NCT02242097 NLM Identifier: NCT02242097.

Ohio State University Comprehensive Cancer Center. Pci-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2012—[cited Nov. 22, 2013]. Available from: http://clinicaltrials.gov/ct2/show/NCT01589302 NLM Identifier: NCT01589302.

Ohio State University Comprehensive Cancer Center. Rituxan/Bendamustine/PCI-32765 in relapsed DLBCL, MCL, or indolent non-Hodgkin's lymphoma. In: ClinicalTrials.gov [Internet]. Bethesda (MD): National Library of Medicine (US). Nov. 1, 2011— [cited Feb. 6, 2014]. Available from: http://clinicaltrials.gov/ct2/show/NCT01479842 NLM Identifier: NCT01479842.

Pagel et al. Induction of apoptosis using inhibitors of lysophosphatidic acid acyltransferase-beta and anti-CD20 monoclonal antibodies for treatment of human non-Hodgkin's lymphomas. Clin. Cancer Res. (Epub Jul. 6, 2005), 11(13):4857-4866 (2005).

Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (Resonate-2). In: ClinicalTrials.gov [Internet]. Bethesda (MD): National Library of Medicine (US). Oct. 29, 2012—[cited Nov. 22, 2013]. Available from: http://clinicaltrials.gov/ct2/show/NCT01722487 NLM Identifier: NCT01722487.

Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012—[cited Nov. 22, 2013]. Available from: http://clinicaltrials.gov/ct2/show/NCT01744691 NLM Identifier: NCT01744691.

Pharmacyclics, Inc. A Multi-Center Study of Ibrutinib in Combination With Obinutuzumab Versus Chlorambucil in Combination With Obinutuzumab in Patients With Treatment naïve CLL or SLL. In: ClinicalTrials.gov [Internet]. Bethesda (MD): National Library of Medicine (US). Oct. 1, 2014 [cited Feb. 5, 2015] Available from: https://clinicaltrial.gov/ct2/show/NCT02264574?term=NCT02264574 NLM Identifier: NCT02264574 .

Pharmacyclics, Inc. A phase 3 study of ibrutinib (PCI-32765) versus ofatumumab in patients with relapsed or refractory chronic lymphocytic leukemia (Resonate). In: ClinicalTrials.gov [Internet]. Bethesda (MD): National Library of Medicine (US). Apr. 11, 2012—[cited Nov. 22, 2013]. Available from: http://clinicaltrials.gov/ct2/show/NCT01578707 NLM Identifier: NCT01578707.

Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012—[cited Nov. 22, 2013 ]. Available from: http://clinicaltrials.gov/ct2/show/NCT01724346 NLM Identifier: NCT01724346.

Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine (US). Oct. 7, 2010—[cited Nov. 22, 2013]. Available from: http://clinicaltrials.gov/ct2/show/NCT01217749 NLM Identifier: NCT01217749.

Pharmacyclics, Inc. Ibrutinib and Lenalidomide With Dose Adjusted EPOCH-R in Subjects With Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.

Pharmacyclics, Inc. Ibrutinib in combination with lenalidomide, with and without rituximab in participants with relapsed or refractory diffuse large B-cell lymphoma. In: ClinicalTrials.gov [Internet]. Bethesda (MD): National Library of Medicine (US). Feb. 10, 2014—[cited Apr. 15, 2014]. Available from: http://clinicaltrials.gov/ct2/show/NCT02077166 NLM Identifier: NCT02077166.

Pharmacyclics, Inc. Ibrutinib With Rituximab in Previously Treated Adults With Waldenstrom's Macroglobulinemia. In: ClinicalTrials.gov [Internet]. Bethesda (MD): National Library of Medicine (US). Jun. 9 2014 [cited Feb. 5, 2015] Available from: https://clinicaltrial.gov/ct2/show/NCT02165397?term=NCT02165397 NLM Identifier: NCT02165397.

Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010—[cited Nov. 22, 2013]. Available from: http://clinicaltrials.gov/ct2/show/NCT01236391 NLM Identifier: NCT01236391.

(56) References Cited

OTHER PUBLICATIONS

Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01325701 NLM Identifier: NCT01325701.
Pharmacyclics, Inc. Safety and tolerability study of PCI-32765 combined with fludarabine/cyclophosphamide/rituximab (FCR) and bendamustine/rituximab (BR) in chronic lymphocytic leukemia (CLL). In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01292135 NLM Identifier: NCT01292135.
Pharmacyclics, Inc. Safety and tolerability study of PCI-32765 in B Cell lymphoma and chronic lymphocytic leukemia. In: ClinicalTrials.gov [Internet]. Bethesda (MD): National Library of Medicine (US). Apr. 19, 2010—[cited Nov. 25, 2013]. Available from: http://clinicaltrials.gov/ct2/show/NCT01109069 NLM Identifier: NCT01109069.
Pharmacyclics, Inc. Safety of PCI-32765 in chronic lymphocytic leukemia. In: ClinicalTrials.gov [Internet]. Bethesda (MD): National Library of Medicine (US). Apr. 13, 2010—[cited Nov. 22, 2013]. Available from: http://clinicaltrials.gov/ct2/show/NCT01105247 NLM Identifier: NCT01105247.
Pharmacyclics, Inc. Study of the Bruton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01962792 NLM Identifier: NCT01962792.
Pharmacyclics, Inc. Study of the Bruton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013—[cited Nov. 22, 2013]. Available from: http://clinicaltrials.gov/ct2/show/NCT01980654 NLM Identifier: NCT01980654.
Pharmacyclics, Inc. Study of the Bruton's Tyrosine Kinase Inhibitor in Subjects With Chronic Graft Versus Host Disease. In: ClinicalTrials.gov [Internet]. Bethesda (MD): National Library of Medicine (US). Jul. 11, 2014 [cited Feb. 5, 2015] Available from: https://clinicaltrial.gov/ct2/show/NCT02195869?term=NCT02195869 NLM Identifier: NCT02195869.
Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011—[cited Nov. 22, 2013]. Available from: http://clinicaltrials.gov/ct2/show/NCT01478581 NLM Identifier: NCT01478581.
Pharmacyclics, Inc. Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29, 2013—[cited Nov. 22, 2013]. Available from: http://clinicaltrials.gov/ct2/show/NCT01980628 NLM Identifier: NCT01980628.
Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009—[cited Nov. 22, 2013]. Available from: http://clinicaltrials.gov/ct2/show/NCT00849654 NLM Identifier: NCT00849654.
Pharmacyclics: Pharmacyclics initiates phase 1 clinical trial of novel oral Btk inhibitor for refractory B-cell non-Hodgkin's lymphoma. The American Association of Cancer Research (AACR) 100th Annual Meeting in Denver, CO (Apr. 13, 2009).
Picci. Osteosarcoma (Osteogenic Sarcoma). Orphanet J. Rare Diseases 2(6):1-4 (2007).
Pileri et al. Mantle Cell Lymphoma. Haematologica 94(11):1488-1492 (2009).
Pollyea et al. A Phase I Dose Escalation Study of the Btk Inhibitor PCI-32765 in Relapsed and Refractory B Cell Non-Hodgkin Lymphoma and Use of a Novel Fluorescent Probe Pharmacodynamic Assay, Poster Abstract #3713, 51st ASH Annual Meeting and Exposition (Dec. 3, 2009).
Powers et al. Irreversible Inhibitors of Serine, Cysteine, and Threonine Proteases. Chem. Rev., 102(12):4639-4750 (2002).
Prakash et al. Chicken sarcoma to human cancers: a lesson in molecular therapeutics. The Ochsner Journal, 7(2):61-64 (Jan. 1, 2007).
PRNewswire. Pharmacyclics, Inc. Announces Presentation of Interim Results from Phase I Trial of its First-in-Human Btk Inhibitor PCI-32765. Dec. 7, 2009.
PRNewswire. Update on Preclinical Finding and Development Timeline for PCI-45292. Mar. 2, 2011.
Prenata et al., "Separation on the basis of size: Gel permeation chromatography," Protein Purification Methods: A Practical Approach, (Harris & Angal Eds.) IRL Press 1989 293-306.
Rabin et al. Absolute Lymphocyte Counts Refine MRD-Based Risk Stratification in Pediatric ALL. Blood (Ash Annual Meeting Abstracts) 114:Abstract 1593 (2009).
Rao et al. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408 (2005).
Rastetter et al. Rituximab: expanding role in therapy for lymphomas and autoimmune diseases. Ann. Rev. Med 55:477-503 (2004).
Ritter et al. Osteosarcoma. Ann. Oncol. 21(Supplement 7):320-325 (2010).
Robak et al. A Targeted Therapy for Protein and Lipid Kinases in Chronic Lymphocytic Leukemia. Curr. Med. Chem. (Epub Jul. 24, 2012), 19(31):5294-5318 (2012).
Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).
Roberts, Jr. et al. Trends in the Risks and Benefits to Patients With Cancer Participating in Phase 1 Clinical Trials. JAMA 292(17):2130-2140 (2004).
Rushworth et al. BTK inhibitor ibrutinib is cytotoxic to myeloma and potently enhances bortezomib and lenalidomide activities through NF-κB. Cell Signal. Sep. 11, 2012. pii: S0898-6568(12)00250-1. doi: 10.1016/j.cellsig.2012.09.008. [Epub ahead of print].
Rushworth et al. BTK inhibitor ibrutinib is cytotoxic to myeloma and potently enhances bortezomib and lenalidomide activities through NF-κB. Cell Signal (Epub Sep. 11, 2012), 25(1):106-112 (Jan. 2013).
Saulnier et al. (1994), Bioorganic and Medicinal Chemistry Letters, vol. 4, p. 1985.
Schnute et al. Bruton's tyrosine kinase (Btk). Anti-Inflammatory Drug Discovery. Ed. J.I. Levin and S. Laufer. (2012), pp. 297-326.
Schwamb et al. B-cell receptor triggers drug sensitivity of primary CLL cells by controlling glucosylation of ceramides. Blood (Epub Aug. 27, 2012), 120(19):3978-3985 (Nov. 2012).
Science Daily. Counting tumor cells in blood predicts treatment benefit in prostate cancer. (Jul. 7, 2008), http://www.sciencedaily.com/releases/2008/07/080706083142.htm. last accessed Jul. 23, 2013.
Science Daily. Drug shows surprising efficacy as treatment for chronic leukemia, mantle cell lymphoma. (Jun. 19, 2013), http://www.sciencedaily.com/releases/2013/06/130619195217.htm, last accessed Jan. 30, 2014.
Silverman. The Organic Chemistry of Drug Design and Drug Action, Academic Press, Inc., San Diego, pp. 352-401 (1992).
Sinkula et al. Rationale for design of biologically reversible drug derivatives: prodrugs. J. Pharm. Sci., 64:181-210 (1975).
Sivina et al. CCL3 (MIP-1a) Plasma Levels and the Risk for Disease Progression in Chronic Lymphocytic Leukemia. Blood 117(5):1662-1669 (2010).
STN Registry No. 936563-96-1. Ibrutinib. Retrieved from STN Registry Jul. 27, 2015. 1 pg.
Strimbu et al. What are biomarkers? Curr Opin HIV AIDS 5(6):463-466 (2010.

(56) References Cited

OTHER PUBLICATIONS

Takahashi et at. Serum CCL3 and CCL4 Levels Function As Novel Prognostic Markers in Diffuse Large B Cell Lymphoma [online]. 54th ASH Annual Meeting and Exposition. [retrieved on Apr. 21, 2015], Abstract 2709. Retrieved from the Internet: <URL: https://ash.confex.com/ash/2012/webprogram/Paper53900.html>.
TG Therapeutics, Inc. Ublituximab + ibrutinib in select B-cell malignancies. In: ClinicalTrials.gov [Internet]. Bethesda (MD): National Library of Medicine (US). Dec. 11, 2013—[cited Apr. 15, 2014]. Available from: http://clinicaltrials.gov/ct2/show/NCT02013128 NLM Identifier: NCT02013128.
The Lymphoma Academic Research Organisation. Bruton's tyrosine kinase (BTK) inhibition in B-cell lymphomas (BIBLOS). In: ClinicalTrials.gov [Internet]. Bethesda (MD): National Library of Medicine (US). Jan. 31, 2014—[cited Apr. 15, 2014]. Available from: http://clinicaltrials.gov/ct2/show/NCT02055924 NLM Identifier: NCT02055924.
Thiel. Structure-aided drug design's next generation. Nature Biotechnol 2:513-519 (2004).
Traxler et al. Use of a Pharmacophore Model for the Design of EGF-R Tyrosine Kinase Inhibitors: 4-(Phenylamino)pyrazolo[3,4-d]pyrimidines. J. Med Chem 40(22):3601-3616 (1997).
University of California, San Diego. A Phase Ib/II Study of Ibrutinib in Combination With GA101—Obinutuzumab in Previously Untreated Chronic Lymphocytic Leukemia (CLL) Patients Over 65 Years of Age or With Comorbidities That Preclude the Use of Chemotherapy Based Treatment. In: ClinicalTrials.gov [Internet]. Bethesda (MD): National Library of Medicine (US). Oct. 30, 2014 [cited Feb. 5, 2015] Available from: https://clinicaltrial.gov/ct2/show/NCT02315768?term=NCT02315768 NLM Identifier: NCT02315768.
U.S. Appl. No. 12/594,805 Final Office Action dated Jun. 27, 2013.
U.S. Appl. No. 12/594,805 Office Action dated Oct. 15, 2012.
U.S. Appl. No. 13/003,811 Final Office Action dated Oct. 11, 2013.
U.S. Appl. No. 13/003,811 Non-Final Office Action dated Aug. 3, 2015.
U.S. Appl. No. 13/003,811 Office Action dated Feb. 25, 2013.
U.S. Appl. No. 13/153,291 Final Office Action dated Mar. 26, 2015.
U.S. Appl. No. 13/153,291 Final Office Action dated Jan. 3, 2014.
U.S. Appl. No. 13/153,291 Office Action dated Jul. 18, 2014.
U.S. Appl. No. 13/153,291 Office Action dated Jul. 5, 2013.
U.S. Appl. No. 13/153,317 Final Office Action dated Jan. 23, 2014.
U.S. Appl. No. 13/153,317 Non-Final Office Action dated Jul. 23, 2015.
U.S. Appl. No. 13/153,317 Office Action dated Jul. 29, 2013.
U.S. Appl. No. 13/232,784 Non-Final Office Action dated Oct. 9, 2015.
U.S. Appl. No. 13/232,784 Office Action dated Mar. 6, 2014.
U.S. Appl. No. 13/232,784 Office Action dated Sep. 15, 2014.
U.S. Appl. No. 13/340,276 Final Office Action dated Apr. 4, 2013.
U.S. Appl. No. 13/340,276 Office Action dated Sep. 10, 2013.
U.S. Appl. No. 13/340,276 Office Action dated Sep. 26, 2012.
U.S. Appl. No. 13/340,522 Examiner Initiated Interview Summary, dated Dec. 23, 2012.
U.S. Appl. No. 13/340,522 Final Office Action dated Nov. 1, 2013.
U.S. Appl. No. 13/340,522 Notice of Allowance, dated Jan. 27, 2014.
U.S. Appl. No. 13/340,522 Office Action dated Mar. 13, 2013.
U.S. Appl. No. 13/340,522 Original Claims, dated Dec. 29, 2011.
U.S. Appl. No. 13/340,522 Preliminary Amendment and Response to Restriction Requirement, dated Feb. 4, 2013.
U.S. Appl. No. 13/340,522 Requirement for Restriction/Election, dated Jan. 3, 2013.
U.S. Appl. No. 13/340,522 Response to Final Office Action, dated Dec. 17, 2013.
U.S. Appl. No. 13/340,533 Final Office Action dated Feb. 25, 2013.
U.S. Appl. No. 13/340,533 Final Office Action dated Oct. 12, 2012.
U.S. Appl. No. 13/340,559 Office Action dated Mar. 17, 2014.
U.S. Appl. No. 13/340,559 Office Action dated Sep. 26, 2014.
U.S. Appl. No. 13/340,621 Office Action dated Mar. 6, 2014.
U.S. Appl. No. 13/340,621 Office Action dated Sep. 26, 2014.
U.S. Appl. No. 13/341,695 Final Office Action dated Jun. 7, 2013.
U.S. Appl. No. 13/341,695 office Action dated Jun. 11, 2015.
U.S. Appl. No. 13/341,695 Office Action dated Feb. 1, 2013.
U.S. Appl. No. 13/341,695 Office Action dated Oct. 31, 2014.
U.S. Appl. No. 13/341,708 Office Action dated Jan. 22, 2014.
U.S. Appl. No. 13/404,422 Final Office Action dated Aug. 12, 2015.
U.S. Appl. No. 13/404,422 Final Office Action dated Apr. 16, 2013.
U.S. Appl. No. 13/404,422 Non-Final Action dated Feb. 11, 2015.
U.S. Appl. No. 13/404,422 Office Action dated Feb. 21, 2014.
U.S. Appl. No. 13/404,422 Office Action dated Sep. 28, 2012.
U.S. Appl. No. 13/410,110 Final Office Action dated Jun. 12, 2015.
U.S. Appl. No. 13/410,110 Final Office Action dated Apr. 16, 2013.
U.S. Appl. No. 13/410,110 Non-Final Office Action dated Feb. 4, 2015.
U.S. Appl. No. 13/410,110 Office Action dated Feb. 24, 2014.
U.S. Appl. No. 13/410,110 Office Action dated Sep. 28, 2012.
U.S. Appl. No. 13/410,110 Office Action dated Sep. 29, 2014.
U.S. Appl. No. 13/430,173 Final Office Action dated Jul. 2, 2015.
U.S. Appl. No. 13/430,173 Non-Final Office Action dated Mar. 19, 2015.
U.S. Appl. No. 13/430,173 Office Action dated Feb. 25, 2014.
U.S. Appl. No. 13/430,173 Office Action dated Sep. 9, 2014.
U.S. Appl. No. 13/439,775 Final Office Action dated Jun. 4, 2015.
U.S. Appl. No. 13/439,775 Final Office Action dated Jun. 17, 2013.
U.S. Appl. No. 13/439,775 Non-Final Action dated Feb. 10, 2015.
U.S. Appl. No. 13/439,775 Office Action dated Dec. 10, 2012.
U.S. Appl. No. 13/439,775 Office Action dated Mar. 6, 2014.
U.S. Appl. No. 13/439,775 Office Action dated Sep. 26, 2014.
U.S. Appl. No. 13/543,065 Office Action dated Feb. 26, 2015.
U.S. Appl. No. 13/543,065 Office Action dated Mar. 25, 2014.
U.S. Appl. No. 13/543,065 Office Action dated Oct. 8, 2014.
U.S. Appl. No. 13/543,394 Office Action dated Feb. 27, 2015.
U.S. Appl. No. 13/543,394 Office Action dated Mar. 25, 2014.
U.S. Appl. No. 13/543,394 Office Action dated Oct. 9, 2014.
U.S. Appl. No. 13/543,399 Final Office Action dated Jan. 26, 2015.
U.S. Appl. No. 13/543,399 Non-Final Office Action dated Aug. 27, 2015.
U.S. Appl. No. 13/543,399 Office Action dated Mar. 26, 2014.
U.S. Appl. No. 13/543,399 Office Action dated Sep. 10, 2014.
U.S. Appl. No. 13/543,399 Office Action dated Sep. 24, 2014.
U.S. Appl. No. 13/606,949 Final Office Action dated Feb. 14, 2014.
U.S. Appl. No. 13/606,949 Non-Final Office Action dated Oct. 29, 2013.
U.S. Appl. No. 13/607,036 Final Office Action dated Jun. 24, 2013.
U.S. Appl. No. 13/607,036 Non-Final Office Action dated Mar. 10, 2015.
U.S. Appl. No. 13/607,036 Office Action dated Mar. 6, 2014.
U.S. Appl. No. 13/607,036 Office Action dated Nov. 14, 2012.
U.S. Appl. No. 13/607,036 Office Action dated Sep. 26, 2014.
U.S. Appl. No. 13/612,143 Final Office Action dated Dec. 5, 2014.
U.S. Appl. No. 13/612,143 Office Action dated Jun. 23, 2014.
U.S. Appl. No. 13/619,466 Final Office Action dated Jun. 18, 2015.
U.S. Appl. No. 13/736,812 Non-Final Office Action dated Sep. 10, 2015.
U.S. Appl. No. 13/736,812 Office Action dated Mar. 18, 2014.
U.S. Appl. No. 13/736,812 Office Action dated Oct. 10, 2014.
U.S. Appl. No. 13/747,319 Non-Final Office Action dated Sep. 15, 2015.
U.S. Appl. No. 13/747,319 Office Action dated Mar. 20, 2014.
U.S. Appl. No. 13/747,319 Office Action dated Oct. 10, 2014.
U.S. Appl. No. 13/747,322 Office Action dated Mar. 20, 2014.
U.S. Appl. No. 13/869,700 Non-Final Office Action dated Sep. 10, 2015.
U.S. Appl. No. 13/869,700 Office Action dated May 16, 2014.
U.S. Appl. No. 13/869,700 Office Action dated Nov. 28, 2014.
U.S. Appl. No. 13/908,949 Office Action dated Jun. 11, 2015.
U.S. Appl. No. 13/965,135 Office Action dated Dec. 22, 2014.
U.S. Appl. No. 14/069,222 Final Office Action dated Jun. 18, 2015.
U.S. Appl. No. 14/069,222 Office Action dated Oct. 9, 2014.
U.S. Appl. No. 14/091,196 Office Action dated May 19, 2015.
U.S. Appl. No. 14/179,457 Final Office Action dated Dec. 22, 2014.
U.S. Appl. No. 14/179,457 Office Action dated Aug. 4, 2014.

(56) References Cited

OTHER PUBLICATIONS

U.S. Appl. No. 14/188,390 Non-Final Office Action dated Aug. 26, 2015.
U.S. Appl. No. 14/339,363 Office Action dated Jan. 12, 2015.
U.S. Appl. No. 14/448,963 Office Action dated Nov. 12, 2014.
U.S. Appl. No. 14/450,068 Non-Final Office Action dated May 21, 2015.
U.S. Appl. No. 14/605,854 Non-Final Office Action dated May 27, 2015.
U.S. Appl. No. 14/605,857 Non-Final Office Action dated Oct. 7, 2015.
Vose. Mantle cell lymphoma: 2012 update on diagnosis, risk-stratification, and clinical management. Am. J. Hematol. 87(6):604-609 (Jun. 2012).
Wang et al. "Ibrutinib and rituximab are an efficacious and safe combination in relapsed mantle cell lymphoma: preliminary results from a Phase II clinical trial," Oral Abstract Session 624, 56th ASH Annual Meeting and Exposition (Dec. 6-9, 2014).
Wang et al. Targeting BTK with ibrutinib in relapsed or refractory mantel-cell lymphoma. N Engl J Med 369(6):507-516 (Aug. 8, 2013).
Wilkinson et al. Selective tyrosine kinase inhibitors. Expert Opin. Emerging Drugs 5(3):287-297 (2000).
Wilson et al., "The Bruton's tyrosine kinase (BTK) inhibitor, ibrutinib (PCI-32765), has preferential activity in the ABC subtype of relapsed/refractory de novo diffuse large B-cell lymphoma (DLBCL): interim results of a multicenter, open-label, phase 2 study," Blood 120:Abstract 686 (2012).
Witzens-Harig et al. Current treatment of mantle cell lymphoma: results of a national survey and consensus meeting. Ann Hematol. (Epub Aug. 29, 2012), 91(11):1765-1772 (Nov. 2012).
Witzig et al. Detection of myeloma cells in the peripheral blood by flow cytometry. Cytometry (Communications in Clinical Cytometry), 26:113-120 (1996).
Yang et al. Tyrosine kinase inhibition in diffuse large B-cell lymphoma: molecular basis for antitumor activity and drug resistance of dasatinib. Leukemia 22(9):1755-1766 (2008) [E-pub Jul. 3, 2008].
Yasuhiro et al. ONO-WG-307, a Novel, Potent and Selective Inhibitor of Bruton's Tyrosine Kinase, in sustained inhibition of the Erk, Akt and PKD signaling pathways. 53rd American Society of Hematology Annual Meeting and Exposition, San Diego, CA, Poster #2021 (Dec. 10-13, 2011).
Zent et al. The Treatment of Recurrent/Refractory chronic Lymphocytic Leukemia/Small Lymphocytic Lymphoma (CLL) With Everolimus Results in Clinical Responses and Mobilization of CLL Cells Into the Circulation. Cancer 116(9):2201-2207 (2010).
Zhu et al. Calpain Inhibitor II Induces Caspase-dependent Apoptosis in Human Acute Lymphoblastic Leukemia and Non-Hodgkin's Lymphoma Cells as well as Some Solid Tumor Cells. Clin. Cancer Res. 6:2456-2463 (2000).
Advani et al. The BTK inhibitor PCI-32765 is highly active and well tolerated in patients (PTS) with relapsed/refractory B cell malignancies: final results from a phase I study, Ann. Oncol. 22(suppl 4): abstract 153 (2011).
Arnold et al. Pyrrolo[2,3-d]pyrimidines Containing an Extended 5-Substituent as Potent and Selective Inhibitors of lck 1. Bioorg. Med. Chem. Ltrs. 10:2167-2170 (2000).
Banker et al. Modern Pharmaceutics, 3ed., Marcel Dekker, New York 1996, p. 596.
Browning. B cells move to centre stage: novel opportunities for autoimmune disease treatment. Nature Reviews/Drug Discovery 5:564-576 (Jul. 2006).
Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).
Byrd et al. Entering the era of targeted therapy for chronic lymphocytic leukemia: impact on the practicing clinician. J. Clinical Oncology (Jul. 21, 2014) (pii: JCO.2014.55.8262).
Chang et al. The Bruton tyrosine kinase inhibitor PCI-32765 ameliorates autoimmune arthritis by inhibition of multiple effector cells. Arthritis Research & Therapy, 13:R115 (2011).
Cohen et al. Structural Bioinformatics-Based Design of Selective, Irreversible Kinase Inhibitors. Science 308:1318-1321 (May 27, 2005).
Co-pending U.S. Appl. No. 14/417,097, filed Jan. 23, 2015.
Co-pending U.S. Appl. No. 14/613,309, filed Feb. 3, 2015.
Czuczman et al. Rituximab in combination with fludarabine chemotherapy in low-grade or follicular lymphoma. J. Clin. Oncol. 23(4):694-704 (Feb. 1, 2005).
Desiderio. Role of Btk in B cell development and signaling. Curr. Op. in Immunology 1997, 9:534-540.
Dorwald. A. Side Reactions in Organic Synthesis, Wiley:VCH, Weinheim p. IX of Preface, Wiley-VCH Verlag GmbH & Co. KGaA (2005).
Fabian et al. A small molecule-kinase interaction map for clinical kinase inhibitors. Nature Biotechnology, 23(3): 329-336 (2005).
Fisher et al. Prolonged disease-free survival in Hodgkin's disease with MOPP reinduction after first relapse. Ann. Intern. Med., 90(5):761-763 (1979).
Fowler et al. The Bruton's tyrosine kinase inhibitor ibrutinib (PCI-32765) is active and tolerated in relapsed follicular lymphoma. 54th American Society of Hematology Annual Meeting and Exposition, Atlanta, GA, Abstract 156 (Dec. 8-11, 2012).
Fruman. Xid-like Phenotypes: A B Cell Signalosome Takes Shape. Immunity 13:1-3 (Jul. 2000).
Ghia. Ibrutinib: better combined with other drugs? Lancet 15:1043-1044 (2014).
Gold. To make antibodies or not:signaling by the B-cell antigen receptor. Trends in Pharmacological Sciences, 23(7):316-324 (Jul. 2002).
Hantschel et al. Systematic profiling and novel targets of the Bcr-Abl kinase inhibitors imatinib, nilotinib and dasatinib. Blood 110(11, Part 2):207B (2007) & 49th Annual Meeting of the American-Society-of-Hematology; Atlanta, Ga, USA; Dec. 8-11, 2007.
Herman et al. Bruton tyrosine kinase represents a promising therapeutic target for treatment of chronic lymphocytic leukemia and is effectively targeted by PCI-32765. Blood (Epub Mar. 21, 2011), 117(23):6287-6296 (Jun. 2011).
Hiddeman et al. Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group. Blood (Epub Aug. 25, 2005) 106(12):3725-3732 (Dec. 2005).
Horwood et al. Bruton's Tyrosin Kinase Is Required for Lipopolysaccharide-induced Tumor Necrosis Factor α Production. J. Exp. Med. 197(12):1603-1611 (Jun. 2003).
http://www.uspto.gov/web/offices/pac/dapp/1pecba.htm#7, last accessed Feb. 16, 2011.
Iwaki et al. Btk Plays a Crucial Role in the Amplification of FcεRI-mediated Mast Cell Activation by Kit. J. Biol. Chem. 280(48):40261-40270 (Dec. 2, 2005).
Jefferies et al. Bruton's Tyrosine Kinase Is a Toll/Interleukin-1 Receptor Domain-binding Protein That Participates in Nuclear Factor κB Activation by Toll-like Receptor 4. J. Biol. Chem. 278:26258-26264 (2003).
Kawakami et al. Terreic acid, a quinone epoxide inhibitor of Bruton's tyrosine kinase. PNAS USA 96:2227-2232 (1999).
Kuppers. Mechanisms of B-cell lymphoma pathogenesis. Nature Reviews/Cancer 5:251-262 (2005).
Kurosaki. Functional dissection of BCR signaling pathways. Curr. Op. Imm. 12:276-281 (2000).
Kushner et al. Pharmacological uses and perspective of heavy water and deuterated compounds. Canadian Journal of Physiology and Pharmacology 77(2):79-88 (1999).
Liu et al. Structural Basis for selective inhibition of Src family kinases by PPI. Chemistry and Biology 6:671-678, in particular table 1, p. 671 (1999).

(56) References Cited

OTHER PUBLICATIONS

Luskova et al. Modulation of the Fce Receptor I Signaling by Tyrosin Kinase Inhibitors: Search for Therapeutic Targets of Inflammatory and Allergy Diseases. Curr. Pharmaceutical Design 10:1727-1737 (2004).
Mahajan et al. Rational Design and Synthesis of a Novel Anti-leukemic Agent Targeting Bruton's Tyrosine Kinase (BTK), LFM-A13 [α-Cyano-β-Methyl-N-(2,5-Dibromophenyl)Propenamide]. J. of Biol. Chem. 274(14):9587-9599 (1999).
Mangla et al. Pleiotropic consequences of Bruton tyrosin kinase deficiency in myeloid lineages lead to poor inflammatory responses. Blood 104(4):1191-1197 (2004).
Merged Markush Service Search, Jun. 27, 2005.
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Oligino et al. Targeting B cells for the treatment of rheumatoid arthritis. Arthritis Res. Ther., 5(Suppl.4):S7-S11 (2002).
Pan et al. Discovery of Selective Irreversible Inhibitors for Bruton's Tyrosine Kinase, ChemMedChem. 2:58-61 (2007).
PCT/US2006/49626 International Preliminary Report on Patentability Search Report dated Mar. 24, 2009.
PCT/US2006/49626 International Search Report dated Apr. 9, 2008.
PCT/US2013/051741 International Preliminary Report on Patentability dated Jan. 27, 2015.
PCT/US2013/051741 International Search Report and Written Opinion dated Jan. 7, 2014.
Peterson et al. Prolonged single-agent versus combination chemotherapy in indolent follicular lymphomas: a study of the cancer and leukemia group. Br. J. Clin. Oncol., 21(1):5-15 (Jan. 1, 2003).
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Quek et al. A role for Bruton's tyrosine kinase (Btk) in platelet activation by collagen. Curr. Biol. 8(20) :1137-1140 (1998).
Sada et al. Protein-Tyrosine Kinases and Adaptor Proteins in FceRI-Mediated Signaling in Mast Cells. Curr. Mol. Med. 3(1):85-94 (2003).
Schaeffer et al. Tec family kinases in lymphocyte signaling and function. Curr. Op. Imm. 12:282-288 (2000).
Science IP CAS Search, Mar. 16, 2006.
Science IP CAS Search, Sep. 5, 2006.
Shaffer et al. Lymphoid malignancies: the dark side of B-cell differentiation. Nature Reviews/Immunology 2:920-932 (2002).
Shah et al. Ibrutinib for the treatment of mantle cell lymphoma. Expert Rev. Hematol. 7(5):521-531 (2014) (Epub Aug. 27, 2014).
Smaill et al. Tyrosine Kinase Inhibitors. 15. 4-(Phenylamino)quinazoline and 4-(Phenylamino)prido[d]pyrimidine Acrylamides as Irreversible Inhibitors of the ATP Binding Site of the Epidermal Growth Factor Receptor. J. Med. Chem. 42(10):1803-1815 (1999).
Smith et al. The Tec family of cytoplasmic tyrosine kinases: mammalian Btk, Bmx, Itk, Tec, Txk and homologs in other species. BioEssays 23:436-446 (2001).
Smolen et al. Therapeutic Strategies for Rheumatoid Arthritis. Nature Reviews 2:473-488 (2003).
Tinmouth et al. Fludarabine in alkylator-resistant follicular non-Hodgkin's lymphoma. Leuk. Lymphoma 41(1-2):137-145 (2001).
Uckun et al. Bruton's tyrosine kinase as a molecular target in treatment of leukemias and lymphomas as well as inflammatory disorders and autoimmunity. Expert Opinion Ther. Patents 20(11):4157-1470 (2010).
Uckun et al. Bruton's Tyrosine Kinase (BTK) as a Dual-Function Regulator of Apoptosis. Biochem. Pharmacology 56:683-691 (1998).
Uckun et al. BTK as a Mediator of Radiation-Induced Apoptosis in DT-40 Lymphoma B Cells. Science 273(5278):1096-1100 (1996).
Uckun et al. In Vivo Pharmacokinetic Features, Toxicity Profile, and Chemosensitizing Activity of α-Cyano-β-hydroxy-β-methyl-N-(2,5-dibromophenyl)propenamide (LFM-A13), a Novel Antileukemic Agent Targeting Bruton's Tyrosine Kinase. Clin. Cancer Res. 8:1224-1233 (2002).
Uckun et al. The Anti-leukemic Bruton's Tyrosin Kinase Inhibitor α-cyano-β-hydroxy-β-mehyl-N-(2,5-dibromophenyl)Propenamide (LFM-A13)Prevents Fatal Thromboembolism. Leuk. Lymphoma 44(9):1569-1577 (2003).
U.S. Appl. No. 14/079,508 Office Action dated Dec. 15, 2014.
U.S. Appl. No. 11/617,645 Final Office Action dated Oct. 16, 2008.
U.S. Appl. No. 11/617,645 Notice of Allowance dated Feb. 9, 2009.
U.S. Appl. No. 11/617,645 Office Action dated Jan. 24, 2008.
U.S. Appl. No. 11/617,645 Office Action dated May 13, 2008.
U.S. Appl. No. 11/692,870 Final Office Action dated Aug. 19, 2009.
U.S. Appl. No. 11/692,870 Office Action dated Jan. 26, 2009.
U.S. Appl. No. 12/356,498 Final Office Action dated Jul. 8, 2011.
U.S. Appl. No. 12/356,498 Office Action dated Apr. 14, 2011.
U.S. Appl. No. 12/499,002 Final Office Action dated Dec. 14, 2012.
U.S. Appl. No. 12/499,002 Final Office Action dated Oct. 25, 2011.
U.S. Appl. No. 12/499,002 Office Action dated Mar. 3, 2011.
U.S. Appl. No. 12/499,002 Office Action dated Jun. 5, 2012.
U.S. Appl. No. 12/499,005 Office Action dated Feb. 17, 2011.
U.S. Appl. No. 12/499,008 Office Action dated Jul. 19, 2011.
U.S. Appl. No. 12/499,008 Office Action dated Mar. 9, 2011.
U.S. Appl. No. 12/727,703 Final Office Action dated Jul. 19, 2011.
U.S. Appl. No. 12/727,703 Office Action dated Mar. 3, 2011.
U.S. Appl. No. 12/887,428 Office Action dated Apr. 20, 2011.
U.S. Appl. No. 12/907,759 Final Office Action dated Nov. 8, 2013.
U.S. Appl. No. 12/907,759 Office Action dated Aug. 13, 2013.
U.S. Appl. No. 12/907,759 Office Action dated Dec. 31, 2013.
U.S. Appl. No. 12/907,759 Office Action dated Jul. 10, 2014.
U.S. Appl. No. 13/011,258 Office Action dated Nov. 22, 2011.
U.S. Appl. No. 13/162,449 Office Action dated Feb. 9, 2012.
U.S. Appl. No. 13/249,066 Final Office Action dated May 15, 2013.
U.S. Appl. No. 13/249,066 Office Action dated Dec. 11, 2013.
U.S. Appl. No. 13/249,066 Office Action dated Nov. 27, 2012.
U.S. Appl. No. 13/312,606 Final Office Action dated Apr. 5, 2013.
U.S. Appl. No. 13/312,606 Office Action dated Sep. 19, 2012.
U.S. Appl. No. 13/328,718 Final Office Action dated Dec. 27, 2012.
U.S. Appl. No. 13/328,718 Office Action dated Jul. 3, 2012.
U.S. Appl. No. 13/335,719 Final Office Action dated Nov. 8, 2013.
U.S. Appl. No. 13/335,719 Office Action dated Jul. 31, 2013.
U.S. Appl. No. 13/340,409 Final Office Action dated Nov. 12, 2013.
U.S. Appl. No. 13/340,409 Office Action dated Jul. 19, 2013.
U.S. Appl. No. 13/340,556 Office Action dated Jul. 31, 2013.
U.S. Appl. No. 13/361,726 Office Action dated Jul. 18, 2013.
U.S. Appl. No. 13/361,733 Notice of Allowance dated Nov. 14, 2012.
U.S. Appl. No. 13/361,733 Office Action dated Jul. 6, 2012.
U.S. Appl. No. 13/450,158 Non-Final Office Action dated Oct. 31, 2013.
U.S. Appl. No. 13/472,292 Office Action dated Mar. 13, 2013.
U.S. Appl. No. 13/479,053 Office Action dated Sep. 6, 2013.
U.S. Appl. No. 13/526,161 Final Office Action dated May 15, 2013.
U.S. Appl. No. 13/526,161 Office Action dated Nov. 27, 2012.
U.S. Appl. No. 13/526,161 Office Action dated Aug. 1, 2013.
U.S. Appl. No. 13/526,163 Final Office Action dated May 15, 2013.
U.S. Appl. No. 13/526,163 Office Action dated Aug. 2, 2013.
U.S. Appl. No. 13/526,163 Office Action dated Nov. 28, 2012.
U.S. Appl. No. 13/542,440 Non-Final Office Action dated Oct. 31, 2013.
U.S. Appl. No. 13/542,440 Office Action dated Jan. 7, 2014.
U.S. Appl. No. 13/654,173 Office Action dated Apr. 7, 2014.
U.S. Appl. No. 13/849,399 Office Action dated Aug. 4, 2014.
U.S. Appl. No. 13/849,399 Office Action dated Jul. 23, 2014.
U.S. Appl. No. 13/890,498 Non-Final Office Action dated Mar. 6, 2015.
U.S. Appl. No. 13/890,498 Office Action dated Aug. 19, 2014.
U.S. Appl. No. 14/033,344 Non-Final Office Action dated Dec. 10, 2014.
U.S. Appl. No. 14/073,543 Office Action dated Dec. 15, 2014.
U.S. Appl. No. 14/073,594 Office Action dated Dec. 15, 2014.

(56) References Cited

OTHER PUBLICATIONS

U.S. Appl. No. 14/080,640 Non-Final Office Action dated Feb. 24, 2015.
U.S. Appl. No. 14/080,640 Office Action dated Dec. 31, 2014.
U.S. Appl. No. 14/080,649 Office Action dated Feb. 5, 2015.
U.S. Appl. No. 14/152,886 Non-Final Office Action dated Apr. 23, 2015.
U.S. Appl. No. 14/156,247 Non-Final Office Action dated May 1, 2015.
U.S. Appl. No. 148/340,483 Office Action dated May 5, 2015.
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al. Crystalline Solids, Advanced Drug Delivery Reviews, 48:3-26 (2001).
Witzig et al. Lenalidomid oral monotherapy produces durable responses in relapsed or refractory indolent non-Hodgkin's lymphoma. J. Clin. Oncol. 27:5404-5409 (Epub Oct. 5, 2009).
Wolff. Burger's Medicinal Chemistry and Drug Discovery. 5th Ed. Part 1, pp. 975-977 (1995).
Woyach et al. Resistance mechanisms for the Bruton's tyrosine kinase inhibitor ibrutinib. N Engl J Med 370(24):2286-2294 (2014).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents. J. Pharma. and Exp. Therapeutics 306(3):1174-1181 (2003).
D'Cruz et al. Novel Bruton's tyrosine kinase inhibitors currently in development. OncoTargets and Therapy 6:161-176 (2013).
PCT/US2015/21871 International Search Report and Written Opinion dated Jul. 8, 2015.
Stead et al. Concise synthesis of (+/-)-Cytisine via lithiation of N-Boc-bispidine. Organic Letters 7(20):4459-4462 (2005).
U.S. Appl. No. 14/073,594 Final Office Action dated Jul. 1, 2015.
U.S. Appl. No. 14/080,640 Final Office Action dated May 13, 2015.
U.S. Appl. No. 14/080,649 Final Office Action dated May 21 2015.
Burger J.A., "The Bruton's Tyrosine Kinase Inhibitor, PCI-32765, Is Well Tolerated and Demonstrates Promising Clinical Activity in Chronic Lymphocytic Leukemia (CLL) and Small Lymphocytic Lymphoma (SLL): An Update on Ongoing Phase 1 Studies," Blood, Nov. 19, 2010, vol. 116 (21), p. 57.
Byrd J.C., et al., "Three-year follow-up of treatment-naïve and previously treated patients with CLL and SLL receiving single-agent ibrutinib", Blood, Apr. 16, 2015, vol. 125 (16), pp. 2497-2506.
Chang et al., "Use of tumor genomic profiling to reveal mechanisms of resistance to the BTK inhibitor ibrutinib in chronic lymphocytic leukemia (CLL)," Journal of Clinical Oncology, 2013, vol. 31, No. 15, May 20 Suppl,. Abstract No. 7014.
International Preliminary Report on Patentability for Application No. PCT/US15/21871, dated Sep. 29, 2016, 10 pages.
Iqbal et al., on pp. 2-4 (Molecular Biology International, 2014, Article ID 852748, 9 pages.
Marcotte et al, Structures of human Bruton's tyrosine kinase in active and inactive conformations suggest a mechanism of activation for TEC family kinases., Protein Science. 2010, 19:429-439.
Non-Final Office Action for U.S. Appl. No. 14/793366, dated Nov. 1, 2016.
Pollyea D.A., et al., "A Phase I Dose Escalation Study of the Btk Inhibitor PCI-32765 in Replace and Refractory B Cell Non-Hodgkin Lymphoma and Use of a Novel Fluorescent Probe Pharmacodynamic Assay," Blood, 2009, vol. 114, Abstract 3713.
PRNewsire "U.S. FDA grants regular (full) approval for Imbruvica for two indications," Jul. 28, 2014.
U.S. Appl. No. 14/091,196 Final Office Action dated Jan. 29, 2016.
Adimoolam et al. HDAC inhibitor PCI-24781 decreases RAD51 expression and inhibits homologous recombination. PNAS 104 (49):19482-19487 (2007).
Almo et al., Considerations for combined immune checkpoint modulation and radiation treatment, Radiat Res, 182(2): 230-238 (2014).
Anonymous: "Ibrutinib/Rituximab combination leads to high response rate among patient with CLL," The Asco Post (2013).
Anonymous: "NCT01217749 on Apr. 16, 2012: Clinical Trials.gov Archive," Apr. 16, 2012 (Apr. 16, 2012), XP055260251, Retrieved from the Internet: URL:https://clinicaltrials.gov/archive/NCT01217749/2012_04_16.
Ansell, "Two targets for the price of one," Blood 122(15): 2529-2531 (Oct. 10, 2013).
Arkin et al. HER-2-directed, small-molecule antagonists. Curr Opin Investig Drugs. 2008;9(12):1264-1276. (saved on H drive and filesite).
Asrani et al. The HER2- and heregulin β1 (HRG)-inducible TNFR superfamily member Fn14 promotes HRG-driven breast cancer cell migration, invasion, and MMP9 expression. Mol Cancer Res. Apr. 2013;11(4):393-404. doi: 10.1158/1541-7786.MCR-12-0542. Epub Feb. 1, 2013.
Atsukawa et al, "Ribavirin downmodulates inducible costimulator on Cd4+ T cells and their interleukin-10 secretino to assist in hepatitis C virus clearance," J Gastoenterology and Hepatology 27:823-831 (2012).
Axelrod, et al., "Combinatorial Drug Screening Identified Synergistic Co-Targeting of Bruton's Tyrosine Kinase and the Proteasome in Mantle Cell Lymphoma," Leukemia, 28(2): 407-410 (Feb. 1, 2014).
Baghdadi et al., "The impact of the TIM gene family on tumor immunity and immunosuppression," Cell Mol Immunol, 11(1): 41-48 (2014).
Balakrishnan et al. "AT-101 induces apoptosis in CLL B cells and overcomes stromal cell-mediated Mcl-1 induction and drug resistance," Blood, Oct. 3, 2008 (Oct. 3, 2008), vol. 113, No. 1, pp. 149-153.
Barany, "Genetic Disease Detection and DNA Amplification Using Cloned Thermostable Ligase," Proc. Natl. Acad. Sci. USA, 88:189-193 (1991).
Bauzon et al., "Armed therapeutic viruses—a disruptive therapy on the horizon of cancer immunotherapy," Front Immunol, 5: 74 (2014).
Bhagat et al., "Abstract 2570: IMO-8400, a Selective Antagonist of TLRs 7, 8 and 9, Inhibits MYD88 L265P Mutation-driven Signaling and Cell Survival: A Potential Novel Approach for Treatment of B-cell Lymphomas Harboring MYd88 L265P Mutation," Cancer Res, 74: 2570 Abstract (2014).
Bhalla et al. PCI-24781 induces caspase and reactive oxygen species-dependent apoptosis through NF-kappaB mechanisms and is synergistic with bortezomib in lymphoma cells. Clin Cancer Res 15:3354-3365 (2009).
Biocompare, "Th1 and Th2 Balance, Regulation, and Involvement in Disease," http://www.biocompare.com/Application-Notes/43518-Thi -And-Th1-Balance-Regulation-And-Involvement-In-Disease (Apr. 24, 2006).
Bowen et al., "Adaptive Immune Responses in Acute and Chronic Hepatitis C Virus Infection," Nature 436(7053):946-852 (2005).
Brahmer et al., "Safety and activity of anti-PD-L1 antibody in patients with advanced cancer," N Engl J Med, 366(26): 2455-2465 (2012).
Brown et al., "PCI-32765, the first BTK (Bruton's Tyrosine Kinase) inhibitor in clinical trials," Curr Hematol Malig Rep, 8(1): 1-6 (2013).
Burger et al. The Btk Inhibitor Inbrutinib (PCI-32765) in Combination with Rituximab Is Well Tollerated and Displays Profound Activity in High-Risk Chronic Lyphocytic Leukemia (CLL) Patients. Blood (ASH Annual Meeing Abstracts).120:Abstract 187 (2012).
Burger et al., "Ibrutinib as Initial Therapy for Patients with Chronic Lymphocytic Leukemia," New Engl J Med, 373(25): 2425-2437 (2015).
Callahan et al., "At the bedside: CTLA-4- and PD-1-blocking antibodies in cancer immunotherapy," J Leukoc Biol, 94(1): 41-53 (2013).

(56) References Cited

OTHER PUBLICATIONS

Calpe et al., "ZAP-70 Enhances Migration of Malignant B Lymphocytes Toward CCL21 by Inducing CCR7 Expression via IgM-ERK1/2 Activation," Blood, 118(16): 4401-4410 (2011).
Celgene Corporation: "Pomalyst (pomalidomide) capsules for oral use", Feb. 1, 2013 (Feb. 1, 2013), XP002764262, Retrieved from the Internet: URL:http://www.accessdata.fda.gov/drugsatf da docs/labe1/2013/204026lbl.pdf [retrieved on Nov. 15, 2016].
Ceribelli, M et al. Blockade of oncogenic IKB kinase activity in diffuse large B-celllymphom by bromodomain and extraterminal domain protein inhibitors. Proceedings of the National Academy of Sciences. Published online: Jul. 21, 2014. vol. 111. No. 31. pp. 11365-11370.
Chaturvedi et al. "Mutant IDH1 promotes leukemogenesis in vivo and can be specifically targeted in human AML," Blood, Aug. 16, 2013 (Aug. 16, 2013), vol. 122, No. 16, pp. 2877-2887.
Chen et al. "Pim kinase inhibitor, SGI-1776, induces apoptosis in chronic lymphocytic leukemia cells," Blood, Sep. 4, 2009 (Sep. 4, 2009), vol. 114, No. 19, pp. 4150-4157.
Chiron et al., "Cell-Cycle Reprogramming for PI3K Inhibition Overrides a Relapse-Specific C481S BTK Mutation Revealed by Longitudinal Functional Genomics in Mantle Cell Lymphoma," Cancer Discov, 4(9): 1022-1035 (2014).
Choi et al., "Inhibitors of B-cell receptor signaling for patients with B-cell malignancies," Cancer J, 18(5):404-410 (2012).
Chothia et al., "Canonical Structures for the Hypervariable Regions of Immunoglobulins," J. Mol. Biol., 196(4):901-917 (1987).
Clark et al., "The Role of Ribavirin in Direct Acting Antiviral Drug Regimens for Chronic Hepatitis C," Liver Int. 32(01)103-107 (2012).
Clinical.Trials.gov: "Study of Ibrutinib in Combination With Pomalidomide and Dexamethasone in Subjects With Relapsed I Refractory Multiple Myeloma", Nov. 9, 2016 (Nov. 9, 2016), Retrieved from the Internet: URL:https://clinicaltrials.gov/ct2/show/NCT02548962 [retrieved on Nov. 1, 2016].
Combination treatment of the Bruton's tyrosine kinase inhibitor ibrutinib and carfilzomib in patients with relapsed or relapsed and refractory multiple myeloma: initial results from a multicenter phase 1/2b study. NCT01962792 (2015).
Cummings et al., "Critical Role for Phosphoinositide 3-Kinase Gamma in Parasite Invasion and Disease Progression of Cutaneous Leishmaniasis," PNAS USA, 109:1251-1256 (2012).
Dasmahapatra, et al., "The Bruton Tyrosine Kinase (BTK) Inhibitor PCI-32765 Synergistically Increases Proteasome Inhibitor Activity in Diffuse large-B cell lymphoma (DLBCL) and Mantle Cell lymphoma (MCL) Cells Sensitive or Resistant to Bortezomib," British Journal of Haematology, 161(1): 43-56 (Jan. 30, 2013).
Davids et al., "The BCL-2-specific BH3-mimetic ABT-199 (GDC-0199) is active and well-tolerated in patients with relapsed non-Hodgkin lymphoma: interim results of a phase I study," Blood, 120(21): Abstract No. 304 (2012).
Delgado, Md et al. Myc Roles in Hematopoiesis and Leukemia. Genes & Cancer. 2010. vol. 1. No. 6. pp. 605-616; abstract; p. 609,Jeft column, 3rd paragraph; p. 610, righ column, 2nd paragraph; p. 612, middle column, 3rd paragraph, right column, 1st paragraph.
Dixon, "Evaluation of the CASP2 docking section," Proteins, Suppl 1: 198-204 (1997).
Dohner et al., "Genomic Aberrations and Survival in Chronic Lymphocytic Leukemia," The New England Journal of Medicine, pp. 1910-1916 (2000).
Dolganiuc et al., "T Cells with Regulatory Activity in Hepatitis C Virus Infection: What We Know and What We Don't," J Leukoc Biol. 84(3): 614-622 (2008).
Dubovsky et al, "Ibrutinib Is an Irreversible Molecular Inhibitor of Interleukin-2 Inducible Kinase: Expanding Therapeutic Potential and Modulating a th1 Selective Pressure in CD4 T-Cells," 54th ASH Annual Meeting and Exposition, Blood, 120:775 (2012).
Dubovsky et al., "Epigenetic Repolarization of T Lymphocytes from Chronic Lymphocytic Leukemia Patients Using 5-aza-2'-deoxycytidine," Leukemia Research 35:1193-1199 (2011).
Dubovsky et al., "Ibrutinib is an irreversible molecular inhibitor of ITK driving a Th1-selective pressure in T lymphocytes," Blood, 122(15): 2539-2549 (2013).
Dubovsky et al., "Restoring the Functional Immunogenicity of Chronic Lymphocytic Leukemia Using Epigenetic Modifiers," Leukemia Research 35(3):394-404 (2011).
Dy et al. Understanding, recognizing, and managing toxicities of targeted anticancer therapies. CA: a cancer Journal for clinicians. 63(4):249-279 (Epub May 2013).
EA200901313 Notification of Office Action dated Oct. 31, 2011.
EA201000599 Search Report dated Nov. 15, 2010.
Elias et al. BTK Inhibitor Ibrutinib Inhibits Breast Cancer Growth by Inhibiting ErbB Kinases. Mol Cancer Ther. 2013;12:C258. (not available on pubmed).
Emens et al., "Breast cancer immunobiology driving immunotherapy: vaccines and immune checkpoint blockade," Expert Rev Anticancer Ther, 12(12): 1597-1611 (2012).
EP 06850039 Supplemental Search Report dated Feb. 9, 2010.
EP 06850386.1 Search Report and Written Opinion dated Sep. 10, 2010.
EP 08744513 Supplementary Search Report dated Mar. 11, 2010.
EP 08744513.6 Examination Report dated Jan. 16, 2013.
EP 09798770.5 Search Report and Written Opinion dated Oct. 28, 2011.
EP 10155834.4 Search Report dated May 19, 2010.
EP 10823966 Supplementary European Search Report dated Oct. 17, 2011.
EP 10823966.6 Written Opinion dated Dec. 6, 2011.
EP 12151943.3 Examination Report dated Feb. 5, 2013.
EP 12151943.3 Search Report and Written Opinion dated Mar. 13, 2012.
EP 12166295.1 Search Report and Written Opinion dated Nov. 6, 2012.
EP 12166296.9 Search Report and Written Opinion dated Nov. 8, 2012.
EP 12166298.5 Search Report and Written Opinion dated Nov. 7, 2012.
EP 12166300.9 Search Report and Written Opinion dated Oct. 31, 2012.
EP 12166301.7 Search Report and Written Opinion dated Nov. 6, 2012.
EP 12166302.5 Search Report and Written Opinion dated Nov. 6, 2012.
EP 12166305.8 Examination Report dated Dec. 3, 2013.
EP 12166305.8 Search Report and Written Opinion dated Nov. 6, 2012.
EP 12166306.6 Search Report and Written Opinion dated Nov. 8, 2012.
EP 12172840.6 Search Report and Written Opinion dated Dec. 12, 2012.
EP 12172841.4 Search Report and Written Opinion dated Jan. 2, 2013.
EP 12172842.2 Extended Search Report dated May 14, 2013.
EP 12172842.2 Partial Search Report dated Jan. 24, 2013.
EP 12172843.0 Search Report and Written Opinion dated Jan. 18, 2013.
Ezell S.A., et al., "Synergistic Induction of Apoptosis by Combination of BTK and Dual mTORC1/2 Inhibitors in Diffuse Large B Cell Lymphoma," Oncotarget, 2014, vol. 5 (13), pp. 4990-5001.
Fallahi et al., "Cytokines and HCV-Related Disorders," Clinical and Developmental Immunology. 2012. Article IDs 468102. 10 pgs.
Federal Register, vol. 66, No. 4, pp. 1099-1111, Jan. 5, 2001.
Flynn et al., "Maintenance of TH1 HCV-Specific Responses in Individuals with Acute HCV who Achieve Sustained Virological Clearance After Treatment," Centre for Biomedical Research. Doi: 10.111/jgh.12265 (no date available).
Fontan et al., "Targeting Lymphomas Through MALT1 Inhibition," Oncotarget, 3(12): 1493-1494 (2012).
Fonte et al., "In vitro sensitivity of CLL cells to fludarabine may be modulated by the stimulation of Toll-like receptors," Clin Cancer Res 19:367-379 (2013).

(56) References Cited

OTHER PUBLICATIONS

Fowell et al., "Impaired NFATc Translocation and Failure of Th2 Development in Itk-Deficient CD4+ T Cells," Immunity 11:399-409 (1999).
Fowler et al. The Btk Inhibitor, PCI-32765, Induces Durable Responses with Minimal Toxicity in Patients with Relapsed/Refractory B-Cell Malignancies: Results From a Phase 1 Study. Blood (ASH Annual Meeting) 116 (21), p. 425:Abstract 964 (2010).
Fritsche et al., "National Academy of Clinical Biochemistry Guidelines for the Use of Tumor Markers in Bladder Cancer," NACB: Practice Guidelines and Recommendations for Use of Tumor Markers in the Clinic Bladder Cancer (3H)1. (Oct. 30, 2013). http://www.aacc.org/SiteCollectionDocuments/NACB/LMPG/tumor/chp3h_bladder.pdf.
Fujimoto et al., "Peripheral Pulmonary Carcinomas Evaluated with Dynamic MR Imaging: Correlation with Tumor Vascularity and Prognosis," Radiology, 227:786-793 (2003).
Fundamental Immunology p. 242 (William E. Paul, M.D. ed., 3d ed; 1993)].
Gad et al., "Distinct Immunoregulatory Cytokine Pattern in Egyptian Patients with Occult Hepatitis C Infection and Unexplained Persistently Elevated Liver Transaminases," Asian J. Transfus Sci. 6(1): 24-28 (2012).
Galli et al., "Evoking durable anti-cancer responses with blocking antibodies to PD-1 and PD-L1," Transl Cancer Res, 1(4): 287-289 (2012).
Goding et al., "Combination of adoptive cell transfer, anti-PD-L1 and anti-LAG-3 antibodies for the treatment of recurrent tumors," OncoImmunology 2(8): e25050 (2013).
Goggins, "Markers of Pancreatic Cancer: Working Toward Early Detection," Clin. Cancer Res. 17(4):635-7 (2011).
Gomez-Rodriguez et al, "Tec Family Kinases Itk and Rlk/Txk in T Lymphocytes Cross-Regulation of Cytokine Production and T-Cell Fates," FEBS Journal 278(12):1980-1989 (2011).
Grabinski N., et al., "Ibrutinib (ImbruvicaTM) Potently Inhibits ErbB Receptor Phosphorylation and Cell Viability of Erbb2-Positive Breast Cancer Cells," Investigational New Drugs, Aug. 2014, vol. 32 (6), pp. 1096-1104.
Grosso et al., CTLA-4 blockade in tumor models: an overview of preclinical and translational research, Cancer Immun, 13: 5 (2013).
Grzywnowicz et al., "Expression of programmed death 1 ligand in different compartments of chronic lymphocytic leukemia," PLoS One, 7(4):e35178, pp. 1-8 (2012).
Guatelli et al., "Isothermal, in Vitro Amplification of Nucleic Acids by a Multienzyme Reaction Modeled After Retroviral Replication," Proc. Natl. Acad. Sci. USA, 87(5):1874-1878 (1990).
Guinn et al., "miR-155 expression is associated with chemoimmunotherapy outcome and is modulated by Bruton's tyrosine kinase inhibition with Ibrutinib," Leukemia 29(5): 1210-1213 (2015).
Guo, "Molecular Characteristic of CTA056, a Novel Interleukin-2-Inducible T-Cell Kinase Inhibitor that Selectively Target Malignat T Cell and Modulate Oncomirs," Molecular Pharmacology 82:938-947 (Aug. 2012).
Gupta et al., "Inhibition of Histone Deacetylase Overcomes Rapamycin-mediated Resistance in Diffuse Large B-cell Lymphoma by Inhibiting Akt Signaling Through MTOC2," Blood, 114:2926-2935 (2009).
Hahtola et al., "Th1 Response and Cytotoxicity Genes are Down-Regulated in Cutaneous T-Cell Lymphoma," Clin Cancer Res. 12(16):4812-4821 (2006).
Hantschel et al. The Btk Tyrosine Kinase is a Major Target of the Bcr-Abl Inhibitor Dasatinib. PNAS 104(33):13283-13288 (2007).
Herman et al. "Ibrutinib inhibits BCR and NF-KB signaling and reduces tumor proliferation in tissue-resident cells of patients with CLL," Blood. Mar. 21, 2014 (Mar. 21, 2014 ), vol. 123, pp. 3286-3295.
Horning et al., the natural history of initially untreated low-grade non-Hodgkin's lymphomas, (1984) N. Engl. J. Med. 311:1471-1475.
Hurrell et al. The in vitro influences of epidermal growth factor and heregulin-β1 on the efficacy of trastuzumab used in Her-2 positive breast adenocarcinoma. Cancer Cell Int. Oct. 11, 2013;13(1):97. doi: 10.1186/1475-2867-13-97.
IDW00201201693 Office Action dated Apr. 20, 2015.
Igietseme et al., "Suppression of Endogenous IL-10 Gene Expression in Dendritic Cells Enhances Antigen Presentation for Specific Th1 Induction: Potential for Cellular Vaccine Development," J Immunol, 164: 4212-4219 (2000).
Inhibitory effects of the BTK inhibitor, ibrutinib, on HER2-amplified breast cancer growth, cell cycle progression, and clonogenicity—Poster.
International Preliminary Report on Patentability for PCT/US2013/068132 dated May 5, 2015.
International Preliminary Report published Oct. 30, 2007 on Patentability for PCT/IB2005/002350, filed Apr. 28, 2005.
International Search Report and Written Opinion for International Patent Application No. PCT/US15/61091 dated Mar. 11, 2016.
International Search Report and Written Opinion for International Patent Application No. PCT/US16/15697 dated Apr. 22, 2016.
International Search Report and Written Opinion for International Patent Application No. PCT/US16/41550 dated Nov. 15, 2016.
International Search Report and Written Opinion for International Patent Application No. PCT/US16/63085 dated May 22, 2017.
International Search Report and Written Opinion for International Patent Application No. PCT/US2014/058132 dated Jan. 14, 2015.
International Search Report and Written Opinion for International Patent Application No. PCT/US2015/051034 dated Dec. 18, 2015.
International Search Report published Jan. 25, 2007 for PCT/IB2005/002350, filed Apr. 28, 2005.
Iriyama et al. "Clinical significance of genetic mutations of CD79B, CARD11, MYD88, and EZH2 genes in diffuse large B-cell-lymphoma patients," Dec. 10, 2011 (Dec. 10, 2011), 53rd ASH Annual Meeting, Abstract 2633, available at https://ash.confex.com/ash/2011/webprogram/Paper36650.html.
Jaglowski et al., "A Phase Ib/II Study Evaluating Activity and Tolerability of BTK Inhibitor PCI-32765 and Ofatumumab in Patients with Chronic Lymphocytic Leukemia/Small Lymphocytic Lymphoma (CLL/SLL) and related Diseases," J Clin Oncol, 30: Abstract 6508 (2012).
Jak et al., "CD40 Stimulation Sensitizes CLL Cells to Lysosomal Cell Death Induction by Type II Anti-CD20 mAb GA101," Blood, 118(19): 5178-5188 (2011).
Kabat et al., "Sequences of Proteins of Immunological Interest," NIH Publ. No. 91-3242, 1:647-669 (1991).
Kang et al., "Dynamic Analysis of Th1/Th2 Cytokine Concentration During Antiretroviral Therapy of HIV-1/HCV Co-Infected Patients," MCS Infectious Diseases 12:102-112 (2012).
Karanjawala et al., "New Markers of Pancreatic Cancer Identified Through Differential Gene Expression Analyses: Claudin 18 and Annexin A8," Am J. Surg. Pathol. 32(2):188-196 (2008).
Kathawala et al., "Masitinib Antagonizes ATP-Binding Cassette Subfamily C Member 10-Mediated Paclitaxel Resistance: A Preclinical Study," Mol Cancer Ther, 13(3): 714-723 (2014).
Kathawala et al., "The Small Molecule Tyrosine Kinase Inhibitor NVP-BHG712 Antagonizes ABCC10-mediated Paclitaxel Resistance: A Preclinical and Pharmacokinetic Study," Oncotarget, 6(1): 510-521 (2014).
Kaur et al., "Inhibitors of Interleukin-2 Inducible T-Cell Kinase as Potential Therapeutic Candidates for the Treatment of Various Inflammatory Disease Conditions," Eur J Pharm Sci 47(3):574-578 (2012).
Kawakami et al., "Regulation of Dendritic Cell Maturation and Function by Bruton's Tyrosine Kinase via IL-10 and Stat3," Proc Natl Acad Sci USA, 103(1): 153-158 (2006).
Keeton et al. "AZD1208, a potent and selective pan-Pim kinase inhibitor, demonstrates efficacy in preclinical models of acute myeloid leukemia," Blood, Dec. 20, 2013 (Dec. 20, 2013), vol. 123, No. 6, pp. 905-913.
Khan et al., "Circulating Biomarkers and their Possible Role in Pathogenesis of Chronic Hepatits B and C Viral Infections," Ind J Clin Biochem 46(2):161-168 (2011).

(56) References Cited

OTHER PUBLICATIONS

Kim et al. HRG-β1-driven ErbB3 signaling induces epithelial-mesenchymal transition in breast cancer cells. BMC Cancer. Aug. 12, 2013;13:383. doi: 10.1186/1471-2407-13-383.
Ko. Everyone's Guide to Cancer Therapy: How Cancer is Diagnosed, treated and Managed Day to Day. 3 pgs. (2009).
Kong et al., "Opportunistic Autoimmune Disorders Potentiated by Immune-Checkpoint Inhibitors Anti-CTLA-4 and Anti-PD-1," Front Immunol, 5(206): 1-8 (2014).
Kono, "Current status of cancer immunotherapy," J Stem Cells Regen med, 10(1): 8-13 (2014).
Kwoh et al., "Transcription-based amplification system and detection of amplified human immunodeficiency virus type 1 with a bead-based sandwich hybridization format," Proc. Natl. Acad. Sci. USA, 86:1173-1177 (1989).
Kyi et al., "Checkpoint blocking antibodies in cancer immunotherapy," FEBS Letters, 588(2):368-376 (2013).
Langhans et al., "Ribavirin Exerts Differential Effects on Function of Cd4+Th1, Th2, and Regulator T Cell Clones in Hepatitis C," PLOS One 7(7):e42094-42103 (2012).
Lapalombella et al., "Testrapanin CD37 Directly Mediates Transduction of Survival and Apoptotic Signals," Cancer Cell 21, 694-708 (2012).
Lau et al., "Mechanism of Action of Ribavirin in the Combination of Treatment of Chronic HCV Infection," Hepatology 35(5)1002-1009 (2002).
Lemery, "US Food and Drug Administration Approval: Ofatumumab for the Treatment of Patients with Chronic Lymphocytic Leukemia Refractory to Fludarabine and Alemtuzmab," Clinical Cancer Research pp. 4331-4338 (2010).
Lensink et al., "Docking and scoring protein complexes: CAPRI 3rd Edition," Proteins, 69(4):704-718 (2007).
Lester et al., "Interleukin 2-Inducible T Cell Kinase (ITK) Facilitates Efficient Egress of HIV-1 by Coordinating Gag Distribution and Actin Organization," Virology 436 (1): 235-243 (2013).
Liao et al., "Interleukin-2 at the Crossroads of Effector Responses, Tolerance, and Immunotherapy," Immunity 38(1):13-25 (2013).
Lim et al. Asymmetric syntheses of fused bicyclic lactams. Journal of Organic chemistry 66(26):9056-9062 (2001).
Lizardi et al., "Exponential Amplification of Recombinant-RNA Hybridization Probes," Bio/Technology, 6:1197-1202 (1988).
Lo et al., "Itk Inhibitors: A Patent Review," Expert Opin. The Patents 20(4):459-469 (2010).
Lopez et al. Combining PCI-24781, a Novel Histone Deacetylase Inhibitor, with Chemotherapy for the Treatment of Soft Tissue Sarcoma. Clin Cancer Res 15:1774-1775, 3472-3483 (2009).
Luban, "TRIM5 and the Regulation of HIV-1 Infectivity," Mol. Biol. Int. 2012:426840 (2012).
Mathews, et al., "High-Throughput Combinatorial Screening Identifies Drugs that Cooperate with Ibrutinib to Kill Activated B-cell-like diffuse large B-cell lymphoma cells," Proceedings of the National Academy of Sciences, 111(6): 2349-2354 (Jan. 27, 2014).
McDermott et al., PD-1 as a potential target in cancer therapy, Cancer Med, 2(5): 662-673 (2013).
Mishan-Eisenberg et al., "Differential Regulation of Th1/Th2 Cytokine Respones by Placental Protein 14," The Journal of Immunology 173(9):5524-5530 (2004).
Moingeon, "Strategies for Designing Vaccines Eliciting Th1 Responses in Humans," Journal of Biotechnology 98:189-198 (2002).
Monge et al., "Genetic factors and pathogenesis of waldenstrom's macroglobulinemia," Curr Oncol Rep, 15(5): 450-456 (2013).
Montero et al. Neuregulins and cancer Clin Cancer Res. Jun. 1, 2008;14(11):3237-41. doi: 10.1158/1078-0432.CCR-07-5133.
Morgan L., Leukemia, 8 (Special Issue), 2015.
Mossner et al., "Increasing the Efficacy of CD20 Antibody Therapy Through the Engineering of a New Type II Anti-CD20 Antibody with Enhanced Direct and Immune Effector Cell-Mediated B-cell Cytotoxicity," Blood, 115(22): 4393-4402 (2010).

Myrmel et al., "The Hepatitis C Virus Enigma," APMIS 117:427-439 (2009).
Nagel et al. "Pharmacologic inhibition of MAL T1 protease by phenothiazines as a therapeutic approach for the treatment of aggressive ABC-DLBCL," Cancer Cell, Dec. 11, 2012 ( Dec. 11, 2012), vol. 22, No. 6, pp. 825-837.
National Cancer Institute sponsored study of classifications of non-Hodgkin's lymphomas: summary and description of a working formulation for clinical usage. The Non-Hodgkin's Lymphoma Pathologic Classification Project., The Non-Hodgkin's Lymphoma Pathologic Classification Project, Cancer 49:2112-2135 (1982).
Nicolaou et al., "Calicheamicin θ1: A Rationally Designed Molecule with Extremely Potent and Selective DNA Cleaving Properties and Apoptosis Inducing Activity," Angewandte Chemie International Edition in English 33:183-186 (1994).
Notification of Transmittal of the International Search Report and The Written Opinion for the of the International Searching Authority, or the Declaration for Application No. PCT/US2016/049638, dated Nov. 30, 2016, 14, pages.
O'Brien et al. Combination of the Bruton's tyrosine kinase (BTK) inhibitor PCI-32765 with bendamustine (B)/rituximan® (BR) in patients (pts) with relapsed/refractory (R/R) chronic lymphocytic leukemia (CLL): Interm results of phase Ib/II study. J Clin Onc. 2012. Supp. Abstract 6515.
Ott et al., "CTLA-4 and PD-1/PD-L1 blockade: new immunotherapeutic modalities with durable clinical benefit in melanoma patients," Clin Cancer Res, 19(19): 5300-5309 (2013).
Ou. Second-generation irreversible epidermal growth factor receptor (EGFR) tyrosine kinase inhibitors (TKIs): A better mousetrap? A review of the clinical evidence. Crit Rev Onc/Hemat. 2012;83(3):407-421.
Pan, Z. et al., "Discovery of Selectable Irreversible Inhibitors for Brutons Tyrosine Kinase," ChemMedChem, 1:1-5 (2006).
Paul G Richardson et al: "Pomalidomide alone or in combination with low-dose dexamethasone in relapsed and refractory multiple myeloma: a randomized phase 2 study", Mar. 20, 2014 (Mar. 20, 2014), DOI: 1 0.1182/blood—Retrieved from the Internet: URL:http://www.bloodjournal.org/content/bloodjournal/123/12/1826. fu II. pdf retrieved on Nov. 11, 2016].
PCT/US08/058528 Search Report and Written Opinion dated Sep. 30, 2008.
PCT/US09/50897 IPER and Written Opinion dated Jan. 27, 2011.
PCT/US09/50897 Search Report dated Mar. 15, 2010.
PCT/US2008/058528 International Preliminary Report on Patentability Search Report dated Sep. 29, 2009.
PCT/US2010/52377 International Search Report and Written Opinion dated Jun. 29, 2011.
PCT/US2011/039190 International Preliminary Report on Patentability Search Report dated Dec. 4, 2012.
PCT/US2011/039190 International Search Report and Written Opinion dated Feb. 23, 2012.
PCT/US2013/043888 International Search Report and Written Opinion dated Sep. 23, 2013.
PCT/US2013/068132 International Search Report and Written Opinion dated Jan. 29, 2014.
PCT/US2014/024966 International Preliminary Report on Patentability dated Sep. 15, 2015.
PCT/US2014/024966 International Search Report and Written Opinion dated Aug. 27, 2014.
PCT/US2014/033378 International Search Report and Written Opinion dated Aug. 26, 2014.
PCT/US2014/062278 International Search Report and Written Opinion dated Jan. 29, 2015.
PCT/US2015/040214 International Search Report and Written Opinion dated Dec. 21,2015.
PCT/US2015/043300 International search report and written opinion dated Nov 9, 2015.
PCT/US2015/044095 International search report and written opinion dated Nov 20, 2015.
PCT/US2015/16895 International Search Report and Written Opinion dated May 22, 2015.
PCT/US2015/35665 International Search Report and Written Opinion dated Sep. 21, 2015.

(56) References Cited

OTHER PUBLICATIONS

Perry et al., "Biological prognostic markers in diffuse large B-cell lymphoma," Cancer Control, 19(3): 214-226 (2012).
Pharmacyclics, "Executive Summary: Bruton's Tyrosine Kinase (Btk) Inhibitor Programs for Oncology and Autoimmune Diseases," pp. 1-6 (Jan. 2010).
Ramsay, "Immune checkpoint blockade immunotherapy to activate anti-tumour T-cell immunity," Br J Haematol, 162(3): 313-325 (2013).
Raval et al., "Tumor immunology and cancer immunotherapy: summary of the 2013 SITC primer," J Immunother Cancer, 2:14 (2014).
Readinger et al., "Selective Targeting of ITK Blocks Multiple Steps of HIV Replication," PNAS USA 105(18):6684-6689 (2008).
Rohle et al. "An inhibitor of mutant IDH1 delays growth and promotes differentiation of glioma cells," Science, Apr. 4, 2013 (Apr. 4, 2013), vol. 340, No. 6132, pp. 626-630.
Rooij et al. "The Clinically active BTK inhibitor PCI-32765 targets B-cell receptor-and chemokine-controlled adhesion and migration in chronic lymphocytic leukemia," Blood, Mar. 15, 2012, vol. 119, No. 11, pp. 2590-2594.
Rosenquist et al., Prognostic markers and their clinical applicability in chronic lymphocytic leukemia: where do we stand? Leuk Lymphoma, 54(11): 2351-2361 (2013).
Rozali et al., "Programmed death ligand 2 in cancer-induced immune suppression," Clin Dev Immunol, Article ID: 656340 (2012).
Rummel et al., "Bendamustine plus rituximab is effective and has a favorable toxicity profile in the treatment of mantle cell and low-grade non-Hodgkin's lymphoma," J Clinc Oncol, 23(15):3383-3389 (2005).
Sagiv-Barfi et al. Therapeutic anti-tumor immunity by checkpoint blockade is enhanced by ibrutinib, an inhibitor of both BTK and ITK. Proc. Natl. Acad. Sci. USA 112(9):E966-E972 (Mar. 2015).
Sahu et al., "ITK Inhibitors in Inflammation and Immune-Mediated Disorders," Curr Top Med Chem 9(8):690-703 (2009).
Schiffner et al., "Development of Prophylactic Vaccines Against HIV-1," Retrovirology 10:72 (2013).
Scott et al., "Monoclonal Antibodies in Cancer Therapy," Cancer Immunity 12:14 (2012).
Search Report and Written Opinion for Singapore Application No. 11201401625T, dated Dec. 8, 2016, 27 pages.
SG201208724-3 Search Report and Written Opinion dated Mar. 17, 2015.
Singapore Patent Application No. 201006601-7 Written Opinion dated Aug. 19, 2013.
Singh et al., "Therapeutic vaccines as a promising treatment modality against prostate cancer: rationale and recent advances," Ther Adv Vaccines, 2(5): 137-148 (2014).
Slupsky, "Does B cell receptor signaling in chronic lymphocytic leukaemia cells differ from that in other B cell types??" Scientifica (Cairo) 2014: 1-14 (2014).
Sofian et al., "Serum Profile of T Helper 1 and T Helper 2 Cytokines in Hepatities C Virus Infected Patients," Hepat Mon. 12(12):e6156 (2012).
Specialty Pharmacy Times, "MedCart Specialty Pharmacy: Preparing for the Next Advancements in Hepatitis C Therapy," (Dec. 18, 2012) http://www.specialtypharmacytimes.com/publications/specialty-pharmacy-times/2012/December-2012/MedCart-Specialty-Pharmacy-Preparing-for-the-Next-Advancements-in-Hepatitis-C-Therapy.
Spurrell et al., "Adaptive immunity in cancer immunology and therapeutics," Ecancermedicalscience, 2(8): 441 (2014).
Srivastava et al., "Update on benefit of immunotherapy and targeted therapy in melanoma: the changing landscape," Cancer Manag Res, 6: 279-289 (2014).
Stanford School of Medicine, "Precursor B Lymphoblastic Lymphoma," pp. 1-7 (2005).
Supplementary European Search Report for Application No. EP14774808, dated Oct. 24, 2016, 9 pages.
Supplementary European Search Report for Application No. EP14782886, dated Feb. 8, 2017, 16 pages.
Supplementary European Search Report for EP13850097 dated Mar 31, 2016.
Supplementary Partial European Search Report for Application No. EP14782886 dated Nov. 4, 2016, 11 pages.
Suzuki et al., "Skewed Th1 Responses Caused by Excessive Expression of Txk, a Member of the Tec Family of Tyrosine Kinases, in Patients with Behcet's Disease," Clinical Medicine & Research 4(2):147-151 (2006).
Taiwan Search Report for TW104125847 dated Jun. 13, 2016.
Takayama et al., "Mammalian and Viral IL-10 Enhance C-C Chemokine Receptor 5 but Down-Regulate C-C Chemokine Receptor 7 Expression by Myeloid Dendritic Cells: Impact on Chemotactic Responses and In Vivo Homing Ability," J Immunol, 166: 7136-7143 (2001).
Tame, "Scoring functions: a view from the bench," J Comput Aided Mol Des, 13(2): 99-108 (1999).
Teta et al., "Exercise is Medicine: Using Exercise to Manipulate TH1 and TH2 Immune Function," http://www.freelibrary.com/_/print/PrintArticle.aspx?id=202661767 (2009).
Thimme et al., "Determinants of Viral Clearance and Persistence During Acute Hepatitis C Virus Infection," J Exp Med 194(10):1395-1406 (2001).
Thurn et al. (Future Oncol. Feb. 2011; 7(2): 263-2830.
Toomer et al., "Autoimmunity as a double agent in tumor killing and cancer promotion," Front Immunol, 5: 116 (2014).
Tosti et al., "Anti-cytotoxic T lymphocyte antigen-4 antibodies in melanoma," Clin Cosmet Investig Dermatol, 6: 245-256 (2013).
Trentin et al., "Homcostatic Chemokines Drive Migration of Malignant B Cells in Patients with non-Hodgkin Lymphomas," Blood, 104(2): 502-508 (2004).
Tsai et al., "Detection of Type 2-Like T-Helper Cells in Hepatitis C Virus Infection: Implications for Hepatitis C Virus Chronicity," Hepatology 25(2):449-458 (1997).
Tse et al., "ABT-263: A Potent and Orally Bioavailable Bcl-2 Family Inhibitor," Cancer Res 68:3421-3428 (2008).
Tufman et al., "Biological Markers in Lung Cancer: A Clinician's Perspective," Cancer Biomark 6(3-4):123-135 (2010).
Tykodi et al., "PD-1 as an emerging therapeutic target in renal cell carcinoma: current evidence," OncoTargets and Therapy, 7: 1349-1359 (2014).
Vanneman et al., "Combining immunotherapy and targeted therapies in cancer treatment," Nat Rev Cancer, 12(4): 237-251 (2012).
Vargas et al., "Inhibitors of BTK and ITK: state of the new drugs for cancer, autoimmunity and inflammatory diseases," Scand J Immunol, 78(2): 130-139 (2013).
Vargova et al., "MYB transcriptionally regulates the miR-155 host gene in chronic lymphocytic leukemia," Blood 117(14): 3816-3825 (2011).
Vij Ravi et al: "Ibrutinib, Single Agent or in Combination with Dexamethasone, in Patients with Relapsed or Relapsed/Refractory Multiple Myeloma (MM): Preliminary Phase 2 Results", Blood, American Society of Hematology, US, vol. 124, No. 21, Dec. 1, 2014 (Dec. 1, 2014), ISSN: 0006-4971.
Walker et al., "Treg and CTLA-4: two intertwining pathways to immune tolerance," J Autoimmun, 45: 49-57 (2013).
Wanner et al., "Mammalian Target of Rapamycin Inhibition Includes Cell Cycle Arrest in Diffuse Large B Cell Lymphoma (DLBCL) Cells and Sensitises DLBCL Cells to RituXimab," British Journal of Haematology, 2006, vol. 134, pp. 475-484.
Ward et al., "Isoform-Specific Phosphoinositide 3-Kinase Inhibitors as Therapeutic Agents," Current Opinion in Pharmacology 3(4):426-434 (2003).
Watters, "Cancer Pharmacogenomics: Current and Future Application," Biochimica pp. 99-111 (2003).
Wilson et al. "Targeting B cell receptor signaling with ibrutinib in diffuse large B cell lymphoma," Nat Med. Jul. 20, 2015 (Jul. 20, 2015), vol. 21, pp. 922-926. entire document.
Winer et al. "PCI-32765: a novel Bruton's tyrosine kinase inhibitor for the treatment of lymphoma malignacies," Expert Opinion on Investigational Drugs, Mar. 2012, vol. 21, No. 3, pp. 355-361.

(56) References Cited

OTHER PUBLICATIONS

Woyach et al., "Bruton's Tyrosine Kinase (BTK) Function is Important to the Development and Expansion of Chronic Lymphocytic Leukemia (CLL)," Blood, 123(8): 1207-1213 (2014).
Written Opinion published Oct. 28, 2007 for PCT/IB2005/002350, filed Apr. 28, 2005.
Wu et al., "Immunotherapies: the blockade of inhibitory signals," Int J Biol Sci, 8(10): 1420-1430 (2012).
Yang, et al., "Exploiting Synthetic Lethality for the Therapy of ABC Diffuse Large B Cell Lymphoma," Cancer Cell, 21(6): 723-737 (Jun. 1, 2012).
Yu et al., "Proteasome Inhibitors Block HIV-1 Replication by Affecting Both Cellular and Viral Targets," Biochem Biophys Res Commun. 385(1):100-105 (2009).
Yue et al., "Th1 and Th2 Cytokine Profiles Induced by Hepatitis C Virus F Protein in Peripheral Blood Mononuclear Cells from Chronic Hepatitis C Patients," Immunol Lett 152(2):89-95 (2013).
Zabel et al., "The Novel Chemokine Receptor CXCR7 Regulates Trans-endothelial Migration of Cancer Cells," Mol Cancer, 10(73): 1-8 (2011).
Zapata et al., "Engineering Linear F(ab')2 Fragments for Efficient Production in *Escherichia coli* and Enhanced Antiproliferative Activity," Protein Eng., 10:1057-1062 (1995).
Zhang et al., "In vitro, In vivo and Ex vivo Characterization of Ibrutinib: A Potent Inhibitor of the Efflux Function of the Transporter MRP1," Brit J Pharmacol, 171: 5835-5857 (2014).
Zhao, et al., "Combination of Ibrutinib with ABT-199, a BCL-2 Pathway Inhibitor: Effective Therapeutic Strategy in a Novel Mantle Cell Lymphoma Cell Line Model," Blood, 122(21): 645 (2013).
Zhu et al., "miR-181a/b significantly enhances drug sensitivity in chronic lymphocytic leukemia cells via targeting multiple anti-apoptosis genes," Carcinogenesis 33(7): 1294-1301 (2012).
Zigmond et al., "Ly6Chi Monocytes in the Inflamed Colon Give Rise to Proinflammatory Effector Cells and Migratory Antigen-Presenting Cells," Immunity, 37: 1-15 (2012).
Zitvogel et al., "Targeting PD-1/PD-L1 interactions for cancer immunotherapy," Oncoimmunology, 1(8):1223-1225, (2012).

\* cited by examiner

Fig. 1

| Patient | Age | No. Prior Therapies | Baseline Cytogenetics* | Study Treatment | Duration on Ibrutinib | Best Response/ Days to First Response | Select Identified Mutations** |
|---|---|---|---|---|---|---|---|
| 1 | 9 | 5 | del(17p13.1), +12 | 560 mg qd | 621 days | PR/70 | C481S *BTK* |
| 2 | 9 | 3 | del(11q22.3) | BR x 6 cycles, 420 mg qd | 388 days | CR/70 | C481S *BTK* |
| 3 | 1 | 2 | complex karyotype | Ofatumumab x 24 weeks, 420 mg qd | 674 days | CR/85 | C481S *BTK* |
| 4 | 9 | 9 | del(17p13.1), complex karyotype | 840 mg qd | 868 days | PR/133 | C481S *BTK* |
| 5 | 1 | 4 | del(17p13.1), complex karyotype | Ofatumumab x 24 weeks, 420 mg qd | 505 days | PR/85 | L845F *PLCγ2*, R665W *PLCγ2*, S707Y *PLCγ2*, C481S *BTK* |
| 6 | 5 | 2 | del(17p13.1), complex karyotype | 420 mg qd | 673 days | PR/159 | R665W *PLCγ2* |

| Variable | Progressive disease (CLL, Richter's) | | Discontinuation for non-PD reason (Infection, Toxicity, Other) | |
| --- | --- | --- | --- | --- |
| | Hazard Ratio (95% CI) | P | Hazard Ratio (95% CI) | P |
| BCL6 Mutation Yes vs. No | 2.79 (1.18, 6.58) | 0.019 | --- | --- |
| Complex Karyotype Yes vs. No | 4.00 (1.34, 12.00) | 0.013 | --- | --- |
| Age, years 10-year increase | --- | --- | 1.72 (1.20, 2.46) | 0.003 |
| Prior Treatments 1-unit increase | --- | --- | 1.09 (1.00, 1.19) | 0.051 |

Fig. 9

| Clinical Trial | Days on Study | Type of Relapse | Sample for Mutational Analysis | BTK mutation | PLCγ2 mutation |
|---|---|---|---|---|---|
| 10032 | 170 | DLBCL | no | | |
| 10032 | 337 | Plasmablastic Lymphoma | no | | |
| 10032 | 785 | DLBCL | yes/blood | C481S | no |
| 10032 | 33 | Peripheral T Cell Lymphoma | no | | |
| 10032 | 562 | DLBCL | no | | |
| 10032 | 387 | DLBCL | yes/node | no | no |
| 10053 | 479 | DLBCL progression** | no | | |
| 10053 | 168 | DLBCL progression** | no | | |
| 10053 | 377 | Composite B&T Cell Lymphoma | no | | |
| 10053 | 429 | DLBCL | yes/blood | C481Y, C481R, L527W | no |
| 11133 | 271 | DLBCL | yes/blood*** | no | no |
| 11133 | 309 | DLBCL | no | | |
| 11133 | 125 | DLBCL | yes/blood*** | no | no |
| 11133 | 308 | Hodgkin lymphoma | no | | |
| 11133 | 231 | DLBCL | yes/blood*** | no | no |
| 11133 | 55 | DLBCL | no | | |
| 11133 | 26 | DLBCL | no | | |
| 10032* | 664 | CLL | yes/blood | no | R665W |
| 10032 | 965 | CLL | yes/blood | C481F | no |
| 10032 | 1119 | CLL | yes/blood | C481S | no |
| 10032 | 1295 | CLL | yes/marrow | C481S | D1140G |
| 10053* | 673 | CLL | yes/blood | C481S | no |
| 10053* | 505 | CLL | yes/blood | no | R665W, L845F, S707Y |
| 10053 | 693 | CLL | yes/blood | C481S | no |
| 10053 | 426 | CLL | no | | |
| 10053 | 115 | CLL | no | | |
| 10053 | 1034 | CLL | yes/blood | C481S | no |
| 11133 | 474 | CLL | yes/blood | C481S | no |
| 11133 | 511 | CLL | yes/blood | no | R665W, S707P, S707F, R742P, L845fs |

\* Previously presented: Chang, ASCO 2013
\*\* History of Richter's Transformation
\*\*\* Richter's patients without increasing absolute lymphocyte count at relapse

SEQUENCE LISTING

```
<160> NUMBER OF SEQ ID NOS: 2

<210> SEQ ID NO 1
<211> LENGTH: 4289
<212> TYPE: DNA
<213> ORGANISM: Homo sapiens
<220> FEATURE:
<221> NAME/KEY: misc_feature
<222> LOCATION: (1)..(4289)
<223> OTHER INFORMATION: PLCgamma2

<400> SEQUENCE: 1
agtagcgagc gccggcggcg gagggcgtga gcggcgctga gtgacccgag tcgggacgcg      60
ggctgcgcgc gcgggacccc ggagcccaaa cccggggcag gcgggcagct gtgcccgggc     120
ggcacggcca gcttcctgat ttctcccgat tccttccttc tccctggagc ggccgacaat     180
gtccaccacg gtcaatgtag attcccttgc ggaatatgag aagagccaga tcaagagagc     240
cctggagctg gggacggtga tgactgtgtt cagcttccgc aagtccaccc ccgagcggag     300
aaccgtccag gtgatcatgg agacgcggca ggtggcctgg agcaagaccg ccgacaagat     360
cgagggcttc ttggatatca tggaaataaa agaaatccgc ccagggaaga actccaaaga     420
tttcgagcga gcaaaagcag ttcgccagaa agaagactgc tgcttcacca tcctatatgg     480
cactcagttc gtcctcagca cgctcagctt ggcagctgac tctaaagagg atgcagttaa     540
ctggctctct ggcttgaaaa tcttacacca ggaagcgatg aatgcgtcca cgcccaccat     600
tatcgagagt tggctgagaa agcagatata ttctgtggat caaaccagaa gaaacagcat     660
cagtctccga gagttgaaga ccatcttgcc cctgatcaac tttaaagtga gcagtgccaa     720
gttccttaaa gataagtttg tggaaatagg agcacacaaa gatgagctca gctttgaaca     780
gttccatctc ttctataaaa aacttatgtt tgaacagcaa aaatcgattc tcgatgaatt     840
caaaaaggat tcgtccgtgt tcatcctggg gaacactgac aggccggatg cctctgctgt     900
ttacctgcat gacttccaga ggtttctcat acatgaacag caggagcatt gggctcagga     960
tctgaacaaa gtccgtgagc ggatgacaaa gttcattgat gacaccatgc gtgaaactgc    1020
tgagcctttc ttgtttgtgg atgagttcct cacgtacctg ttttcacgag aaaacagcat    1080
ctgggatgag aagtatgacg cggtggacat gcaggacatg aacaaccccc tgtctcatta    1140
ctggatctcc tcgtcacata acacgtacct tacaggtgac cagctgcgga gcgagtcgtc    1200
cccagaagct tacatccgct gcctgcgcat gggctgtcgc tgcattgaac tggactgctg    1260
ggacgggccc gatgggaagc cggtcatcta ccatggctgg acgcggacta ccaagatcaa    1320
gtttgacgac gtcgtgcagg ccatcaaaga ccacgccttt gttacctcga gcttcccagt    1380
```

```
gatcctgtcc atcgaggagc actgcagcgt ggagcaacag cgtcacatgg ccaaggcctt    1440
caaggaagta tttggcgacc tgctgttgac gaagcccacg gaggccagtg ctgaccagct    1500
gccctcgccc agccagctgc gggagaagat catcatcaag cataagaagc tgggcccccg    1560
aggcgatgtg gatgtcaaca tggaggacaa gaaggacgaa cacaagcaac agggggagct    1620
gtacatgtgg gattccattg accagaaatg gactcggcac tactgcgcca ttgccgatgc    1680
caagctgtcc ttcagtgatg acattgaaca gactatggag gaggaagtgc cccaggatat    1740
accccctaca gaactacatt ttggggagaa atggttccac aagaaggtgg agaagaggac    1800
gagtgccgag aagttgctgc aggaatactg catggagacg gggggcaagg atggcacctt    1860
cctggttcgg gagagcgaga ccttccccaa tgactacacc ctgtccttct ggcggtcagg    1920
ccgggtccag cactgccgga tccgctccac catggagggc gggaccctga atactactt     1980 gactgacaac ctcaccttca gcagcatcta tgccctcatc cagcactacc gcgagacgca    2040
cctgcgctgc gccgagttcg agctgcggct cacggaccct gtgcccaacc ccaaccccca    2100
cgagtccaag ccgtggtact atgacagcct gagccgcgga gaggcagagg acatgctgat    2160
gaggattccc cgggacgggg ccttcctgat ccggaagcga gaggggagcg actcctatgc    2220
catcaccttc agggctaggg gcaaggtaaa gcattgtcgc atcaaccggg acggccggca    2280
ctttgtgctg ggaccctccg cctattttga gagtctggtg gagctcgtca gttactacga    2340
gaagcattca ctctaccgaa agatgagact gcgctacccc gtgacccccg agctcctgga    2400
gcgctacaat atggaaagag atataaactc cctctacgac gtcagcagaa tgtatgtgga    2460
tcccagtgaa atcaatccgt ccatgcctca gagaaccgtg aaagctctgt atgactacaa    2520
agccaagcga agcgatgagc tgagcttctg ccgtggtgcc ctcatccaca atgtctccaa    2580
ggagcccggg ggctggtgga aggagacta tggaaccagg atccagcagt acttcccatc     2640
caactacgtc gaggacatct caactgcaga cttcgaggag ctagaaaagc agattattga    2700
agacaatccc ttagggtctc tttgcagagg aatattggac ctcaatacct ataacgtcgt    2760
gaaagcccct cagggaaaaa accagaagtc ctttgtcttc atcctggagc ccaagcagca    2820
gggcgatcct ccggtggagt ttgccacaga cagggtggag gagctctttg agtggtttca    2880
gagcatccga gagatcacct ggaagattga caccaaggag aacaacatga agtactggga    2940
gaagaaccag tccatcgcca tcgagctctc tgacctggtt gtctactgca aaccaaccag    3000
caaaaccaag gacaacttag aaaatcctga cttccgagaa atccgctcct ttgtggagac    3060
gaaggctgac agcatcatca gacagaagcc cgtcgacctc ctgaagtaca atcaaaaggg    3120
cctgacccgc gtctacccaa agggacaaag agttgactct tcaaactacg accccttccg    3180
cctctggctg tgcggttctc agatggtggc actcaatttc cagacggcag ataagtacat    3240
gcagatgaat cacgcattgt tttctctcaa tgggcgcacg ggctacgttc tgcagcctga    3300
gagcatgagg acagagaaat atgacccgat gccacccgag tcccagagga gatcctgat     3360 gacgctgaca gtcaaggttc tcggtgctcg ccatctcccc aaacttggac gaagtattgc    3420
ctgtcccttt gtagaagtgg agatctgtgg agccgagtat gacaacaaca agttcaagac    3480
gacggttgtg aatgataatg gcctcagccc tatctgggct ccaacacagg agaaggtgac    3540
atttgaaatt tatgacccaa acctggcatt tctgcgcttt gtggtttatg aagaagatat    3600
gttcagcgat cccaacttc ttgctcatgc cacttacccc attaaagcag tcaaatcagg    3660
attcaggtcc gttcctctga agaatgggta cagcgaggac atagagctgg cttccctcct    3720
```

-continued

```
ggttttctgt gagatgcggc cagtcctgga gagcgaagag gaactttact cctcctgtcg    3780
ccagctgagg aggcggcaag aagaactgaa caaccagctc tttctgtatg acacacacca    3840
gaacttgcgc aatgccaacc gggatgccct ggttaaagag ttcagtgtta atgagaacca    3900
gctccagctg taccaggaga atgcaacaa gaggttaaga gagaagagag tcagcaacag     3960
caagttttac tcatagaagc tggggtatgt gtgtaagggt attgtgtgtg tgcgcatgtg    4020
tgtttgcatg taggagaacg tgccctattc acactctggg aagacgctaa tctgtgacat    4080
cttttcttca agcctgccat caaggacatt tcttaagacc caactggcat gagttggggt    4140
aatttcctat tatttcatc ttggacaact ttcttaactt atattcttta tagaggattc      4200
cccaaaatgt gctcctcatt tttggcctct catgttccaa acctcattga ataaaagcaa    4260
tgaaaacctt gaaaaaaaaa aaaaaaaa                                      4289
```

<210> SEQ ID NO 2
<211> LENGTH: 1265
<212> TYPE: PRT
<213> ORGANISM: Homo sapiens
<220> FEATURE:
<221> NAME/KEY: MISC_FEATURE
<222> LOCATION: (1)..(1265)
<223> OTHER INFORMATION: PLCgamma2

<400> SEQUENCE: 2

```
Met Ser Thr Thr Val Asn Val Asp Ser Leu Ala Glu Tyr Glu Lys Ser
1               5                   10                  15

Gln Ile Lys Arg Ala Leu Glu Leu Gly Thr Val Met Thr Val Phe Ser
            20                  25                  30

Phe Arg Lys Ser Thr Pro Glu Arg Arg Thr Val Gln Val Ile Met Glu
        35                  40                  45

Thr Arg Gln Val Ala Trp Ser Lys Thr Ala Asp Lys Ile Glu Gly Phe
    50                  55                  60

Leu Asp Ile Met Glu Ile Lys Glu Ile Arg Pro Gly Lys Asn Ser Lys
65                  70                  75                  80

Asp Phe Glu Arg Ala Lys Ala Val Arg Gln Lys Glu Asp Cys Cys Phe
                85                  90                  95

Thr Ile Leu Tyr Gly Thr Gln Phe Val Leu Ser Thr Leu Ser Leu Ala
            100                 105                 110

Ala Asp Ser Lys Glu Asp Ala Val Asn Trp Leu Ser Gly Leu Lys Ile
        115                 120                 125

Leu His Gln Glu Ala Met Asn Ala Ser Thr Pro Thr Ile Ile Glu Ser
    130                 135                 140

Trp Leu Arg Lys Gln Ile Tyr Ser Val Asp Gln Thr Arg Arg Asn Ser
145                 150                 155                 160

Ile Ser Leu Arg Glu Leu Lys Thr Ile Leu Pro Leu Ile Asn Phe Lys
                165                 170                 175

Val Ser Ser Ala Lys Phe Leu Lys Asp Lys Phe Val Glu Ile Gly Ala
            180                 185                 190

His Lys Asp Glu Leu Ser Phe Glu Gln Phe His Leu Phe Tyr Lys Lys
        195                 200                 205

Leu Met Phe Glu Gln Gln Lys Ser Ile Leu Asp Glu Phe Lys Lys Asp
    210                 215                 220

Ser Ser Val Phe Ile Leu Gly Asn Thr Asp Arg Pro Asp Ala Ser Ala
225                 230                 235                 240

Val Tyr Leu His Asp Phe Gln Arg Phe Leu Ile His Glu Gln Gln Glu
                245                 250                 255
```

-continued

His Trp Ala Gln Asp Leu Asn Lys Val Arg Glu Arg Met Thr Lys Phe
                260                 265                 270

Ile Asp Asp Thr Met Arg Glu Thr Ala Glu Pro Phe Leu Phe Val Asp
            275                 280                 285

Glu Phe Leu Thr Tyr Leu Phe Ser Arg Glu Asn Ser Ile Trp Asp Glu
        290                 295                 300

Lys Tyr Asp Ala Val Asp Met Gln Asp Met Asn Asn Pro Leu Ser His
305                 310                 315                 320

Tyr Trp Ile Ser Ser Ser His Asn Thr Tyr Leu Thr Gly Asp Gln Leu
                325                 330                 335

Arg Ser Glu Ser Ser Pro Glu Ala Tyr Ile Arg Cys Leu Arg Met Gly
            340                 345                 350

Cys Arg Cys Ile Glu Leu Asp Cys Trp Asp Gly Pro Asp Gly Lys Pro
        355                 360                 365

Val Ile Tyr His Gly Trp Thr Arg Thr Thr Lys Ile Lys Phe Asp Asp
    370                 375                 380

Val Val Gln Ala Ile Lys Asp His Ala Phe Val Thr Ser Ser Phe Pro
385                 390                 395                 400

Val Ile Leu Ser Ile Glu Glu His Cys Ser Val Glu Gln Gln Arg His
                405                 410                 415

Met Ala Lys Ala Phe Lys Glu Val Phe Gly Asp Leu Leu Leu Thr Lys
            420                 425                 430

Pro Thr Glu Ala Ser Ala Asp Gln Leu Pro Ser Pro Ser Gln Leu Arg
        435                 440                 445

Glu Lys Ile Ile Ile Lys His Lys Lys Leu Gly Pro Arg Gly Asp Val
    450                 455                 460

Asp Val Asn Met Glu Asp Lys Lys Asp Glu His Lys Gln Gln Gly Glu
465                 470                 475                 480

Leu Tyr Met Trp Asp Ser Ile Asp Gln Lys Trp Thr Arg His Tyr Cys
                485                 490                 495

Ala Ile Ala Asp Ala Lys Leu Ser Phe Ser Asp Asp Ile Glu Gln Thr
            500                 505                 510

Met Glu Glu Glu Val Pro Gln Asp Ile Pro Pro Thr Glu Leu His Phe
        515                 520                 525

Gly Glu Lys Trp Phe His Lys Lys Val Glu Lys Arg Thr Ser Ala Glu
    530                 535                 540

Lys Leu Leu Gln Glu Tyr Cys Met Glu Thr Gly Gly Lys Asp Gly Thr
545                 550                 555                 560

Phe Leu Val Arg Glu Ser Glu Thr Phe Pro Asn Asp Tyr Thr Leu Ser
                565                 570                 575

Phe Trp Arg Ser Gly Arg Val Gln His Cys Arg Ile Arg Ser Thr Met
            580                 585                 590

Glu Gly Gly Thr Leu Lys Tyr Tyr Leu Thr Asp Asn Leu Thr Phe Ser
        595                 600                 605

Ser Ile Tyr Ala Leu Ile Gln His Tyr Arg Glu Thr His Leu Arg Cys
    610                 615                 620

Ala Glu Phe Glu Leu Arg Leu Thr Asp Pro Val Pro Asn Pro Asn Pro
625                 630                 635                 640

His Glu Ser Lys Pro Trp Tyr Tyr Asp Ser Leu Ser Arg Gly Glu Ala
                645                 650                 655

Glu Asp Met Leu Met Arg Ile Pro Arg Asp Gly Ala Phe Leu Ile Arg
            660                 665                 670

-continued

Lys Arg Glu Gly Ser Asp Ser Tyr Ala Ile Thr Phe Arg Ala Arg Gly
            675                 680                 685

Lys Val Lys His Cys Arg Ile Asn Arg Asp Gly Arg His Phe Val Leu
        690                 695                 700

Gly Thr Ser Ala Tyr Phe Glu Ser Leu Val Glu Leu Val Ser Tyr Tyr
705                 710                 715                 720

Glu Lys His Ser Leu Tyr Arg Lys Met Arg Leu Arg Tyr Pro Val Thr
                725                 730                 735

Pro Glu Leu Leu Glu Arg Tyr Asn Met Glu Arg Asp Ile Asn Ser Leu
            740                 745                 750

Tyr Asp Val Ser Arg Met Tyr Val Asp Pro Ser Glu Ile Asn Pro Ser
        755                 760                 765

Met Pro Gln Arg Thr Val Lys Ala Leu Tyr Asp Tyr Lys Ala Lys Arg
    770                 775                 780

Ser Asp Glu Leu Ser Phe Cys Arg Gly Ala Leu Ile His Asn Val Ser
785                 790                 795                 800

Lys Glu Pro Gly Gly Trp Trp Lys Gly Asp Tyr Gly Thr Arg Ile Gln
                805                 810                 815

Gln Tyr Phe Pro Ser Asn Tyr Val Glu Asp Ile Ser Thr Ala Asp Phe
            820                 825                 830

Glu Glu Leu Glu Lys Gln Ile Ile Glu Asp Asn Pro Leu Gly Ser Leu
        835                 840                 845

Cys Arg Gly Ile Leu Asp Leu Asn Thr Tyr Asn Val Val Lys Ala Pro
    850                 855                 860

Gln Gly Lys Asn Gln Lys Ser Phe Val Phe Ile Leu Glu Pro Lys Gln
865                 870                 875                 880

Gln Gly Asp Pro Pro Val Glu Phe Ala Thr Asp Arg Val Glu Glu Leu
                885                 890                 895

Phe Glu Trp Phe Gln Ser Ile Arg Glu Ile Thr Trp Lys Ile Asp Thr
            900                 905                 910

Lys Glu Asn Asn Met Lys Tyr Trp Glu Lys Asn Gln Ser Ile Ala Ile
        915                 920                 925

Glu Leu Ser Asp Leu Val Val Tyr Cys Lys Pro Thr Ser Lys Thr Lys
    930                 935                 940

Asp Asn Leu Glu Asn Pro Asp Phe Arg Glu Ile Arg Ser Phe Val Glu
945                 950                 955                 960

Thr Lys Ala Asp Ser Ile Ile Arg Gln Lys Pro Val Asp Leu Leu Lys
                965                 970                 975

Tyr Asn Gln Lys Gly Leu Thr Arg Val Tyr Pro Lys Gly Gln Arg Val
            980                 985                 990

Asp Ser Ser Asn Tyr Asp Pro Phe Arg Leu Trp Leu Cys Gly Ser Gln
        995                 1000                1005

Met Val Ala Leu Asn Phe Gln Thr Ala Asp Lys Tyr Met Gln Met
    1010                1015                1020

Asn His Ala Leu Phe Ser Leu Asn Gly Arg Thr Gly Tyr Val Leu
    1025                1030                1035

Gln Pro Glu Ser Met Arg Thr Glu Lys Tyr Asp Pro Met Pro Pro
    1040                1045                1050

Glu Ser Gln Arg Lys Ile Leu Met Thr Leu Thr Val Lys Val Leu
    1055                1060                1065

Gly Ala Arg His Leu Pro Lys Leu Gly Arg Ser Ile Ala Cys Pro
    1070                1075                1080

Phe Val Glu Val Glu Ile Cys Gly Ala Glu Tyr Asp Asn Asn Lys

-continued

```
             1085                1090                1095
Phe Lys Thr Thr Val Val Asn Asp Asn Gly Leu Ser Pro Ile Trp
        1100                1105                1110

Ala Pro Thr Gln Glu Lys Val Thr Phe Glu Ile Tyr Asp Pro Asn
        1115                1120                1125

Leu Ala Phe Leu Arg Phe Val Val Tyr Glu Glu Asp Met Phe Ser
        1130                1135                1140

Asp Pro Asn Phe Leu Ala His Ala Thr Tyr Pro Ile Lys Ala Val
        1145                1150                1155

Lys Ser Gly Phe Arg Ser Val Pro Leu Lys Asn Gly Tyr Ser Glu
        1160                1165                1170

Asp Ile Glu Leu Ala Ser Leu Leu Val Phe Cys Glu Met Arg Pro
        1175                1180                1185

Val Leu Glu Ser Glu Glu Glu Leu Tyr Ser Ser Cys Arg Gln Leu
        1190                1195                1200

Arg Arg Arg Gln Glu Glu Leu Asn Asn Gln Leu Phe Leu Tyr Asp
        1205                1210                1215

Thr His Gln Asn Leu Arg Asn Ala Asn Arg Asp Ala Leu Val Lys
        1220                1225                1230

Glu Phe Ser Val Asn Glu Asn Gln Leu Gln Leu Tyr Gln Glu Lys
        1235                1240                1245

Cys Asn Lys Arg Leu Arg Glu Lys Arg Val Ser Asn Ser Lys Phe
        1250                1255                1260

Tyr Ser
    1265
```

US 9,885,086 B2

PHOSPHOLIPASE C GAMMA 2 AND RESISTANCE ASSOCIATED MUTATIONS

CROSS-REFERENCE

This application claims the benefit of priority from U.S. Provisional Patent Application Nos. 61/968,315, filed Mar. 20, 2014; and 62/002,743, filed May 23, 2014; which are herein incorporated by reference in their entirety.

INCORPORATION BY REFERENCE OF SEQUENCE LISTING SUBMITTED AS A TEXT FILE VIA EFS-WEB

The instant application contains a Sequence Listing, which has been submitted as a computer readable text file in ASCII format via EFS-Web and is hereby incorporated in its entirety by reference herein. The text file, created date of May 20, 2015, is named 25922-307-201SEQ.txt and is 16,991 bytes in size.

BACKGROUND OF THE INVENTION

B-cell receptor (BCR) complex and its associated proteins play a critical role in the development, proliferation and survival of normal or malignant B cells. BCR function is required for normal antibody production and abnormal BCR signal transduction is implicated in B-cell malignancies. BCR signal transduction operates through several signaling pathways, including the PLCγ/calcium/NFAT pathway, the PI3K pathway, the IKK/NF-κB pathway and the canonical ERK pathway.

Phospholipase C gamma 2 (PLCγ2) is an enzyme of the phospholipase C family that cleaves the phospholipid phosphatidylinositol 4,5-bisphosphate (PIP2) into diacyl glycerol (DAG) and inositol 1,4,5-trisphosphate (IP3). DAG remains bound to the membrane, and IP3 is released as a soluble structure into the cytosol. IP3 then diffuses through the cytosol to bind to IP3 receptors, particular calcium channels in the smooth endoplasmic reticulum (ER). This causes the cytosolic concentration of calcium to increase, causing a cascade of intracellular changes and activity. In addition, calcium and DAG together work to activate protein kinase C, which goes on to phosphorylate other molecules within the pathway, leading to altered cellular activity. In some cases, the mutant PLCγ2 polypeptide are constitutively active (i.e. does not require phosphorylation by BTK).

SUMMARY OF THE INVENTION

Disclosed herein is a method of assessing whether a subject is less responsive or likely to become less responsive to therapy with a BTK inhibitor, comprising: (a) testing a sample containing a nucleic acid molecule encoding a PLCγ2 polypeptide from the subject; (b) determining whether the encoded PLCγ2 polypeptide is modified at an amino acid position corresponding to amino acid position 742, 845, or 1140 of the amino acid sequence set forth in SEQ ID NO: 2; and (c) characterizing the subject as resistant or likely to become resistant to therapy with a BTK inhibitor if the subject has the modification at amino acid position 742, 845, or 1140. In some embodiments, the subject has been administered a covalent and/or irreversible BTK inhibitor for treatment of a cancer. Disclosed herein is a method of monitoring whether a subject receiving a BTK inhibitor for treatment of a cancer has developed or is likely to develop resistance to the therapy, comprising: (a) testing a sample containing a nucleic acid molecule encoding a PLCγ2 polypeptide from the subject; (b) determining whether the encoded PLCγ2 polypeptide is modified at an amino acid position corresponding to amino acid position 742, 845, or 1140 of the amino acid sequence set forth in SEQ ID NO: 2; and (c) characterizing the subject as resistant or is likely to become resistant to therapy with a BTK inhibitor if the subject has the modification at amino acid position 742, 845, or 1140. Disclosed herein is a method of optimizing the therapy of a subject receiving a BTK inhibitor for treatment of a cancer, comprising: (a) testing a sample containing a nucleic acid molecule encoding a PLCγ2 polypeptide from the subject; and (b) determining whether the encoded PLCγ2 polypeptide is modified at an amino acid position corresponding to amino acid position 742, 845, or 1140 of the amino acid sequence set forth in SEQ ID NO: 2. In some embodiments, the modification comprises a substitution, an addition or a deletion of the amino acid at amino acid position 742, 845, or 1140 in the PLCγ2 polypeptide. In some embodiments, the modification is a substitution of arginine to an amino acid selected from among leucine, cysteine, isoleucine, valine, alanine, glycine, methionine, serine, threonine, phenylalanine, tryptophan, lysine, histidine, proline, tyrosine, asparagine, glutamine, aspartic acid and glutamic acid at amino acid position 742 of the PLCγ2 polypeptide. In some embodiments, the modification is a substitution of arginine to proline at amino acid position 742 of the PLCγ2 polypeptide. In some embodiments, the modification is a substitution of leucine to an amino acid selected from among cysteine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 845 of the PLCγ2 polypeptide. In some embodiments, the modification is a substitution of leucine to phenylalanine, tyrosine or tryptophan at amino acid position 845 of the PLCγ2 polypeptide. In some embodiments, the modification is a substitution of leucine to phenylalanine at amino acid position 845 of the PLCγ2 polypeptide. In some embodiments, the modification is a substitution of aspartic acid to an amino acid selected from among arginine, leucine, cysteine, isoleucine, valine, alanine, glycine, methionine, serine, threonine, phenylalanine, tryptophan, lysine, histidine, proline, tyrosine, asparagine, glutamine, and glutamic acid at amino acid position 742 of the PLCγ2 polypeptide. In some embodiments, the modification is a substitution of aspartic acid to glycine at amino acid position 742 of the PLCγ2 polypeptide. In some embodiments, the nucleic acid encoding the modified PLCγ2 polypeptide has a mutation of adenine to thymidine at nucleic acid position corresponding to nucleic acid position 2713 in the sequence of nucleotides set forth in SEQ ID NO: 1. In some embodiments, the PLCγ2 polypeptide further comprises modifications at additional amino acid positions. In some embodiments, the method of optimizing the therapy of a subject receiving a BTK inhibitor for treatment of a cancer, further comprising discontinuing treatment with the BTK inhibitor if the subject has the modification at amino acid position 742, 845, or 1140 in the PLCγ2 polypeptide. In some embodiments, the method of optimizing the therapy of a subject receiving a BTK inhibitor for treatment of a cancer, further comprising discontinuing treatment with the BTK inhibitor if the subject has one or more modifications with at least one modification at amino acid position 742, 845, or 1140 in the PLCγ2 polypeptide. In some embodiments, the method of optimizing the therapy of a subject receiving a BTK inhibitor for treatment of a cancer, further comprising administering an inhibitor of PLCγ2 if the subject has one or more modifications with at least one modification at amino acid position 742, 845, or 1140 in the PLCγ2 polypeptide. In some embodiments, the method of optimizing the therapy of a subject receiving a BTK inhibitor for treatment of a cancer, further comprising administering an inhibitor of LYN, SYK, JAK, PI3K, MAPK, MEK or NFκB if the subject has at least the modification at amino acid position 742, 845, or 1140 in the PLCγ2 polypeptide. In some embodiments, the method of optimizing the therapy of a subject receiving a BTK inhibitor for treatment of a cancer, further comprising continuing treatment with the BTK inhibitor if the subject does not have modifications in the PLCγ2 polypeptide. In some embodiments, the subject possesses high-risk cytogenetic features. In some embodiments, the high-risk cytogenetic features comprise del(11q22.3), del(17p13.1) or complex karyotype. In some embodiments, the methods further comprising testing a sample containing a nucleic acid molecule encoding a PLCγ2 polypeptide and an additional polypeptide and determining whether the additional polypeptide contains mutations. In some embodiments, the additional polypeptide is a BTK polypeptide. In some embodiments, the nucleic acid molecule is RNA or DNA. In some embodiments, the DNA is genomic DNA. In some embodiments, the methods further comprises isolating mRNA from the sample. In some embodiments, testing comprises amplifying the nucleic acid encoding amino acid position 742, 845, or 1140 of the PLCγ2 polypeptide. In some embodiments, amplification is by isothermal amplification or polymerase chain reaction (PCR). In some embodiments, the amplification is by PCR. In some embodiments, the PCR amplification comprises using oligonucleotide primer pairs that flank the region encoding amino acid position 742, 845, or 1140 of the PLCγ2 polypeptide. In some embodiments, testing comprises sequencing the amplified nucleic acids. In some embodiments, testing comprises contacting nucleic acids with sequence specific nucleic acid probes, wherein the sequence specific nucleic acid probes: (a) bind to either nucleic acid encoding a modified PLCγ2 that is modified at amino acid position 742, 845, or 1140; and (b) do not bind to nucleic acid encoding the wild-type PLCγ2 having arginine at amino acid position 742, do not bind to nucleic acid encoding the wild-type PLCγ2 having leucine at amino acid position 845, or do not bind to nucleic acid encoding the wild-type PLCγ2 having aspartic acid at amino acid position 1140. In some embodiments, testing comprises PCR amplification using the sequence specific nucleic acid probes. In some embodiments, the methods further comprise obtaining the sample from the subject. In some embodiments, the sample contains one or more tumor cells from the subject. In some embodiments, the sample contains circulating tumor DNA (ctDNA). In some embodiments, the sample is a tumor biopsy sample, a blood sample, a serum sample, a lymph sample or a bone marrow aspirate. In some embodiments, the BTK inhibitor is a covalent and/or irreversible BTK inhibitor. In some embodiments, the covalent and/or irreversible BTK inhibitor is selected from among ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the covalent and/or irreversible BTK inhibitor is ibrutinib. In some embodiments, the subject has cancer. In some embodiments, the cancer is a hematologic cancer. In some embodiments, the cancer is a B-cell malignancy. In some embodiments, the cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the B-cell malignancy is CLL. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation. In some embodiments, the sample is a sample obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the covalent and/or irreversible BTK inhibitor. In some embodiments, the sample is obtained 1, 2, 3, 4, 5, 6, 7, 8, 9, 10 times over the course of treatment with the irreversible BTK inhibitor. In some embodiments, the subject is responsive to the treatment with the irreversible BTK inhibitor when it is first administered.

Disclosed herein is a method of maintenance therapy in a patient having a hematologic cancer, comprising: (a) administering to the patient a maintenance therapy regimen comprising administering a therapeutically effective dose of a BTK inhibitor; and (b) monitoring the patient at predetermined intervals of time over the course of the maintenance therapy regimen to determine whether the subject has mutation in an endogenous gene encoding PLCγ2 that results in a modification at an amino acid position corresponding to amino acid position 742, 845, or 1140 of the amino acid sequence set forth in SEQ ID NO: 2. In some embodiments, the modification in the PLCγ2 polypeptide is R742P, L845F, or D1140G. In some embodiments, the modification in the PLCγ2 polypeptide further comprises additional modifications. In some embodiments, the method further comprises discontinuing maintenance therapy regimen if the subject has one or more mutations with at least one mutation at amino acid position 742, 845, or 1140 in PLCγ2 polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has at least the modification at amino acid position 742, 845, or 1140 in the PLCγ2 polypeptide. In some embodiments, the method further comprises continuing maintenance therapy regimen if the subject does not have mutation at amino acid position 742, 845, or 1140 in PLCγ2 polypeptide. In some embodiments, the predetermined interval of time is every week, every month, every 2 months, every 3 months, every 4 months, every 5 months, every 6 months, every 7 months, every 8 months, every 9 months, every 10 months, every 11 months, or every year. In some embodiments, the subject possesses high-risk cytogenetic features. In some embodiments, the high-risk cytogenetic features comprise del(11q22.3), del(17p13.1) or complex karyotype. In some embodiments, the sample contains one or more cancer cells. In some embodiments, the sample contains ctDNA. In some embodiments, the method further comprises testing a sample from the subject prior to treatment with the BTK inhibitor. In some embodiments, the BTK inhibitor is a covalent and/or irreversible BTK inhibitor. In some embodiments, the covalent and/or irreversible BTK inhibitor is selected from among ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK417891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the covalent and/or irreversible BTK inhibitor is ibrutinib. In some embodiments, the maintenance therapy regimen comprises administering the BTK inhibitor at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, the cancer is a hematologic cancer. In some embodiments, the cancer is a B-cell malignancy. In some embodiments, the cancer is selected from among a leukemia, a lymphoma, or a myeloma. In some embodiments, the cancer is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the B-cell malignancy is CLL. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

Disclosed herein is an isolated PLCγ2 polypeptide or a variant thereof having PLCγ2 activity comprising a modification at an amino acid position corresponding to amino acid position 742, 845, or 1140 of the amino acid sequence set forth in SEQ ID NO: 2, wherein the modification confers resistance of a cancer cell to inhibition with a BTK inhibitor. In some embodiments, the BTK inhibitor is ibrutinib. In some embodiments, the isolated PLCγ2 polypeptide comprises the sequence of amino acids set forth in SEQ ID NO: 2 or a variant that has at least or at least about 60%, 70%, 75%, 80%, 85%, 90%, 95%, 96%, 97%, 98%, 99% or more sequence identity with the polypeptide having the sequence set forth in SEQ ID NO: 2, wherein the amino acid at position 742 is not arginine, or wherein the amino acid at position 845 is not leucine, or wherein the amino acid at position 1140 is not aspartic acid. In some embodiments, the amino acid at position 742 is proline. In some embodiments, the amino acid at position 845 is phenylalanine. In some embodiments, the amino acid at position 1140 is glycine. In some embodiments, disclosed herein is an isolated nucleic acid molecule encoding the isolated PLCγ2 polypeptide. In some embodiments, the nucleic acid is a DNA or an RNA molecule. In some embodiments, the DNA is a cDNA molecule. In some embodiments, the nucleic acid comprises the sequence of nucleic acid set forth in SEQ ID NO: 1 or a variant that has at least or at least about 60%, 70%, 75%, 80%, 85%, 90%, 95%, 96%, 97%, 98%, 99% or more sequence identity with the nucleic acid having the sequence set forth in SEQ ID NO: 1, wherein the nucleic acid codon encoding amino acid at position 742 does not encode aspartic acid wherein the nucleic acid codon encoding amino acid at position 845 does not encode leucine, or wherein the nucleic acid codon encoding amino acid at position 1140 does not encode glycine.

Disclosed herein is a system of detecting a modified PLCγ2 that confers resistance to inhibition with an irreversible BTK inhibitor in a subject, comprising: (a) a sample containing a nucleic acid molecule encoding a PLCγ2 polypeptide from the subject; and (b) a microarray comprising nucleic acid encoding a modified PLCγ2 polypeptide or a portion thereof that is modified at an amino acid position corresponding to amino acid position 742, 845, or 1140 of the amino acid sequence set forth in SEQ ID NO: 2. In some embodiments, the microarray further comprises comprising nucleic acid encoding a modified PLCγ2 polypeptide or a portion thereof that is modified at additional amino acid positions. In some embodiments, the microarray is contained on a microchip.

Disclosed herein is a system of detecting a modified PLCγ2 that confers resistance to inhibition with an irreversible BTK inhibitor in a subject, comprising: (a) a sample containing a nucleic acid molecule encoding a PLCγ2 polypeptide from the subject; and (b) a sequence specific nucleic acid probe, wherein the sequence specific nucleic acid probe: (i) binds to nucleic acid encoding a modified PLCγ2 that is modified at amino acid position 742, 845, or 1140; and (ii) does not bind to nucleic acid encoding the wild-type PLCγ2 having arginine at amino acid position 742, or does not bind to nucleic acid encoding the wild-type PLCγ2 having leucine at amino acid position 845, or does not bind to nucleic acid encoding the wild-type PLCγ2 having aspartic acid at amino acid position 1140. In some embodiments, the system further comprises additional sequence specific nucleic acid probes, wherein the additional sequence specific nucleic acid probes bind to nucleic acids encoding a modified PLCγ2 that is modified at amino acid position 742, 845, or 1140 and at one or more additional positions.

Disclosed herein is a system of detecting a modified PLCγ2 that confers resistance to inhibition with an irreversible BTK inhibitor in a subject, comprising: (a) a sample containing a nucleic acid molecule encoding a PLCγ2 polypeptide from the subject; and (b) a pair of oligonucleotide primers that flank the nucleic acid region encoding amino acid 742, 845, or 1140 of a PLCγ2 polypeptide. In some embodiments, the modification in the PLCγ2 polypeptide is R742P, L845F, or D1140G. In some embodiments, the system further comprises additional oligonucleotide primers that flank nucleic acid regions encoding additional amino acid modifications of the PLCγ2 polypeptide.

Disclosed herein is a method of screening compounds that inhibit a modified PLCγ2, comprising: (a) providing a modified PLCγ2, wherein the modified PLCγ2 is modified at amino acid position corresponding to amino acid position 742, 845, or 1140 of the amino acid sequence set forth in SEQ ID NO: 2; (b) contacting the modified PLCγ2 with a test compound; and (c) detecting the level of PLCγ2 activity, wherein a decrease in activity indicates that the compound inhibits the modified PLCγ2. In some embodiments, the modification is a substitution, addition or deletion of the amino acid at position 742, 845, or 1140 of the PLCγ2 polypeptide. In some embodiments, the modification is a substitution of arginine to proline at amino acid position 742 of the PLCγ2 polypeptide. In some embodiments, the modification is a substitution of leucine to phenylalanine at amino acid position 845 of the PLCγ2 polypeptide. In some embodiments, the modification is a substitution of aspartic acid to glycine at amino acid position 1140 of the PLCγ2 polypeptide. In some embodiments, detecting the level of PLCγ2 activity is assessed by an in vitro assay. In some embodiments, the host cell stably expresses the modified PLCγ2 polypeptide. In some embodiments, the cell is deficient for the expression of endogenous wild-type PLCγ2. In some embodiments, the cell is chicken DT40 PLCγ2−/− B cell. In some embodiments, the cell is a non B-cell. In some embodiments, the cell is a mammalian non-B-cell. In some embodiments, the cell is a 293 cell. In some embodiments, the cell is a non-mammalian cell. In some embodiments, the cell is an inset cell, a bacterial cell, a yeast cell or a plant cell.

Disclosed herein is a method of assessing whether a subject who possess high-risk cytogenetic features is less responsive or likely to become less responsive to therapy with a BTK inhibitor, comprising: (a) testing a sample containing a nucleic acid molecule encoding a PLCγ2 polypeptide from the subject; (b) determining whether the encoded PLCγ2 polypeptide is modified at amino acid position corresponding to amino acid position 742, 845, or 1140 of the amino acid sequence set forth in SEQ ID NO: 2; and (c) characterizing the subject as resistant or likely to become resistant to therapy with a BTK inhibitor if the subject has the modification. In some embodiments, the subject has been administered a covalent and/or irreversible BTK inhibitor for treatment of a cancer. Disclosed herein is a method of monitoring whether a subject who possess high-risk cytogenetic features during the course of a therapy with a BTK inhibitor has developed or is likely to develop resistance to the therapy, comprising: (a) testing a sample containing a nucleic acid molecule encoding a PLCγ2 polypeptide from the subject; (b) determining whether the encoded PLCγ2 polypeptide is modified at amino acid position corresponding to amino acid position 742, 845, or 1140 of the amino acid sequence set forth in SEQ ID NO: 2; and (c) characterizing the subject as resistant or likely to become resistant to therapy with a BTK inhibitor if the subject has the modification. Disclosed herein is a method of optimizing the therapy with a BTK inhibitor of a subject who possess high-risk cytogenetic features, comprising: (a) testing a sample containing a nucleic acid molecule encoding a PLCγ2 polypeptide from the subject; (b) determining whether the encoded PLCγ2 polypeptide is modified at amino acid position corresponding to amino acid position 742, 845, or 1140 of the amino acid sequence set forth in SEQ ID NO: 2; and (c) discontinuing treatment with the BTK inhibitor if the subject has the modification or continuing treatment with the BTK inhibitor if the subject does not have the modification. In some embodiments, the PLCγ2 polypeptide is modified at additional amino acid positions. In some embodiments, the methods further comprise administering an inhibitor of PLCγ2 if the subject has one or more modifications with at least one modification at amino acid position 742, 845, or 1140 in the PLCγ2 polypeptide. In some embodiments, the methods further comprise administering an inhibitor of LYN, SYK, JAK, PI3K, MAPK, MEK or NFκB if the subject has at least the modification at amino acid position 742, 845, or 1140 in the PLCγ2 polypeptide. In some embodiments, the high-risk cytogenetic features comprise del(11q22.3), del(17p13.1) or complex karyotype. In some embodiments, the methods further comprise testing a sample containing the nucleic acid molecule encoding the PLCγ2 polypeptide and a nucleic acid molecule encoding an additional polypeptide. In some embodiments, the additional polypeptide is a BTK polypeptide. In some embodiments, the sample contains one or more cancer cells. In some embodiments, the sample contains ctDNA. In some embodiments, the sample is a sample obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the covalent and/or irreversible BTK inhibitor. In some embodiments, the methods further comprise testing a sample from the subject prior to treatment with the BTK inhibitor. In some embodiments, the BTK inhibitor is a covalent and/or irreversible BTK inhibitor. In some embodiments, the covalent and/or irreversible BTK inhibitor is selected from among ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK417891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the covalent and/or irreversible BTK inhibitor is ibrutinib. In some embodiments, the maintenance therapy regimen comprises administering the BTK inhibitor at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, the cancer is a hematologic cancer. In some embodiments, the cancer is a B-cell malignancy. In some embodiments, the cancer is selected from among a leukemia, a lymphoma, or a myeloma. In some embodiments, the cancer is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the B-cell malignancy is CLL. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

Disclosed herein is a kit comprising one or more reagents for the detection of a mutant PLCγ2 polypeptide, wherein the mutant PLCγ2 polypeptide comprises a modification at amino acid position 742, 845, or 1140 or a nucleic acid encoding a mutant PLCγ2 polypeptide comprising modification at amino acid position 742, 845, or 1140. In some embodiments, the kit comprises oligonucleotide primer pairs that flank the nucleic acid region encoding amino acid 742, 845, or 1140 of the PLCγ2 polypeptide. In some embodiments, the kit comprises oligonucleotide primers that (a) bind to nucleic acid encoding a modified PLCγ2 that is modified at amino acid position 742, 845, or 1140; and (b) do not bind to nucleic acid encoding the wild-type PLCγ2 having arginine at amino acid position 742, or do not bind to nucleic acid encoding the wild-type PLCγ2 having leucine at amino acid position 845, or do not bind to nucleic acid encoding the wild-type PLCγ2 having aspartic acid at amino acid position 1140. In some embodiments, the kit comprises a microchip comprising (a) a modified PLCγ2 polypeptide, wherein the modified PLCγ2 polypeptide has modifications at amino acid position 742, 845, or 1140; or (b) a nucleic acid molecule encoding a mutant PLCγ2 polypeptide, wherein the mutant PLCγ2 polypeptide has a modification at amino acid position 742, 845, or 1140 or a portion thereof comprising a modification at amino acid position 742, 845, or 1140. In some embodiments, the kit further comprises one or more reagents for the detection of a mutant PLCγ2 polypeptide, wherein the mutant PLCγ2 polypeptide comprises a modification at amino acid position 742, 845, or 1140 and one or more additional modifications.

BRIEF DESCRIPTION OF THE DRAWINGS

FIG. 8 illustrates baseline characteristics associated with study discontinuation among patients with progressive disease (e.g., CLL, Richter's) or discontinuations for a non-progressive disease reason (e.g., infection, toxicity or other).

FIG. 9 illustrates the identification of BTK and PLCγ2 mutations in patients that experienced relapse on the Ibrutinib therapy.

DETAILED DESCRIPTION OF THE INVENTION

Figure 1:
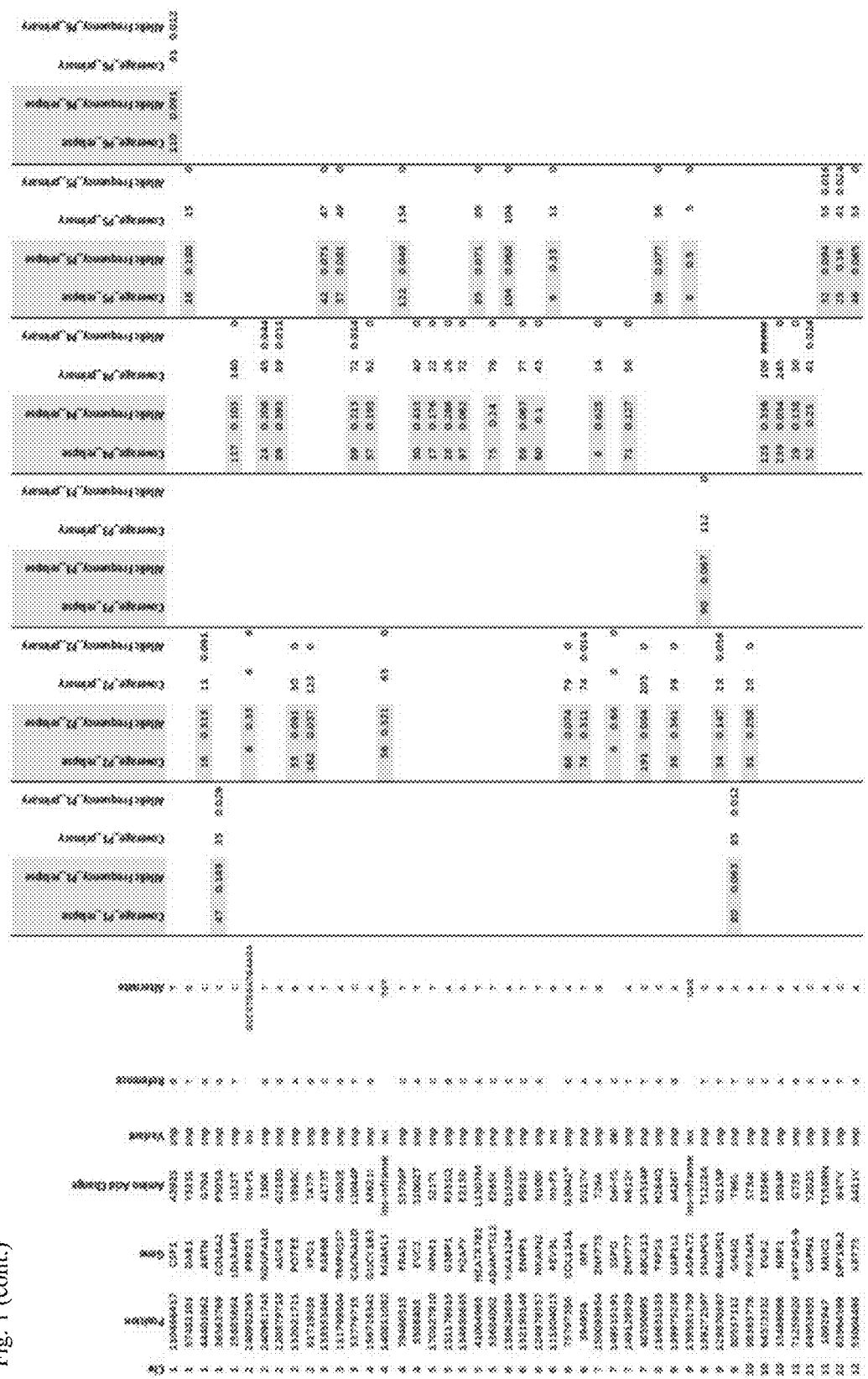
FIG. 1 illustrates characteristics of ibrutinib resistant patients. Whole exome sequencing (WES) was performed on samples from six patients. *Includes FISH for del (17p13.1), del(11q22.3), centromere 12, and del(13q14.3) and complexity determined by stimulated banded metaphase analysis. **A complete list of functional mutations found only at relapse is shown.
Figure 1:
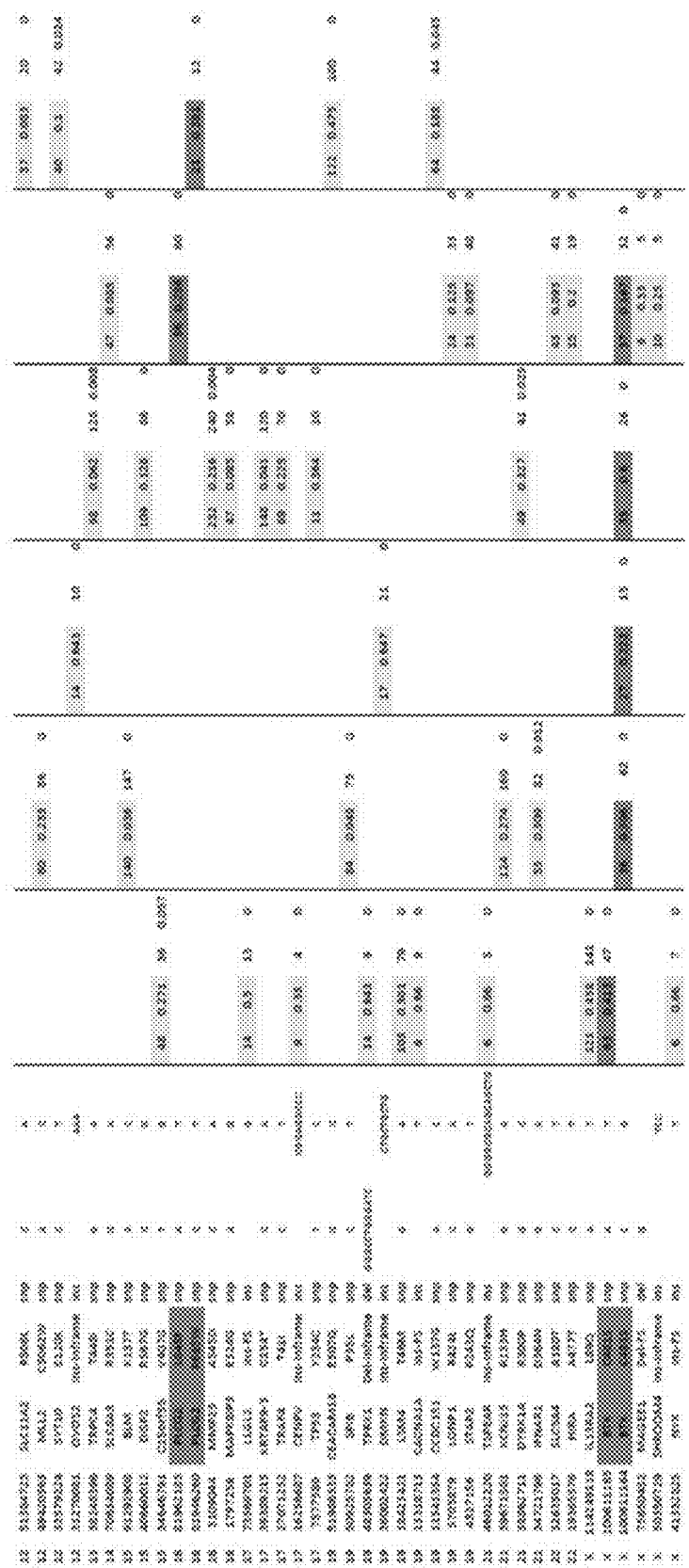

Drug resistance is a problem affecting several areas of medicine including infectious diseases and cancer. During the course of cancer treatment, spontaneous random mutations occur as the cancer cell population expands by repeated divisions, some of which confer resistance and hence a survival advantage. The acquisition of a resistance mutation has been described for all major tyrosine kinase inhibitors in oncology, including imatinib (Gleevec), and the EGFR inhibitors gefitinib, and erlotinib. The emergence of resistance associated mutations forces patients to go on to other therapies including dasatinib, nilotinib, etc., but many of these eventually relapse with new resistance mutations. In lung cancer, erlotinib and gefitinib have produced impressive and durable clinical results, but nearly all become ineffective within 12-18 months due to resistance. ~50% of these resistant patients have a mutation in the target kinase (EGFR) called T790M, which changes a single amino acid.

Described herein are mutations in PLCγ2 gene that arose during treatment with the irreversible BTK inhibitor ibrutinib. In some embodiments, the mutation results in a modified PLCγ2 polypeptide that contain an amino acid substitution at amino acid position 742, 845, or 1140 of the wild-type PLCγ2 (e.g., R742P, L845F, D1140G). In some embodiments, the presence of such mutation signals a development of resistance with BTK inhibitor treatment such as ibrutinib. Also described herein, in some embodiments, are modified PLCγ2 polypeptides that contain an amino acid substitution at amino acid position 742, 845, or 1140 of the wild-type PLCγ2 (e.g., R742P, L845F, D1140G) and nucleic acids encoding the polypeptides.

As described herein, in some embodiments, subjects are screened for the identification of a mutation at amino acid position 742, 845, or 1140 in PLCγ2. In some embodiments, the subjects possess high-risk cytogenetic features (e.g., del(11q22.3), del(17p13.1) or complex karyotype). In some embodiments, identification of mutation in PLCγ2 allows for the prescription of a cancer treatment or modification of a cancer treatment. In some embodiments, identification of such a mutation is used to stratify subjects for a particular therapy, such as for example, therapy with an inhibitor that inhibits the activity of the mutant PLCγ2 (e.g., a PLCγ2 inhibitor). In some embodiments, identification of such a mutation is used to characterize a subject as having a high risk of relapse of a BTK-mediated disease or condition, such as, for example, a hematologic cancer, such as a B-cell cancer. In some embodiments, identification of such a mutation is used to characterize a subject as lacking responsiveness to particular BTK inhibitor, such as for example a covalent and/or irreversible BTK inhibitor, such as ibrutinib.

As described herein, in some embodiments, subjects are monitored throughout the course of a therapeutic regimen for the development of the mutation in PLCγ2 at amino acid position 742, 845, or 1140. In some embodiments, the therapeutic regimen is a maintenance therapeutic regimen. In some embodiments, the therapeutic regimen is optimized based on the identification of the mutation in PLCγ2.

Also described herein, in some embodiments, are designs and screening of inhibitors effective for inhibition of a mutant PLCγ2 having one or more resistance mutations with at least one mutation at amino acid position 742, 845, or 1140. Such inhibitors are useful in clinical and therapeutic applications. In some embodiments, the inhibitors are useful for the treatment of a cancer, such as for example, a hematologic cancer, such as a B-cell malignancy.

Further described herein, in some embodiments, are methods of compositions, combinations and kits containing the modified PLCγ2 nucleic acids and polypeptides described herein and reagents for detection of the modified PLCγ2 nucleic acids and polypeptides described herein. Also provided are methods of using the modified PLCγ2 polypeptides for identifying mutant PLCγ2 interacting molecules, including PLCγ2 inhibitors. Also provided are methods of producing the modified PLCγ2 nucleic acids and polypeptides described herein.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µg" means "about 5 µg" and also "5 µg." Generally, the term "about" includes an amount that would be expected to be within experimental error.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

As used herein, the term "BTK inhibitor" or "BTK antagonist" refers to an agent that inhibits or reduces at least one activity of a BTK polypeptide. BTK activities include direct and indirect activities. Exemplary direct activities include, but are not limited to, association with a target molecule or phosphorylation of a target substrate (i.e. kinase activity). Exemplary indirect activities include, but are not limited to, activation or inhibition of a downstream biological event, such as for example activation of NF-κB-mediated gene transcription.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible BTK inhibitor," as used herein, refers to an inhibitor of BTK that can form a covalent bond with an amino acid residue of BTK. In one embodiment, the irreversible inhibitor of BTK can form a covalent bond with a Cysteine residue of BTK; in particular embodiments, the irreversible inhibitor can form a covalent bond with a Cysteine 481 residue (or a homolog thereof) of BTK or a cysteine residue in the homologous corresponding position of another tyrosine kinase.

As used herein, inhibition of BTK activity refers any decrease in BTK activity in the presence of an inhibitor compared to the same activity in the absence of the inhibitor.

As used herein, the term "PLCγ2 inhibitor" refers to an agent that inhibits at least one activity of a PLCγ2 polypeptide containing an amino acid modification at position 742, 845, or 1140. In some embodiments, the agent inhibits at least one activity of a PLCγ2 polypeptide containing two or more amino acid modifications at positions selected from 742, 845, or 1140 and one or more additional positions. In some embodiments, the PLCγ2 inhibitor also inhibits the activity of a wild-type PLCγ2 polypeptide. In some embodiments, the PLCγ2 inhibitor does not inhibit the activity of a wild-type PLCγ2 polypeptide.

As used herein, "maintenance therapy" means the ongoing use of chemotherapy or another treatment to assist in lowering the risk of recurrence (return of cancer) following a beneficial response to initial therapy, for example remission. Maintenance therapy also may be used for patients with advanced cancer (e.g., cancer that cannot be cured) to help keep it from growing and spreading further.

The terms "cancer" and "cancerous" refer to or describe the physiological condition in mammals that is typically characterized by unregulated cell growth. Examples of cancer include, but are not limited to, B-cell lymphoproliferative disorders (BCLDs), such as lymphoma and leukemia, and solid tumors. By "B cell-related cancer" or "cancer of B-cell lineage" is intended any type of cancer in which the dysregulated or unregulated cell growth is associated with B cells.

By "refractory" in the context of a cancer is intended the particular cancer is resistant to, or non-responsive to, therapy with a particular therapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (e.g., phosphorothioates, phosphoroamidates). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; and Cassol et al. (1992) *Mol. Cell. Probes* 6, 327-331; and Rossolini et al. (1994) *Mol. Cell. Probes* 8:91-98).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide", peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, modification in reference to modification of a sequence of amino acids of a polypeptide or a sequence of nucleotides in a nucleic acid molecule and includes deletions, insertions, and replacements of amino acids and nucleotides, respectively.

To determine percent homology between two sequences, the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877 is used. Such an algorithm is incorporated into the NBLAST and XBLAST programs of Altschul, et al. (1990) *J. Mol. Biol.* 215:403-410. BLAST nucleotide searches are performed with the NBLAST program, score=100, wordlength=12 to obtain nucleotide sequences homologous to a nucleic acid molecules described or disclose herein. BLAST protein searches are performed with the)(BLAST program, score=50, wordlength=3. To obtain gapped alignments for comparison purposes, Gapped BLAST is utilized as described in Altschul et al. (1997) *Nucleic Acids Res.* 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 91%, 92%, 93%, 94%, 95%, 96%, 97%, 98%, 99%, or 100% identical to the amino acid sequence of any protein described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). The BLOSUM62 table is an amino acid substitution matrix derived from about 2,000 local multiple alignments of protein sequence segments, representing highly conserved regions of more than 500 groups of related proteins (Henikoff et al (1992) *Proc. Natl. Acad. Sci. USA,* 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

As used herein, corresponding residues refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. In other instances, corresponding regions can be identified.

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, the subject can be any animal, including mammals (e.g., a human or non-human animal) and non-mammals. In one embodiment of the methods and compositions provided herein, the mammal is a human.

As used herein, the terms "treat," "treating" or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. In a non-limiting example, for prophylactic benefit, a third-generation BTK inhibitor compound disclosed herein is administered to an individual at risk of developing a particular disorder, predisposed to developing a particular disorder, or to an individual reporting one or more of the physiological symptoms of a disorder. In some embodiments, a third-generation BTK inhibitor compound disclosed herein is administered to a subject following treatment with one or more therapeutic agents. In some embodiments, a third-generation BTK inhibitor compound disclosed herein is administered to a subject in combination with treatment with one or more therapeutic agents.

As used herein, "contacting" refers to refers to the act of touching, making contact, or of bringing substances into immediate proximity. "Contacting" can be achieved by mixing the components in a fluid or semi-fluid mixture.

Mutant PLCγ2 Polypeptides

Provided herein are mutant PLCγ2 polypeptides. In some embodiments, the mutant PLCγ2 polypeptides are isolated mutant PLCγ2 polypeptides. In some embodiments, the isolated mutant PLCγ2 polypeptides are non-native mutant PLCγ2 polypeptides. In some embodiments, the mutant PLCγ2 polypeptides are recombinant proteins. In some embodiments, the mutant PLCγ2 polypeptides are purified from a host cell. In some embodiments, the mutant PLCγ2 polypeptides comprise one or more mutations (e.g., substitution, deletion or addition). In some embodiments, one or more mutations in the mutant PLCγ2 polypeptides result in resistance of a patient to treatment with a BTK inhibitor. In some embodiments, the one or more mutations are gain of function mutations in PLCγ2. In some embodiments, the one or more mutations result in constitutive activation of PLCγ2. In some embodiments, constitutive activation of PLCγ2 results in mobilization of intracellular calcium, activation of extracellular signal-regulated kinase (ERK) and c-Jun NH2-terminal kinase (JNK) mitogen-activated protein kinase (MAPK) pathways.

In some embodiments, the mutation results in a modification at an amino acid position corresponding to amino acid position 742, 845, or 1140 of the amino acid sequence set forth in SEQ ID NO: 2. In some embodiments, the mutation is a frame shift mutation that results in a modification at an amino acid position corresponding to amino acid position 742, 845, or 1140 of the amino acid sequence set forth in SEQ ID NO: 2. In some embodiments, the mutation is a frame shift mutation at that results in a truncation of the PLCγ2 polypeptide at or following amino acid position 742, 845, or 1140 of the amino acid sequence set forth in SEQ ID NO: 2.

Provided herein is an isolated PLCγ2 polypeptide or a variant thereof having PLCγ2 activity comprising multiple mutations. In some embodiments, the isolated PLCγ2 polypeptide comprises 1, 2, 3, 4, 5, 6, 7, 8, 9, 10, 15, 20, 25, 30 or more mutations. In some embodiments, the isolated PLCγ2 polypeptide comprises one mutation. In some embodiments, the mutations result in modifications at amino acid positions corresponding to amino acid position 742, 845, or 1140 of the amino acid sequence set forth in SEQ ID NO: 2.

In some embodiments, the modification comprises a substitution, an addition or a deletion of the amino acid at amino acid position 742, 845, or 1140 compared to a wild type PLCγ2 set forth in SEQ ID NO: 2. In some embodiments, the modification comprises substitution of the amino acid at position 742, 845, or 1140 compared to a wild type PLCγ2 set forth in SEQ ID NO: 2.

In some embodiments, the modification is a substitution of arginine at position 742 to an amino acid selected from among leucine, isoleucine, valine, alanine, glycine, methionine, cysteine, serine, threonine, phenylalanine, tryptophan, lysine, histidine, proline, tyrosine, asparagine, glutamine, aspartic acid and glutamic acid at amino acid position 742 of the PLCγ2 polypeptide. In some embodiments, the modification is a substitution of arginine to proline at amino acid position 742 of the PLCγ2 polypeptide. In some embodiments, the substitution is R742P.

In some embodiments, the modification is a substitution of leucine at position 845 to an amino acid selected from among isoleucine, valine, alanine, glycine, methionine, cysteine, serine, threonine, phenylalanine, tryptophan, lysine, arginine, histidine, proline, tyrosine, asparagine, glutamine, aspartic acid and glutamic acid at amino acid position 845 of the PLCγ2 polypeptide. In some embodiments, the modification is a substitution of leucine to phenylalanine, tyrosine or tryptophan at amino acid position 845 of the PLCγ2 polypeptide. In some embodiments, the modification is a substitution of leucine to phenylalanine at amino acid position 845 of the PLCγ2 polypeptide. In some embodiments, the substitution is L845F.

In some embodiments, the modification is a substitution of aspartic acid at position 1140 to an amino acid selected from among leucine, isoleucine, valine, alanine, glycine, methionine, cysteine, serine, threonine, phenylalanine, tryptophan, lysine, arginine, histidine, proline, tyrosine, asparagine, glutamine, and glutamic acid at amino acid position 1140 of the PLCγ2 polypeptide. In some embodiments, the modification is a substitution of aspartic acid to glycine at amino acid position 1140 of the PLCγ2 polypeptide. In some embodiments, the substitution is D1140G.

In some embodiments, the mutant PLCγ2 polypeptide comprises a modification at amino acid position 742, 845, or 1140 and a modification at one or more additional amino acid positions. In some embodiments, the modification at one or more additional amino acid positions comprise 1, 2, 3, 4, 5, 6, 7, 8, 9, 10, 11, 12, 13, 14, 15, 16, 17, 18, 19, 20 or more amino acid positions. In some embodiments, the modification at amino acid position 742 is a substitution that is R742P. In some embodiments, the modification at amino acid position 845 is a substitution that is L845F. In some embodiments, the modification at amino acid position 1140 is a substitution that is D1140G.

In some embodiments, the mutant PLCγ2 polypeptide comprises a substitution of the amino acid at position 742, 845, or 1140 compared to a wild type PLCγ2 set forth in SEQ ID NO: 2 and one or more additional amino acid substitutions. In some embodiments, the mutant PLCγ2 polypeptide comprises the sequence of amino acids comprising a substitution of the amino acid at position 742, 845, or 1140 or a variant that has at least or at least about 60%, 65%, 70%, 75%, 80%, 85%, 90%, 95%, 96%, 97%, 98%, 99% or more sequence identity with the polypeptide having the sequence set forth in SEQ ID NO: 2.

In some embodiments, the mutant PLCγ2 polypeptide comprises a substitution of the amino acid at position 742, 845, or 1140 compared to a wild type PLCγ2 set forth in SEQ ID NO: 2 and one or more additional amino acid substitutions selected from among a substitution of the amino acid at position 665 or 707 compared to a wild type PLCγ2 set forth in SEQ ID NO: 2. In some embodiments, the mutant PLCγ2 polypeptide comprises a substitution of the amino acid at position 742, 845, or 1140 compared to a wild type PLCγ2 set forth in SEQ ID NO: 2 and one or more additional amino acid substitutions selected from among R665W, S707F, S707P, and S707Y. In some embodiments, the mutant PLCγ2 polypeptide comprises an amino acid substitution selected from among R742P, L845F, D1140G and one or more additional amino acid substitutions selected from among R665W, S707F, S707P, and S707Y. In some embodiments, the mutant PLCγ2 polypeptide comprises one or more amino acid substitutions selected from among R742P, L845F, D1140G, R665W, S707F, S707P, and S707Y.

In some embodiments, the mutant PLCγ2 polypeptide comprises a portion of the mutant PLCγ2 polypeptide set forth in SEQ ID NO: 2. In some embodiments, the portion exhibits an activity of a PLCγ2 polypeptide. In some embodiments, the portion comprises one or more domains of the PLCγ2 polypeptide. The PLCγ2 polypeptide comprises two SH2 domains and one SH3 domain. In some embodiments, the two SH2 domains comprise amino acid positions 498-636 and 636-744 set forth in SEQ ID NO: 2. In some embodiments, the SH3 domain comprises amino acid positions 762-877 set forth in SEQ ID NO: 2. In some embodiments, the mutant PLCγ2 polypeptide comprises one or both SH2 domains and SH3 domain of the PLCγ2 polypeptide comprising the modification at amino acid position 742, 845, or 1140 of the mutant PLCγ2 polypeptide set forth in SEQ ID NO: 2.

In some embodiments, a PLCγ2 polypeptide is a fusion protein comprising the domains of a PLCγ2 polypeptide comprising the modifications at amino acid position 742, 845, or 1140 of the mutant PLCγ2 polypeptide set forth in SEQ ID NO: 2 linked to a heterologous polypeptide. Methods for the generation of fusion proteins are known in the art and include standard recombinant DNA techniques. For example, in some embodiments, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In some embodiments, the fusion gene can be synthesized by conventional techniques including automated DNA synthesizers. In some embodiments, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). In some embodiments, expression vectors are commercially available that encode a fusion moiety (e.g., a GST polypeptide). A nucleic acid encoding a modified PLCγ2 polypeptide can be cloned into such an expression vector such that the fusion moiety is linked in-frame to the modified PLCγ2 polypeptide.

In some embodiments, a PLCγ2 polypeptide comprising modifications at amino acid position 742, 845, or 1140 of the wild-type PLCγ2 polypeptide set forth in SEQ ID NO: 2 linked to a peptide tag. In some embodiments, the peptide tag is an epitope tag recognized by a tag-specific antibody. In some embodiments the tag is an epitope tag, such as, but not limited to a c-myc, V-5, hemagglutinin (HA), FLAG, tag. In some embodiments the tag is an affinity tag, such as, but not limited to, biotin, strep-tag, chitin binding protein (CBP), maltose binding protein (MBP), glutathione-S-transferase (GST), or a poly(His) tag. In some embodiments, a PLCγ2 polypeptide comprising modifications at amino acid position 742, 845, or 1140 of the wild-type PLCγ2 polypeptide set forth in SEQ ID NO: 2 linked to a detectable protein or moiety, such a luminescent, chemiluminescent, bioluminescent, or fluorescent protein or moiety. In some embodiments, the fluorescent protein is a green (GFP), red (RFP), cyan (CFP), yellow (YFP), or blue (BFP) fluorescent protein. In some embodiments, a PLCγ2 polypeptide comprising modifications at amino acid position 742, 845, or 1140 of the wild-type PLCγ2 polypeptide set forth in SEQ ID NO: 2 linked to an enzyme for example, a luciferase or a beta-galactosidase.

In some embodiments, provided herein is an array comprising a mutant PLCγ2 polypeptide provided herein. In some embodiments, the mutant PLCγ2 polypeptide is bound to a microchip. In some embodiments, the mutant PLCγ2 polypeptide is bound directly to the microchip. In some embodiments, the mutant PLCγ2 polypeptide is bound indirectly to the microchip via a linker. In some embodiments, provided herein is a microchip array comprising a mutant PLCγ2 polypeptide provided herein.

In some embodiments, the mutant PLCγ2 polypeptide contains one or more amino acid substitutions that confer resistance to inhibition by a BTK inhibitor. In some embodiments, the one or more amino acid substitutions comprise the substitution at amino acid position 742, 845, or 1140. In some embodiments, the mutant PLCγ2 polypeptide contains one or more amino acid substitutions that confer resistance to inhibition by a covalent and/or irreversible BTK inhibitor that is ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK417891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the mutant PLCγ2 polypeptide contains one or more amino acid substitutions that confer resistance to inhibition by a covalent and/or irreversible BTK inhibitor that is ibrutinib, PCI-45292, PCI-45466, AVL-101, AVL-291, AVL-292, ONO-WG-37 or (R)-6-amino-9-(1-but-2-ynoylpyrrolidin-3-yl)-7-(4-phenoxyphenyl)-7H-purin-8(9H)-one. In some embodiments, the mutant PLCγ2 polypeptide contain one or more amino acid substitutions with at least one substitution at amino acid position 742, 845, or 1140 that confer resistance to inhibition by a covalent and/or irreversible BTK inhibitor that is ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the mutant PLCγ2 polypeptide contain one or more amino acid substitutions with at least one substitution at amino acid position 742, 845, or 1140 that confer resistance to inhibition by a covalent and/or irreversible BTK inhibitor that is ibrutinib, PCI-45292, PCI-45466, AVL-101, AVL-291, AVL-292, ONO-WG-37 or (R)-6-amino-9-(1-but-2- ynoylpyrrolidin-3-yl)-7-(4-phenoxyphenyl)-7H-purin-8 (9H)-one. In some embodiments, the mutant PLCγ2 polypeptide containing the substitution at amino acid position 742, 845, or 1140 that confer resistance to inhibition by a covalent and/or irreversible BTK inhibitor that is ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK417891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the mutant PLCγ2 polypeptide containing the substitution at amino acid position 742, 845, or 1140 that confer resistance to inhibition by a covalent and/or irreversible BTK inhibitor that is ibrutinib, PCI-45292, PCI-45466, AVL-101, AVL-291, AVL-292, ONO-WG-37 or (R)-6-amino-9-(1-but-2-ynoylpyrrolidin-3-yl)-7-(4-phenoxyphenyl)-7H-purin-8(9H)-one. In some embodiments, the covalent and/or irreversible BTK inhibitor is ibrutinib. In some embodiments, the covalent and/or irreversible BTK inhibitor is (R)-6-amino-9-(1-but-2-ynoylpyrrolidin-3-yl)-7-(4-phenoxyphenyl)-7H-purin-8 (9H)-one.

Nucleic Acids Encoding Mutant PLCγ2 Polypeptides

Provided herein are nucleic acids encoding mutant PLCγ2 polypeptides. Provided herein are nucleic acids encoding any of the mutant PLCγ2 polypeptides described herein. Methods for deducing nucleic acids that encode particular polypeptides are known in the art and involve standard molecular biology techniques. Exemplary nucleic acids encoding mutant PLCγ2 polypeptides provided herein are provided. It is understood that due to the degeneracy of the genetic code multiple variants nucleic acids exist that encode the same polypeptide. Nucleic acids that encode the mutant PLCγ2 polypeptides provided herein encompass such variants. In some embodiments, the mutant PLCγ2 nucleic acids are synthetic nucleic acids. In some embodiments, the mutant PLCγ2 nucleic acids are cDNA molecules. In some embodiments, the mutant PLCγ2 nucleic acids do not contain genomic DNA. In some embodiments, the mutant PLCγ2 nucleic acids are unmethylated. In some embodiments, the mutant PLCγ2 nucleic acids do not contain PLCγ2 genomic intron sequences. In some embodiments, the mutant PLCγ2 nucleic acids comprise a sequence of nucleotides from two or more exons of the PLCγ2 genomic sequence, including nucleic acid comprising the codon sequence encoding position 742, 845, or 1140 of the PLCγ2 polypeptide. In some embodiments, the mutant PLCγ2 nucleic acids comprise a sequence of nucleotides that encode a proline at a position corresponding to position 742 of the wild-type PLCγ2 polypeptide. In some embodiments, the mutant PLCγ2 nucleic acids comprise a sequence of nucleotides that encode a phenylalanine at a position corresponding to position 845 of the wild-type PLCγ2 polypeptide. In some embodiments, the mutant PLCγ2 nucleic acids comprise a sequence of nucleotides that encode a glycine at a position corresponding to position 1140 of the wild-type PLCγ2 polypeptide.$$

In some embodiments, the nucleic acid encoding a modified PLCγ2 polypeptide provided herein is a DNA or an RNA molecule.

In some embodiments, the nucleic acid encoding a mutant PLCγ2 polypeptide comprises a modification where the encoded polypeptide comprises a substitution of the amino acid proline at a position corresponding to position 742 of the wild-type PLCγ2 polypeptide set forth in SEQ ID NO: 2. In some embodiments, the nucleic acid encoding a mutant PLCγ2 polypeptide comprises one or more modifications where the encoded polypeptide comprises substitutions at position corresponding to amino acid position 742 and at one or more additional positions of the wild-type PLCγ2 polypeptide set forth in SEQ ID NO: 2. In some embodiments, the nucleic acid comprises the sequence of nucleic acids set forth in SEQ ID NO: 1, wherein the nucleic acid codon encoding amino acid at position 742 is modified, whereby the codon does not encode arginine, or a variant that has at least or at least about 60%, 70%, 75%, 80%, 85%, 90%, 95%, 96%, 97%, 98%, 99% or more sequence identity with the polypeptide having the sequence set forth in SEQ ID NO: 2.

In some embodiments, the nucleic acid encoding a mutant PLCγ2 polypeptide comprises a modification where the encoded polypeptide comprises a substitution of the amino acid phenylalanine at a position corresponding to position 845 of the wild-type PLCγ2 polypeptide set forth in SEQ ID NO: 2. In some embodiments, the nucleic acid encoding a mutant PLCγ2 polypeptide comprises one or more modifications where the encoded polypeptide comprises substitutions at position corresponding to amino acid position 845 and at one or more additional positions of the wild-type PLCγ2 polypeptide set forth in SEQ ID NO: 2. In some embodiments, the nucleic acid comprises the sequence of nucleic acids set forth in SEQ ID NO: 1, wherein the nucleic acid codon encoding amino acid at position 845 is modified, whereby the codon does not encode leucine, or a variant that has at least or at least about 60%, 70%, 75%, 80%, 85%, 90%, 95%, 96%, 97%, 98%, 99% or more sequence identity with the polypeptide having the sequence set forth in SEQ ID NO: 1.

In some embodiments, the nucleic acid encoding a mutant PLCγ2 polypeptide comprises a modification where the encoded polypeptide comprises a substitution of the amino acid glycine at a position corresponding to position 1140 of the wild-type PLCγ2 polypeptide set forth in SEQ ID NO: 2. In some embodiments, the nucleic acid encoding a mutant PLCγ2 polypeptide comprises one or more modifications where the encoded polypeptide comprises substitutions at position corresponding to amino acid position 1140 and at one or more additional positions of the wild-type PLCγ2 polypeptide set forth in SEQ ID NO: 2. In some embodiments, the nucleic acid comprises the sequence of nucleic acids set forth in SEQ ID NO: 1, wherein the nucleic acid codon encoding amino acid at position 1140 is modified, whereby the codon does not encode aspartic acid, or a variant that has at least or at least about 60%, 70%, 75%, 80%, 85%, 90%, 95%, 96%, 97%, 98%, 99% or more sequence identity with the polypeptide having the sequence set forth in SEQ ID NO: 1.

In some embodiments the nucleic acid modification is a missense mutation or a deletion of one or more codons that encode the PLCγ2 polypeptide. In some embodiments, the modification is a missense mutation that changes the nucleic acid codon that encodes arginine at amino position 742 of the PLCγ2 polypeptide. In some embodiments, the modification is a missense mutation that changes the nucleic acid codon that encodes leucine at amino position 845 of the PLCγ2 polypeptide. In some embodiments, the modification is a missense mutation that changes the nucleic acid codon that encodes aspartic acid at amino position 1140 of the PLCγ2 polypeptide.

In some embodiments the nucleic acid modification is a frame shift mutation or a deletion of one or more codons that encode the PLCγ2 polypeptide. In some embodiments, the modification is a frame shift mutation that changes the nucleic acid codon that encodes arginine at amino position 742 of the PLCγ2 polypeptide. In some embodiments, the modification is a missense mutation that changes the nucleic acid codon that encodes leucine at amino position 845 of the PLCγ2 polypeptide. In some embodiments, the modification is a frame shift mutation that changes the nucleic acid codon that encodes aspartic acid at amino position 1140 of the PLCγ2 polypeptide.

In some embodiments, the nucleic acid codon that encodes arginine at amino position 742 of the PLCγ2 polypeptide is CGT, CGC, CGA, CGG, AGA or AGG. In some embodiments, the modification changes the nucleic acid codon that encodes arginine at amino position 742 of the PLCγ2 polypeptide to a nucleic acid codon that encodes proline. In some embodiments, the nucleic acid codon that encodes proline is CCT, CCC, CCA, or CCG.

In some embodiments, the nucleic acid codon that encodes leucine at amino position 845 of the PLCγ2 polypeptide is TTA, TTG, CTT, CTC, CTA or CTG. In some embodiments, the modification changes the nucleic acid codon that encodes leucine at amino position 845 of the PLCγ2 polypeptide to a nucleic acid codon that encodes Phenylalanine. In some embodiments, the nucleic acid codon that encodes Phenylalanine is TTT or TTC.

In some embodiments, the nucleic acid codon that encodes aspartic acid at amino position 1140 of the PLCγ2 polypeptide is GAT or GAC. In some embodiments, the modification changes the nucleic acid codon that encodes aspartic acid at amino position 1140 of the PLCγ2 polypeptide to a nucleic acid codon that encodes glycine. In some embodiments, the nucleic acid codon that encodes glycine is GGT, GGC, GGA, or GGG.

In some embodiments, the nucleic acid provided herein encoding a mutant PLCγ2 polypeptide is an isolated nucleic acid. In some embodiments, the nucleic acid provided herein encoding a mutant PLCγ2 polypeptide is a DNA molecule. In some embodiments, the nucleic acid provided herein encoding a mutant PLCγ2 polypeptide is a cDNA molecule. In some embodiments, the nucleic acid provided herein encoding a mutant PLCγ2 polypeptide is an RNA molecule. In some embodiments, the nucleic acid provided herein encoding a mutant PLCγ2 polypeptide is an inhibitory RNA molecule (i.e. RNAi). In some embodiments, the nucleic acid provided herein is a nucleic acid molecule that is complementary, or binds to, a nucleic acid encoding a mutant PLCγ2 polypeptide.

In some embodiments, the nucleic acid provided herein encoding a mutant PLCγ2 polypeptide encodes a portion of a mutant PLCγ2 polypeptide provided herein that comprises amino acid position 742, 845, or 1140. In some embodiments, the nucleic acid provided herein encoding a mutant PLCγ2 polypeptide encodes a portion of a mutant PLCγ2 polypeptide provided herein that comprises amino acid position 742, 845, or 1140. In some embodiments, the nucleic acid provided herein encoding a mutant PLCγ2 polypeptide encodes one or more domains of a mutant PLCγ2 polypeptide provided herein. In some embodiments, the nucleic acid provided herein encoding a mutant PLCγ2 polypeptide encodes one or both SH2 domains and SH3 domain of a mutant PLCγ2 polypeptide provided herein.

In some embodiments, the nucleic acid provided herein encoding a mutant PLCγ2 polypeptide or a portion thereof contains nucleic acid encoding an amino acid at position 742 that is not arginine. In some embodiments, the nucleic acid provided herein encoding a mutant PLCγ2 polypeptide or a portion thereof contains nucleic acid encoding proline at amino acid position 742. In some embodiments, the nucleic acid provided herein encoding a mutant PLCγ2 polypeptide or a portion thereof contains nucleic acid encoding amino acids at position 742.

In some embodiments, the nucleic acid provided herein encoding a mutant PLCγ2 polypeptide or a portion thereof contains nucleic acid encoding an amino acid at position 845 that is not leucine. In some embodiments, the nucleic acid provided herein encoding a mutant PLCγ2 polypeptide or a portion thereof contains nucleic acid encoding phenylalanine at amino acid position 845. In some embodiments, the nucleic acid provided herein encoding a mutant PLCγ2 polypeptide or a portion thereof contains nucleic acid encoding amino acids at position 845.

In some embodiments, the nucleic acid provided herein encoding a mutant PLCγ2 polypeptide or a portion thereof contains nucleic acid encoding an amino acid at position 1140 that is not aspartic acid. In some embodiments, the nucleic acid provided herein encoding a mutant PLCγ2 polypeptide or a portion thereof contains nucleic acid encoding glycine at amino acid position 1140. In some embodiments, the nucleic acid provided herein encoding a mutant PLCγ2 polypeptide or a portion thereof contains nucleic acid encoding amino acids at position 1140.

In some embodiments, the nucleic acid provide herein is an oligonucleotide that encodes a portion of the mutant PLCγ2 polypeptide. In some embodiments the nucleic acid provided herein is an oligonucleotide that encodes a portion of the mutant PLCγ2 polypeptide that contains a nucleotide codon encoding the amino acid corresponding to amino acid positions 742, 845, or 1140. In some embodiments, the codon encoding the amino acid corresponding to amino acid position 742 encodes an amino acid that is not arginine. In some embodiments, the codon encoding the amino acid corresponding to amino acid position 742 encodes an amino acid that is proline. In some embodiments, the codon encoding the amino acid corresponding to amino acid position 845 encodes an amino acid that is not leucine. In some embodiments, the codon encoding the amino acid corresponding to amino acid position 845 encodes an amino acid that is phenylalanine. In some embodiments, the codon encoding the amino acid corresponding to amino acid position 1140 encodes an amino acid that is not aspartic acid. In some embodiments, the codon encoding the amino acid corresponding to amino acid position 1140 encodes an amino acid that is glycine.

In some embodiments, the nucleic acid provided herein is a vector that comprises a nucleic acid molecule encoding a modified PLCγ2 polypeptide provided herein. In some embodiments, the nucleic acid provided herein is a vector that comprises nucleic acid encoding a mutant PLCγ2 polypeptide provided herein is an expression vector. In some embodiments, the nucleic acid encoding a mutant PLCγ2 polypeptide provided herein is operably linked to a promoter. In some embodiments, the promoter is a constitutive or an inducible promoter. In some embodiments, provided herein is a host cell, comprising the vector or nucleic acid molecule encoding a modified PLCγ2 polypeptide provided herein. In some embodiments, the cell is a prokaryotic cell or a eukaryotic cell. Also provided herein is a mutant PLCγ2 polypeptide expressed by the host cell.

In some embodiments, the vector is a viral or plasmid vector. In some embodiments, the viral vector is a DNA or RNA viral vector. Exemplary viral vectors include, but are not limited to, a vaccinia, adenovirus, adeno-associated virus (AAV), retrovirus, or herpesvirus vector.

In some embodiments, provided herein is an array comprising a nucleic acid encoding any of the mutant PLCγ2 polypeptides provided herein. In some embodiments, the mutant PLCγ2 nucleic acid is bound to a microchip. In some embodiments, the mutant PLCγ2 nucleic acid is bound directly to the microchip. In some embodiments, the mutant PLCγ2 nucleic acid is bound indirectly to the microchip via a linker. In some embodiments, provided herein is a microchip array comprising a nucleic acid encoding any of the mutant PLCγ2 polypeptides provided herein.

Diagnostic Methods

Described herein, in certain embodiments, are diagnostic methods that involve the detection of a mutant PLCγ2 polypeptide in a subject or a nucleic acid encoding a mutant PLCγ2 polypeptide in a subject. In some embodiments, the subject has a BTK-mediated disease or condition. In some embodiments, the BTK-mediated disease or condition is a B-cell cancer. In some embodiments, the diagnostic methods are employed for the screening of subjects having a B-cell cancer that is resistant to therapy with a covalent and/or irreversible BTK inhibitor, identifying subjects for the treatment with a covalent and/or irreversible BTK inhibitor, identifying subjects as likely or unlikely to respond to treatment with a covalent and/or irreversible BTK inhibitor, predicting whether a subject is likely to develop resistance to treatment with a covalent and/or irreversible BTK inhibitor, monitoring the therapy of subjects receiving therapy with a covalent and/or irreversible BTK inhibitor, optimizing the therapy of subjects receiving a covalent and/or irreversible BTK inhibitor therapy, and any combinations thereof. In some embodiments, the diagnostic methods involve the detection of a mutant PLCγ2 polypeptide. In some embodiments, the methods comprise selecting a subject for therapy with an inhibitor of PLCγ2. In some embodiments, the methods further comprise administering to the subject an inhibitor of PLCγ2 that inhibits the mutant PLCγ2. In some embodiments, the PLCγ2 modification confers resistance of a cancer cell to treatment with a covalent and/or irreversible BTK inhibitor. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, provided is a method of assessing whether a subject is less responsive or likely to become less responsive to therapy with a BTK inhibitor, comprising: (a) testing a sample containing a nucleic acid molecule encoding a PLCγ2 polypeptide from the subject; (b) determining whether the encoded PLCγ2 polypeptide is modified at an amino acid position corresponding to amino acid position 742, 845, or 1140 of the amino acid sequence set forth in SEQ ID NO: 2; and (c) characterizing the subject as resistant or likely to become resistant to therapy with a BTK inhibitor if the subject has the modification at amino acid position 742, 845, or 1140. In some embodiments, the modification is R742P. In some embodiments, the modification is L845F. In some embodiments, the modification is D1140G. In some embodiments, the subject has been administered a covalent and/or irreversible BTK inhibitor for the treatment of a cancer. In some embodiments, the method further comprises determining whether the encoded PLCγ2 polypeptide is modified at one or more additional amino acid positions. In some embodiments, the method further comprises testing a sample and determining the presence of mutations in PLCγ2 and an additional polypeptide. In some embodiments, the additional polypeptide is a polypeptide that encoded by a gene associated in the BCR pathway. In some embodiments, the method further comprises discontinuing treatment with the BTK inhibitor if the subject has a modification at amino acid position 742, 845, or 1140 in the PLCγ2 polypeptide. In some embodiments, the method further comprises discontinuing treatment with the BTK inhibitor if the subject has one or more modifications with at least one modification at amino acid position 742, 845, or 1140 in the PLCγ2 polypeptide. In some embodiments, the method further comprises discontinuing treatment with the BTK inhibitor if the subject has one or more modifications with at least one modification at amino acid positions 742, 845, or 1140 in the PLCγ2 polypeptide and modifications in an additional polypeptide. In some embodiments, the method further comprises discontinuing treatment with the BTK inhibitor if the subject has no modification at amino acid position 742, 845, or 1140 in the PLCγ2 polypeptide but has additional modifications in the PLCγ2 polypeptide and/or has modifications in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in PLCγ2 polypeptide. In some embodiments, the method further comprises continuing treatment with the covalent and/or irreversible BTK inhibitor if the subject does not have modifications in the PLCγ2 polypeptide. In some embodiments, the method further comprises continuing treatment with the covalent and/or irreversible BTK inhibitor if the subject does not have modifications in the PLCγ2 polypeptide but has modifications in an additional polypeptide. In some embodiments, the method further comprises continuing treatment with the covalent and/or irreversible BTK inhibitor if the subject does not have modifications in the PLCγ2 and an additional polypeptide. In some embodiments, the additional polypeptide is a BTK polypeptide. In some embodiments, the subject possesses high-risk cytogenetic features. In some embodiments, the high-risk cytogenetic features comprise del(11q22.3), del(17p13.1) or complex karyotype. In some embodiments, the subject has a hematologic cancer or a B-cell malignancy. In some embodiments, the cancer is selected from among a leukemia, a lymphoma or a myeloma. In some embodiments, the B-cell malignancy is CLL. In some embodiments, the subject has lymphocytosis. In some embodiments, the subject has prolonged lymphocytosis. In some embodiments, the subject with prolonged lymphocytosis does not have the 742, 845, or 1140 mutation in the PLCγ2 polypeptide. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, provided is a method of monitoring whether a subject receiving a BTK inhibitor for treatment of a cancer has developed or is likely to develop resistance to the therapy, comprising: (a) testing a sample containing a nucleic acid molecule encoding a PLCγ2 polypeptide from the subject; (b) determining whether the encoded PLCγ2 polypeptide is modified at an amino acid position corresponding to amino acid position 742, 845, or 1140 of the amino acid sequence set forth in SEQ ID NO: 2; and (c) characterizing the subject as resistant or is likely to become resistant to therapy with a BTK inhibitor if the subject has the modification at amino acid position 742, 845, or 1140. In some embodiments, the modification is R742P. In some embodiments, the modification is L845F. In some embodiments, the modification is D1140G. In some embodiments, the method further comprises determining whether the encoded PLCγ2 polypeptide is modified at one or more additional amino acid positions. In some embodiments, the method further comprises testing a sample and determining the presence of mutations in PLCγ2 and an additional polypeptide. In some embodiments, the additional polypeptide is a polypeptide that encoded by a gene associated in the BCR pathway. In some embodiments, the method further comprises discontinuing treatment with the BTK inhibitor if the subject has a modification at amino acid position 742, 845, or 1140 in the PLCγ2 polypeptide. In some embodiments, the method further comprises discontinuing treatment with the BTK inhibitor if the subject has one or more modifications at amino acid positions with at least one modification at amino acid position 742, 845, or 1140 in the PLCγ2 polypeptide. In some embodiments, the method further comprises discontinuing treatment with the BTK inhibitor if the subject has one or more modifications at amino acid positions in the PLCγ2 polypeptide with at least one modification at amino acid position 742, 845, or 1140 and modifications in an additional polypeptide. In some embodiments, the method further comprises discontinuing treatment with the BTK inhibitor if the subject has no modifications at amino acid position 742, 845, or 1140 in the PLCγ2 polypeptide but has additional modifications in the PLCγ2 polypeptide and/or has modifications in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in the PLCγ2 polypeptide. In some embodiments, the method further comprises continuing treatment with the covalent and/or irreversible BTK inhibitor if the subject does not have modifications in the PLCγ2 polypeptide. In some embodiments, the method further comprises continuing treatment with the covalent and/or irreversible BTK inhibitor if the subject does not have modifications in the PLCγ2 polypeptide but has modifications in an additional polypeptide. In some embodiments, the method further comprises continuing treatment with the covalent and/or irreversible BTK inhibitor if the subject does not have modifications in the PLCγ2 and an additional polypeptide. In some embodiments, the additional polypeptide is a BTK polypeptide. In some embodiments, the subject possesses high-risk cytogenetic features. In some embodiments, the high-risk cytogenetic features comprise del(11q22.3), del(17p13.1) or complex karyotype. In some embodiments, the subject has a hematologic cancer or a B-cell malignancy. In some embodiments, the cancer is selected from among a leukemia, a lymphoma or a myeloma. In some embodiments, the B-cell malignancy is CLL. In some embodiments, the subject has lymphocytosis. In some embodiments, the subject has prolonged lymphocytosis. In some embodiments, the subject with prolonged lymphocytosis does not have mutations in the PLCγ2 polypeptide. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, provided herein is a method of optimizing the therapy of a subject receiving a BTK inhibitor for treatment of a cancer, comprising: (a) testing a sample containing a nucleic acid molecule encoding a PLCγ2 polypeptide from the subject; and (b) determining whether the encoded PLCγ2 polypeptide is modified at an amino acid position corresponding to amino acid position 742, 845, or 1140 of the amino acid sequence set forth in SEQ ID NO: 2. In some embodiments, the modification is R742P. In some embodiments, the modification is L845F. In some embodiments, the modification is D1140G. In some embodiments, the method further comprises determining whether the encoded PLCγ2 polypeptide is modified at additional amino acid positions. In some embodiments, the method further comprises testing a sample and determining the presence of mutations in PLCγ2 and an additional polypeptide. In some embodiments, the additional polypeptide is a polypeptide that encoded by a gene associated in the BCR pathway. In some embodiments, the method further comprises discontinuing treatment with the BTK inhibitor if the subject has a modification at amino acid position 742, 845, or 1140 in the PLCγ2 polypeptide. In some embodiments, the method further comprises discontinuing treatment with the BTK inhibitor if the subject has one or more modifications with at least one modification at amino acid position 742, 845, or 1140 in the PLCγ2 polypeptide and modifications in an additional polypeptide. In some embodiments, the method further comprises discontinuing treatment with the BTK inhibitor if the subject has no modification at amino acid position 742, 845, or 1140 in the PLCγ2 polypeptide but has additional modifications in the PLCγ2 polypeptide and/or has modifications in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in the PLCγ2 polypeptide. In some embodiments, the method further comprises continuing treatment with the covalent and/or irreversible BTK inhibitor if the subject does not have modifications in the PLCγ2 polypeptide. In some embodiments, the method further comprises continuing treatment with the covalent and/or irreversible BTK inhibitor if the subject does not have modifications in the PLCγ2 polypeptide but has modifications in an additional polypeptide. In some embodiments, the method further comprises continuing treatment with the covalent and/or irreversible BTK inhibitor if the subject does not have modifications in the PLCγ2 and an additional polypeptide. In some embodiments, the additional polypeptide is a BTK polypeptide. In some embodiments, the subject possesses high-risk cytogenetic features. In some embodiments, the high-risk cytogenetic features comprise del(11q22.3), del (17p13.1) or complex karyotype. In some embodiments, the subject has a hematologic cancer or a B-cell malignancy. In some embodiments, the cancer is selected from among a leukemia, a lymphoma or a myeloma. In some embodiments, the B-cell malignancy is CLL. In some embodiments, the subject has lymphocytosis. In some embodiments, the subject has prolonged lymphocytosis. In some embodiments, the subject with prolonged lymphocytosis does not have mutations in the PLCγ2 polypeptide. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, provided is a method of assessing whether a subject who possess high-risk cytogenetic features is less responsive or likely to become less responsive to therapy with a BTK inhibitor, comprising: (a) testing a sample containing a nucleic acid molecule encoding a PLCγ2 polypeptide from the subject; (b) determining whether the encoded PLCγ2 polypeptide is modified at amino acid position corresponding to amino acid position 742, 845, or 1140 of the amino acid sequence set forth in SEQ ID NO: 2; and (c) characterizing the subject as resistant or likely to become resistant to therapy with a BTK inhibitor if the subject has the modification. In some embodiments, the method further comprises testing a sample and determining the presence of additional mutations in the PLCγ2 polypeptide. In some embodiments, the method further comprises testing a sample and determining the presence of mutations in PLCγ2 and an additional polypeptide. In some embodiments, the additional polypeptide is a polypeptide that encoded by a gene associated in the BCR pathway. In some embodiments, the method further comprises discontinuing treatment with the BTK inhibitor if the subject has a modification at amino acid position 742, 845, or 1140 in the PLCγ2 polypeptide. In some embodiments, the method further comprises discontinuing treatment with the BTK inhibitor if the subject has one or more modifications with at least one modification at amino acid position 742, 845, or 1140 in the PLCγ2 polypeptide. In some embodiments, the method further comprises discontinuing treatment with the BTK inhibitor if the subject has one or more modifications in the PLCγ2 polypeptide and modifications in an additional polypeptide. In some embodiments, the method further comprises discontinuing treatment with the BTK inhibitor if the subject has no modification at amino acid position 742, 845, or 1140 in the PLCγ2 polypeptide but has additional modifications in the PLCγ2 polypeptide and/or has modifications in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in PLCγ2 and/or BTK polypeptide. In some embodiments, the method further comprises continuing treatment with the covalent and/or irreversible BTK inhibitor if the subject does not have modifications in the PLCγ2 polypeptide. In some embodiments, the method further comprises continuing treatment with the covalent and/or irreversible BTK inhibitor if the subject does not have modifications in the PLCγ2 but has modifications in an additional polypeptide. In some embodiments, the method further comprises continuing treatment with the covalent and/or irreversible BTK inhibitor if the subject does not have modifications in the PLCγ2 and an additional polypeptide. In some embodiments, the additional polypeptide is a BTK polypeptide. In some embodiments, the subject has a hematologic cancer or a B-cell malignancy. In some embodiments, the cancer is selected from among a leukemia, a lymphoma or a myeloma. In some embodiments, the B-cell malignancy is CLL. In some embodiments, the subject has lymphocytosis. In some embodiments, the subject has prolonged lymphocytosis. In some embodiments, the subject with prolonged lymphocytosis does not have mutations in the PLCγ2 polypeptide. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, provided is a method of monitoring whether a subject who possess high-risk cytogenetic features during the course of a therapy with a BTK inhibitor has developed or is likely to develop resistance to the therapy, comprising: (a) testing a sample containing a nucleic acid molecule encoding a BTK polypeptide and a nucleic acid molecule encoding a PLCγ2 polypeptide from the subject; (b) determining whether the encoded PLCγ2 polypeptide is modified at the amino acid position corresponding to amino acid position 742, 845, or 1140 of the amino acid sequence set forth in SEQ ID NO: 2; and (c) characterizing the subject as resistant or likely to become resistant to therapy with a BTK inhibitor if the subject has the modification. In some embodiments, the method further comprises testing a sample and determining the presence of additional mutations in the PLCγ2 polypeptide. In some embodiments, the method further comprises testing a sample and determining the presence of mutations in PLCγ2 and an additional polypeptide. In some embodiments, the additional polypeptide is a polypeptide that encoded by a gene associated in the BCR pathway. In some embodiments, the method further comprises discontinuing treatment with the BTK inhibitor if the subject has the modification at amino acid position 742, 845, or 1140 in the PLCγ2 polypeptide. In some embodiments, the method further comprises discontinuing treatment with the BTK inhibitor if the subject has one or more modifications with at least one modification at amino acid position 742, 845, or 1140 in the PLCγ2 polypeptide and modifications in an additional polypeptide. In some embodiments, the method further comprises discontinuing treatment with the BTK inhibitor if the subject has no modification at amino acid position 742, 845, or 1140 in the PLCγ2 polypeptide but has additional modifications in the PLCγ2 polypeptide and/or has modifications in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in PLCγ2 and/or BTK polypeptide. In some embodiments, the method further comprises continuing treatment with the covalent and/or irreversible BTK inhibitor if the subject does not have modifications in the PLCγ2 polypeptide. In some embodiments, the method further comprises continuing treatment with the covalent and/or irreversible BTK inhibitor if the subject does not have modifications in the PLCγ2 polypeptide but has modifications in an additional polypeptide. In some embodiments, the method further comprises continuing treatment with the covalent and/or irreversible BTK inhibitor if the subject does not have modifications in the PLCγ2 polypeptide and an additional polypeptide. In some embodiments, the additional polypeptide is a BTK polypeptide. In some embodiments, the subject has a hematologic cancer or a B-cell malignancy. In some embodiments, the cancer is selected from among a leukemia, a lymphoma or a myeloma. In some embodiments, the B-cell malignancy is CLL. In some embodiments, the subject has lymphocytosis. In some embodiments, the subject has prolonged lymphocytosis. In some embodiments, the subject with prolonged lymphocytosis does not have mutations in the PLCγ2 polypeptide. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, provided is a method of optimizing the therapy with a BTK inhibitor of a subject who possess high-risk cytogenetic features, comprising: (a) testing a sample containing a nucleic acid molecule encoding a PLCγ2 polypeptide from the subject; (b) determining whether the encoded PLCγ2 polypeptide is modified at amino acid position corresponding to amino acid position 742, 845, or 1140 of the amino acid sequence set forth in SEQ ID NO: 2; and (c) discontinuing treatment with the BTK inhibitor if the subject has the modification or continuing treatment with the BTK inhibitor if the subject does not have the modification in the PLCγ2 polypeptide. In some embodiments, the method further comprises testing a sample and determining the presence of additional mutations in the PLCγ2 polypeptide. In some embodiments, the method further comprises testing a sample and determining the presence of mutations in the PLCγ2 polypeptide and an additional polypeptide. In some embodiments, the additional polypeptide is a polypeptide that encoded by a gene associated in the BCR pathway. In some embodiments, the method further comprises discontinuing treatment with the BTK inhibitor if the subject has the modification at amino acid position 742, 845, or 1140 in the PLCγ2 polypeptide. In some embodiments, the method further comprises discontinuing treatment with the BTK inhibitor if the subject has one or more modifications with at least one modification at amino acid position 742, 845, or 1140 in the PLCγ2 polypeptide and modifications in an additional polypeptide. In some embodiments, the method further comprises discontinuing treatment with the BTK inhibitor if the subject has no modifications at amino acid position 742, 845, or 1140 in the PLCγ2 polypeptide but has additional modifications in the PLCγ2 polypeptide and/or has modifications in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in PLCγ2 and/or BTK polypeptide. In some embodiments, the method further comprises continuing treatment with the covalent and/or irreversible BTK inhibitor if the subject does not have modifications in the PLCγ2 polypeptide. In some embodiments, the method further comprises continuing treatment with the covalent and/or irreversible BTK inhibitor if the subject does not have modifications in the PLCγ2 polypeptide but has modifications in an additional polypeptide. In some embodiments, the method further comprises continuing treatment with the covalent and/or irreversible BTK inhibitor if the subject does not have modifications in the PLCγ2 polypeptide and an additional polypeptide. In some embodiments, the additional polypeptide is a BTK polypeptide. In some embodiments, the subject has a hematologic cancer or a B-cell malignancy. In some embodiments, the cancer is selected from among a leukemia, a lymphoma or a myeloma. In some embodiments, the B-cell malignancy is CLL. In some embodiments, the subject has lymphocytosis. In some embodiments, the subject has prolonged lymphocytosis. In some embodiments, the subject with prolonged lymphocytosis does not have mutations in the PLCγ2 polypeptide. In some embodiments, the patient exhibits one or more symptoms of a relapsed or refractory cancer. In some embodiments, the relapsed or refractory cancer is a relapsed or refractory non-Hodgkin's lymphoma. In some embodiments, the relapsed or refractory cancer is a relapsed or refractory chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient exhibits one or more symptoms of Richter's transformation.

In some embodiments, the subject possesses cytogenetic features. In some embodiments, the cytogenetic features is further categorized as low-risk or favorable, intermediate or high-risk or unfavorable cytogenetic features. In some embodiments, the subject possesses high-risk cytogenetic features. In some embodiments, cytogenetic features are associated with cytogenetic abnormalities. In some embodiments, high-risk cytogenetic features are associated with cytogenetic abnormalities. In some embodiments, the subject possessing high-risk cytogenetic features have cytogenetic abnormalities.

In some embodiments, cytogenetic abnormalities are associated with aberrant chromosomes or aberrant chromosome number. In some embodiments, aberrant chromosomes refer to chromosomes comprising deletion, duplication, inversion, insertion, translocation or any combinations thereof. In some embodiments, aberrant chromosome number refers to addition or deletion of a chromosome. In some embodiments, multiple cytogenetic abnormalities are associated with aberrant chromosomes or chromosome numbers. In some embodiments, the multiple cytogenetic abnormalities are referred to as a complex karyotype. In some embodiments, the complex karyotype comprises about 2, 3, 4, 5, 6, 7, 8, 9 10 or more cytogenetic abnormalities. In some embodiments, the cytogenetic abnormalities occurs on chromosome 1, 2, 3, 4, 5, 6, 7, 8, 9, 10, 11, 12, 13, 14, 15, 16, 17, 18, 19, 20, 21, 22, X, Y or any combinations thereof.

In some embodiments, cytogenetic abnormalities result in gene alterations. In some embodiments, gene alterations comprise insertion, deletion or substitution of one or more amino acids. In some embodiments, gene alterations results in mutations. In some embodiments, mutations comprise nonsense mutation, missense mutation, silent mutation, frameshift mutation, dynamic mutation or any combinations thereof. In some embodiments, the mutations occur on chromosome 1, 2, 3, 4, 5, 6, 7, 8, 9, 10, 11, 12, 13, 14, 15, 16, 17, 18, 19, 20, 21, 22, X, Y or any combinations thereof.

In some embodiments, different cancers are associated with different cytogenetic abnormalities. In some embodiments, a subject who has a particular cancer is associated with a particular set of cytogenetic abnormalities. In some embodiments, a subject who has high-risk cytogenetic features has a particular set of cytogenetic abnormalities. In some embodiments, the cancer is a hematologic cancer or a B-cell malignancy. In some embodiments, the cancer is selected from among a leukemia, a lymphoma or a myeloma. In some embodiments, the B-cell malignancy is CLL. In some embodiments, cytogenetic abnormalities associated with CLL comprise trisomy 12, del(11q22.3), del(13q14.3), del(17p13.1), t(11;14)(q13;q32), t(14;19)(q32;q13) or t(2;14)(p13;q32). In some embodiments, the complex karyotype comprises about two or more cytogenetic abnormalities selected from trisomy 12, del(11q22.3), del(13q14.3), del(17p13.1), t(11;14)(q13;q32), t(14;19)(q32;q13) or t(2;14)(p13;q32). In some embodiments, high-risk cytogenetic features comprise of cytogenetic abnormalities selected from trisomy 12, del(11q22.3), del(13q14.3), del(17p13.1), t(11;14)(q13;q32), t(14;19)(q32;q13) or t(2;14)(p13;q32). In some embodiments, the subject has CLL. In some embodiments, the subject having CLL possesses high-risk cytogenetic features. In some embodiments, the subject possessing high-risk cytogenetic features has cytogenetic abnormalities selected from trisomy 12, del(11q22.3), del(13q14.3), del(17p13.1), t(11;14)(q13;q32), t(14;19)(q32;q13) or t(2;14)(p13;q32). In some embodiments, the subject possessing high-risk cytogenetic features has del(11q22.3), del(17p13.1) or a complex karyotype. In some embodiments, the subject possessing high-risk cytogenetic features has del(11q22.3). In some embodiments, the subject possessing high-risk cytogenetic features has del(17p13.1). In some embodiments, the subject possessing high-risk cytogenetic features has a complex karyotype.

In some embodiments, a subject possessing high-risk cytogenetic features is associated with CLL relapse. In some embodiments, CLL relapse is associated with ibrutinib resistance. In some embodiments, the subject possessing high-risk cytogenetic features is associated with ibrutinib resistance. In some embodiments, ibrutinib resistance is associated with mutations in the PLCγ2 gene. In some embodiments, ibrutinib resistance is associated with mutations in only PLCγ2. The PLCγ2 gene is located on chromosome 16. In some embodiments, ibrutinib resistance is associated with mutations in PLCγ2 and an additional gene. In some embodiments, ibrutinib resistance is not associated with mutations in PLCγ2. In some embodiments, ibrutinib resistance is associated with mutation at amino acid position 742, 845, or 1140 in the PLCγ2 gene (those amino acid sequence is set forth in SEQ ID NO: 2).

In some embodiments, the subject possessing high-risk cytogenetic features having ibrutinib resistance has mutations in the PLCγ2. In some embodiments, the subject possessing high-risk cytogenetic features having ibrutinib resistance has mutations in only PLCγ2. In some embodiments, the subject possessing high-risk cytogenetic features having ibrutinib resistance has mutations in PLCγ2 and an additional gene. In some embodiments, the subject possessing high-risk cytogenetic features having ibrutinib resistance has mutation at amino acid position 742, 845, or 1140 in the PLCγ2 gene. In some embodiments, the subject possessing high-risk cytogenetic features having ibrutinib resistance does not have mutations in PLCγ2. In some embodiments, the subject possessing high-risk cytogenetic features having ibrutinib resistance does not have mutation at amino acid position 742, 845, or 1140 in PLCγ2.

In some embodiments, ibrutinib resistance is associated with mutations in PLCγ2 and an additional gene. In some embodiments, the additional gene is selected from CSF1, DAB1, ARTN, COL8A2 or LDLRAP1 located on chromosome 1; PRR21, NDUFA10, ASIC4, POTEE or XPO1 located on chromosome 2; RAB6B, TMPRSS7 or CACNA1D located on chromosome 3; GUCY1B3, MAML3, FRAS1 or EVC2 located on chromosome 4; NPM1, G3BP1, H2AFY, HEATR7B2 or ADAMTS12 located on chromosome 5; KIAA1244, ENPP1, NKAIN2, REV3L, COL12A1 or IRF4 located on chromosome 6; ZNF775, SSPO, ZNF777 or ABCA13 located on chromosome 7; TRPS1 located on chromosome 8; UAP1L1, AGPAT2, SNAPC4, RALGPS1 or GNAQ located on chromosome 9; PIK3AP1, EGR2 or NRP1 located on chromosome 10; KRTAP5-9, CAPN1 or MUC2 located on chromosome 11; DPY19L2, KRT73, SLC11A2, MLL2, SYT10 or OVOS2 located on chromosome 12; TRPC4 located on chromosome 13; SLC8A3 located on chromosome 14; BLM, DISP2 or C15orf55 located on chromosome 15; MMP25 or MAPK8IP3 located on chromosome 16; LLGL2, KRTAP9-3, TRAF4, CENPV or TP53 located on chromosome 17; CEACAM18, SPIB, TPRX1, DMKN, LSM4, CACNA1A, CCDC151, LONP1 or STAP2 located on chromosome 19; TSPEAR, KCNJ15, DYRK1A or IFNAR1 located on chromosome 21; SLC5A4 or HIRA located on chromosome 22; or BTK, IL13RA2, MAGEE1, SHROOM4 or NYX located on chromosome X. In some embodiments, the subject possessing high-risk cytogenetic features has mutations in PLCγ2 and BTK. In some embodiments, the subject possessing high-risk cytogenetic features has mutations in PLCγ2, BTK and an additional gene.

In some embodiments of the methods, the nucleic acid molecule for use in the assay is RNA or DNA. In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample. In some embodiments of the methods, the nucleic acid molecule for use in the assay is cDNA. In some embodiments of the methods, the method further comprises reverse transcribing an RNA sample into cDNA. In some embodiments of the methods, the method comprises analyzing the cDNA. In some embodiments, the sample is a plasma or serum sample containing circulating tumor DNA (ctDNA), RNA (ctRNA) or microRNA (see e.g., Chan et al. (2007) Br J Cancer. 96(5):681-5).

In some embodiments, the genomic nucleic acid sample is amplified by a nucleic acid amplification method. In some embodiments, the nucleic acid amplification method is polymerase chain reaction (PCR). In some embodiments, the genomic nucleic acid sample is amplified using a set of nucleotide primers specific for the PLCγ2 gene. In some embodiments, the set of nucleotide primers flank the nucleic acid sequence encoding amino acid position 742, 845, or 1140 of the PLCγ2 polypeptide. In some embodiments, the amplification product is a nucleic acid encoding amino acid position 742, 845, or 1140 of the PLCγ2 polypeptide. In some embodiments, a sequence specific primer is conjugated to a detectable molecule, such as a fluorescent label, a bioluminescent label, a chemiluminescent label, a radiolabel, an enzyme label, a detectable substrate, or a peptide or molecule that binds to a second detectable molecule.

A variety of methods are available in the art for the detection of single point mutations in nucleic acids encoding mutant PLCγ2 polypeptides and amino acid changes in the PLCγ2 polypeptide in a sample. The following methods for detection of mutations in nucleic acids and mutant polypeptides are meant to be exemplary and are not exclusive.

In some embodiments of the methods, testing comprises performing polymerase chain reaction (PCR) amplification of nucleic acid encoding amino acid position 742, 845, or 1140 of the PLCγ2 polypeptide. In some embodiments, PCR amplification comprises using a pair of oligonucleotide primers that flank the region encoding amino acid position 742, 845, or 1140 of the PLCγ2 polypeptide. In some embodiments, the method comprises sequencing the amplified nucleic acid using a sequence specific primer. In some embodiments, the method comprises ligating the amplified PCR fragment into a vector and then sequencing the nucleic acid encoding the PLCγ2 polypeptide or portion thereof containing amino acid position 742, 845, or 1140. In some embodiments, the method comprises sequencing the amplified nucleic acid in a vector using a vector sequence specific primer. In some embodiments, the sequencing method is a high-throughput method. In some embodiments, the sequencing method is a next-generation sequencing method.

As described elsewhere herein, exemplary sequencing methods for use in the methods provide herein include, but are not limited to, dideoxy or chain termination methods, Maxam-Gilbert sequencing, massively parallel signature sequencing (or MPSS), polony sequencing, pyrosequencing, Illumina dye sequencing, SOLiD (or sequencing by ligation) sequencing, ion semiconductor sequencing, DNA nanoball sequencing, heliscope sequencing, single molecule real time (SMRT) sequencing, whole-exome sequencing, Ion Torrent sequencing, Helicos True Single Molecule Sequencing (tSMS) (Harris T. D. et al. (2008) Science 320:106-109); 454 sequencing (Roche) (Margulies, M. et al. 2005, Nature, 437, 376-380); SOLiD technology (Applied Biosystems); SOLEXA sequencing (Illumina); single molecule, real-time (SMRT™) technology of Pacific Biosciences; nanopore sequencing (Soni G V and Meller A. (2007) Clin Chem 53: 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g. Oxford Nanopore, Genia Technologies, and Nabsys).

In some embodiments of the methods, testing comprises contacting the nucleic acid molecule encoding a PLCγ2 polypeptide with a sequence specific nucleic acid probe, wherein the sequence specific nucleic acid probe: (a) binds to nucleic acid encoding a modified PLCγ2 that is modified at amino acid position 742, 845, or 1140; and (b) does not bind to nucleic acid encoding the wild-type PLCγ2 having leucine at amino acid position 742, 845, or 1140. In some embodiments of the methods, testing comprises PCR amplification using the sequence specific nucleic acid probe. In some embodiments, testing further comprises additional sequence specific nucleic acid probes. In some embodiments, the sequence specific probe is conjugated to a detectable molecule, such as a fluorescent label, a bioluminescent label, a chemiluminescent label, a radiolabel, an enzyme label, a detectable substrate, or a peptide or molecule that binds to a second detectable molecule.

In some embodiments of the methods, testing the sample comprises contacting the nucleic acid with a pair of oligonucleotide primers that flank the nucleic acid region encoding amino acid 742, 845, or 1140 of a PLCγ2 polypeptide. In some embodiments, testing the sample further comprises oligonucleotide primers that flank the nucleic acid regions encoding additional amino acid positions of the PLCγ2 polypeptide. In some embodiments, testing the sample further comprises oligonucleotide primers that flank the nucleic acid regions encoding additional polypeptides.

In some embodiments of the methods, testing comprises using allele specific PCR. In some embodiments, single nucleotide changes are detectable PCR using PCR-based cleaved amplified polymorphic sequences (CAPS) markers which create restriction sites in the mutant sequences (Michaels et al (1998) *Plant J.* 14(3):381-5) or sequence specific hairpin probes attached to detectable moieties, such as, but not limited to, a fluorophore (Mhlanga and Malmberg (2001) *Methods* 25:463-471). In some embodiments, the sequence specific probe is conjugated to a detectable molecule, such as a fluorescent label, a bioluminescent label, a chemiluminescent label, a radiolabel, an enzyme label, a detectable substrate, or a peptide or molecule that binds to a second detectable molecule. In some embodiments, the oligonucleotide probe is specific for nucleic acid encoding serine at a position corresponding to amino acid 742, 845, or 1140 of a PLCγ2 polypeptide.

In some embodiments, the DNA encoding the mutant PLCγ2 is assessed by BEAMing (beads, amplification, emulsion, magnetic) PCR sequencing method (see, e.g., Li et al. (2006) *Nat Methods.* 3(2):95-7; Li et al. (2006) *Nat Methods.* 3(7):551-9; and Diehl et al. (2008) *Nat Med.* 14(9): 985-990). BEAMing is a technique in which individual DNA molecules are attached to magnetic beads in water-in-oil emulsions and then subjected to compartmentalized PCR amplification. The mutational status of DNA bound to beads is then determined by hybridization to fluorescent allele-specific probes for, for example, mutant or wild-type PLCγ2. Flow cytometry is then used to quantify the level of mutant DNA present in the plasma or serum (see e.g., Higgins et al. (2012) *Clin Cancer Res* 18: 3462-3469).

In some embodiments, testing the sample comprises denaturing high performance liquid chromatography (D-HPLC). D-HPLC relies upon the differential retention kinetics of heteroduplex/homoduplex DNA species within a cartridge matrix designed to separate DNA fragments according to charge density against an electrolyte gradient. (see e.g., Frueh et al (2003) *Clin Chem Lab Med.* 41(4):452-61).

In some embodiments, testing the sample comprises nanofluidics, including using NanoPro to determine the pI differences in a wild-type or mutant polypeptide bound to an inhibitor. For example, NanoPro can be used to determine the pI differences in a wild-type PLCγ2 polypeptide covalently bound to a PLCγ2 inhibitor at amino acid position 742, 845, or 1140 and mutant PLCγ2 polypeptide (e.g., having a modification that is R742P, L845F, D1140G) that does not covalently bind to the PLCγ2 inhibitor. NanoPro is an instrument that can separate proteins based on small differences in isoelectric points. The covalent modification of amino acid position 742, 845, or 1140 with the PLCγ2 inhibitor compared to the unconjugated mutant PLCγ2 will change its isoelectric point, which is used to detect drug binding to PLCγ2.

In some embodiments, testing the sample comprises using a microarray. In some embodiments, the presence of DNA encoding the mutant PLCγ2 is assessed using an oligonucleotide array (see e.g., Hastia et al. (1999) *J Med Genet.* 36(10):730-6). In some embodiments, the microarray comprising nucleic acid encoding a modified PLCγ2 polypeptide or a portion thereof that is modified at an amino acid position corresponding to amino acid position 742, 845, or 1140 of the amino acid sequence set forth in SEQ ID NO: 2. In some embodiments, the microarray further comprises comprising nucleic acid encoding a modified PLCγ2 polypeptide or a portion thereof that is modified at additional amino acid positions. In some embodiments, the oligonucleotide array is contained on a microchip. In some embodiments, single nucleotide changes are detectable using microchips.

In some embodiments of the method, the sample for detection of a mutant PLCγ2 is a protein sample that contains a PLCγ2 polypeptide. In such examples, testing comprises detection of the mutation with an antibody specific for the mutant polypeptides. In some embodiments, the method of detecting a mutant PLCγ2 polypeptide comprises providing a sample from a subject, wherein the sample comprises a PLCγ2 polypeptide and testing the sample for the presence of a mutant PLCγ2 polypeptide by contacting the sample with an antibody that is specific for binding to the mutant PLCγ2 polypeptide, and does not bind or binds with decreased affinity for the wild-type PLCγ2 polypeptide, wherein the presence of the mutant PLCγ2 polypeptide creates an antibody-mutant PLCγ2 polypeptide complex. In some embodiments, the method further comprises detecting the antibody-mutant PLCγ2 polypeptide complex. In some embodiments, the method further comprises detecting the antibody-mutant PLCγ2 polypeptide complex with a detection reagent. In some embodiments, the mutant PLCγ2 specific antibody is conjugated to a detectable molecule, such as a fluorescent label, a bioluminescent label, a chemiluminescent label, a radiolabel, an enzyme label, a detectable substrate, or a peptide or molecule that binds to a second detectable protein (e.g., a secondary antibody). In some embodiments, binding of the mutant PLCγ2 specific antibody is detected by assaying for the detectable molecule. In some embodiments, binding of the mutant PLCγ2 specific antibody is detected by using a secondary (e.g., anti-IgG) antibody.

In some embodiments of the methods, the subject has a BTK-mediated disease or disorder. In some embodiments of the methods, the subject has a B-cell proliferative disorder. In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments, the subject has a solid tumor. In some embodiments, the subject has a sarcoma, carcinoma, a neurofibromatoma or a lymphoma.

In some embodiments, the subject has a cancer of the lung, breast, colon, brain, prostate, liver, pancreas, esophagus, kidney, stomach, thyroid, bladder, uterus, cervix or ovary. In some embodiments, the subject has a metastatic cancer. In some embodiments, the subject has a cancer that is acute lymphoblastic leukemia, acute lymphoblastic leukemia, acute myeloid leukemia, acute promyelocytic leukemia, adenocarcinoma, adenoma, adrenal cancer, adrenocortical carcinoma, AIDS-related cancer, AIDS-related lymphoma, anal cancer, appendix cancer, astrocytoma, basal cell carcinoma, bile duct cancer, bladder cancer, bone cancer, osteosarcoma/malignant fibrous histiocytoma, brainstem glioma, brain cancer, carcinoma, cerebellar astrocytoma, cerebral astrocytoma/malignant glioma, ependymoma, medulloblastoma, supratentorial primitive neuroectodermal tumor, visual pathway or hypothalamic glioma, breast cancer, bronchial adenoma/carcinoid, Burkitt lymphoma, carcinoid tumor, carcinoma, central nervous system lymphoma, cervical cancer, chronic lymphocytic leukemia, chronic myelogenous leukemia, chronic myeloproliferative disorder, colon cancer, cutaneous T-cell lymphoma, desmoplastic small round cell tumor, endometrial cancer, ependymoma epidermoid carcinoma, esophageal cancer, Ewing's sarcoma, extracranial germ cell tumor, extragonadal germ cell tumor, extrahepatic bile duct cancer, eye cancer/intraocular melanoma, eye cancer/retinoblastoma, gallbladder cancer, gallstone tumor, gastric/stomach cancer, gastrointestinal carcinoid tumor, gastrointestinal stromal tumor, giant cell tumor, glioblastoma multiforme, glioma, hairy-cell tumor, head and neck cancer, heart cancer, hepatocellular/liver cancer, Hodgkin lymphoma, hyperplasia, hyperplastic corneal nerve tumor, in situ carcinoma, hypopharyngeal cancer, intestinal ganglioneuroma, islet cell tumor, Kaposi's sarcoma, kidney/renal cell cancer, laryngeal cancer, leiomyoma tumor, lip and oral cavity cancer, liposarcoma, liver cancer, non-small cell lung cancer, small cell lung cancer, lymphomas, macroglobulinemia, malignant carcinoid, malignant fibrous histiocytoma of bone, malignant hypercalcemia, malignant melanomas, marfanoid habitus tumor, medullary carcinoma, melanoma, merkel cell carcinoma, mesothelioma, metastatic skin carcinoma, metastatic squamous neck cancer, mouth cancer, mucosal neuromas, multiple myeloma, mycosis fungoides, myelodysplastic syndrome, myeloma, myeloproliferative disorder, nasal cavity and paranasal sinus cancer, nasopharyngeal carcinoma, neck cancer, neural tissue cancer, neuroblastoma, oral cancer, oropharyngeal cancer, osteosarcoma, ovarian cancer, ovarian epithelial tumor, ovarian germ cell tumor, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, polycythemia vera, primary brain tumor, prostate cancer, rectal cancer, renal cell tumor, reticulum cell sarcoma, retinoblastoma, rhabdomyosarcoma, salivary gland cancer, seminoma, Sezary syndrome, skin cancer, small intestine cancer, soft tissue sarcoma, squamous cell carcinoma, squamous neck carcinoma, stomach cancer, supratentorial primitive neuroectodermal tumor, testicular cancer, throat cancer, thymoma, thyroid cancer, topical skin lesion, trophoblastic tumor, urethral cancer, uterine/endometrial cancer, uterine sarcoma, vaginal cancer, vulvar cancer, Waldenström's macroglobulinemia or Wilm's tumor.

In some embodiments, the subject has a relapsed cancer. In some embodiments, the subject has a refractory cancer. In some embodiments, the subject has a refractory cancer where the cancer is refractory to treatment with a covalent and/or irreversible BTK inhibitor. In some embodiments, the subject has a refractory cancer where the subject exhibits a decrease in sensitivity to treatment with a covalent and/or irreversible BTK inhibitor. In some embodiments, the subject has a refractory cancer where the subject exhibits a decrease in sensitivity to a particular dosage of a covalent and/or irreversible BTK inhibitor. In some embodiments, the subject has a refractory cancer where the subject exhibits an increase in severity or the appearance of one or more symptoms of a cancer (i.e. disease progression). In some embodiments, the subject exhibits a decrease in the regression of a cancer. In some embodiments, the regression of a cancer ceases. In some embodiments, the subject has a relapsed or refractory hematologic cancer. In some embodiments, the subject has a relapsed or refractory B-cell malignancy.

In some embodiments the subject is suspected of having a hematologic cancer or is at high risk of having a hematologic cancer. In some embodiments the subject is suspected of having a B-cell malignancy or is at high risk of having a B-cell malignancy. In some embodiments the subject is suspected of having or is at high risk of having a leukemia, a lymphoma, or a myeloma.

In some embodiments, the subject exhibits one or more symptoms of a hematologic cancer. In some embodiments, the subject exhibits one or more symptoms of a B-cell malignancy. In some embodiments, the subject exhibits one or more symptoms of a leukemia, a lymphoma, or a myeloma. In some embodiments, the subject exhibits one or more symptoms such as, but not limited to, abnormal B-cell function, abnormal B-cell size or shape, abnormal B-cell count, fatigue, fever, night sweats, frequent infection, enlarged lymph nodes, paleness, anemia, easy bleeding or bruising, loss of appetite, weight loss, bone or joint pain, headaches, and petechie.

In some embodiments, the subject is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In other embodiments, the subject is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In some embodiments, the subject has an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In some embodiments, the subject is administered or has been administered one or more therapeutic agents for treatment of a disease or condition. In some embodiments, the subject is administered or has been administered a BTK inhibitor for treatment of a disease or condition. In some embodiments, the subject is administered or has been administered one or more therapeutic agents in addition to a BTK inhibitor for treatment of a disease or condition.

In some embodiments, the subject is administered or has been administered one or more chemotherapeutic agents for treatment of cancer. In some embodiments, the subject is administered or has been administered a BTK inhibitor for treatment of a cancer. In some embodiments, the subject is administered or has been administered one or more chemotherapeutic agents in addition to a BTK inhibitor for treatment of cancer.

In some embodiments, the sample for use in the methods is from any tissue or fluid from an organism. Samples include, but are not limited, to whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In particular embodiments, the sample is a tumor biopsy sample. In particular embodiments, the sample is from a fluid or tissue that is part of, or associated with, the lymphatic system or circulatory system. In some embodiments, the sample is a blood sample that is a venous, arterial, peripheral, tissue, cord blood sample. In particular embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

Methods for the isolation of nucleic acids and proteins from cells contained in tissue and fluid samples are well-known in the art. In particular embodiments, the sample obtained from the subject is isolated from cells contained in a tumor biopsy from the subject. In particular embodiments, the sample obtained from the subject is isolated from cells in a bone marrow aspirate. In particular embodiments, the sample obtained from the subject is isolated from cells contained a serum sample. In particular embodiments, the sample obtained from the subject is isolated from cells contained in a lymph sample. In particular embodiments, the sample contains circulating tumor nucleic acid not contained in a cell.

In some embodiments, the samples are obtained from the subject by any suitable means of obtaining the sample using well-known and routine clinical methods. Procedures for obtaining fluid samples from a subject are well known. For example, procedures for drawing and processing whole blood and lymph are well-known and can be employed to obtain a sample for use in the methods provided. Typically, for collection of a blood sample, an anti-coagulation agent (e.g., EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the sample is a tissue biopsy and is obtained, for example, by needle biopsy, CT-guided needle biopsy, aspiration biopsy, endoscopic biopsy, bronchoscopic biopsy, bronchial lavage, incisional biopsy, excisional biopsy, punch biopsy, shave biopsy, skin biopsy, bone marrow biopsy, and the Loop Electrosurgical Excision Procedure (LEEP). Typically, a non-necrotic, sterile biopsy or specimen is obtained that is greater than 100 mg, but which can be smaller, such as less than 100 mg, 50 mg or less, 10 mg or less or 5 mg or less; or larger, such as more than 100 mg, 200 mg or more, or 500 mg or more, 1 gm or more, 2 gm or more, 3 gm or more, 4 gm or more or 5 gm or more. The sample size to be extracted for the assay depends on a number of factors including, but not limited to, the number of assays to be performed, the health of the tissue sample, the type of cancer, and the condition of the patient. In some embodiments, the tissue is placed in a sterile vessel, such as a sterile tube or culture plate, and is optionally immersed in an appropriate media. Typically, the cells are dissociated into cell suspensions by mechanical means and/or enzymatic treatment as is well known in the art. Typically, the cells are collected and then subjected to standard procedures for the isolation of nucleic acid for the assay.

In some embodiments, the collection of a sample from the subject is performed at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly.

In some embodiments, the collection of a sample is performed at a predetermined time or at regular intervals relative to treatment with one or more anti-cancer agents. In some embodiments, anticancer agent is administered for the treatment of a leukemia, lymphoma or a myeloma. Exemplary anti-cancer agents for the treatment of a leukemia, lymphoma or a myeloma include but are not limited to adriamycin (doxorubicin), bexxar, bendamustine, bleomycin, blenoxane, bortezomib, dacarbazine, deltasone, cisplatin, cyclophosphamide, cytoxan, DTIC dacarbazine, dasatinib, doxorubicin, etoposide, fludarabine, granisetron, kytril, lenalidomide, matulane, mechlorethamine, mustargen, mustine, natulan, Rituxan (rituximab, anti-CD20 antibody), VCR, neosar, nitrogen mustard, oncovin, ondansetron, orasone, prednisone, procarbazine, thalidomide, VP-16, velban, velbe, velsar, VePesid, vinblastine, vincristine, Zevalin®, zofran, stem cell transplantation, radiation therapy or combination therapies, such as, for example, ABVD (adriamycin, bleomycin, vinblastine and dacarbazine), ChlvPP (chlorambucil, vinblastine, procarbazine and prednisolone), Stanford V (mustine, doxorubicin, vinblastine, vincristine, bleomycin, etoposide and steroids), BEACOPP (bleomycin, etoposide, doxorubicin, cyclophosphamide, vincristine, procarbazine and prednisolone), BEAM (carmustine (BiCNU) etoposide, cytarabine (Ara-C, cytosine arabinoside), and melphalan), CHOP (cyclophosphamide, doxorubicin, vincristine, and prednisone), R-CHOP (rituximab, doxorubicin, cyclophosphamide, vincristine, and prednisone), EPOCH (etoposide, vincristine, doxorubicin, cyclophosphamide, and prednisone), CVP (cyclophosphamide, vincristine, and prednisone), ICE (ifosfamide-carboplatin-etoposide), R-ACVBP (rituximab, doxorubicin, cyclophosphamide, vindesine, bleomycin, and prednisone), DHAP (dexamethasone, high-dose cytarabine, (Ara C), cisplatin), R-DHAP (rituximab, dexamethasone, high-dose cytarabine, (Ara C), cisplatin), ESHAP (etoposide (VP-16), methyl-prednisolone, and high-dose cytarabine (Ara-C), cisplatin), CDE (cyclophosphamide, doxorubicin and etoposide), Velcade® (bortezomib) plus Doxil® (liposomal doxorubicin), Revlimid® (lenalidomide) plus dexamethasone, and bortezomib plus dexamethasone. In some embodiments, anticancer agent is fludarabine. In some embodiments, anticancer agent is bendamustine. In some embodiments, the anticancer agent is Rituxan. In some embodiments, the anticancer agent is dasatinib. In some embodiments, a sample is collected at a predetermined time or at regular intervals prior to, during, or following treatment or between successive treatments with the anti-cancer agent. In particular examples, a sample is obtained from the subject prior to administration of an anti-cancer therapy and then again at regular intervals after treatment has been effected.

In some embodiments, the collection of a sample is performed at a predetermined time or at regular intervals relative to treatment with a covalent and/or irreversible BTK inhibitor. For example, a sample is collected at a predetermined time or at regular intervals prior to, during, or following treatment or between successive treatments. In particular examples, a sample is obtained from the subject prior to administration of a covalent and/or irreversible BTK inhibitor and then again at regular intervals after treatment with the irreversible BTK inhibitor has been effected. In some embodiments, the subject is administered a covalent and/or irreversible BTK inhibitor and one or more additional anti-cancer agents. In some embodiments, the subject is administered a covalent and/or irreversible BTK inhibitor and one or more additional anti-cancer agents that are not irreversible BTK inhibitors. In some embodiments, the subject is administered one or more irreversible BTK inhibitors. In some embodiments, the irreversible BTK inhibitor is ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the irreversible BTK inhibitor is ibrutinib, PCI-45292, PCI-45466, AVL-101, AVL-291, AVL-292, ONO-WG-37 or (R)-6-amino-9-(1-but-2-ynoylpyrrolidin-3-yl)-7-(4-phenoxyphenyl)-7H-purin-8(9H)-one. In some embodiments, the irreversible BTK inhibitor is ibrutinib. In some embodiments, the irreversible BTK inhibitor is (R)-6-amino-9-(1-but-2-ynoylpyrrolidin-3-yl)-7-(4-phenoxyphenyl)-7H-purin-8(9H)-one.

Additional BTK inhibitors for use in any of the methods provided herein can be found, for example, in U.S. Pat. Nos. 7,547,689, 7,960,396 and U.S. Patent Publication Nos. US 2009-0197853 A1 and US 2012-0065201 A1, all of which are incorporated by reference in their entirety. Additional BTK inhibitors for use in any of the methods provided herein also can be found, for example, in US20100029610, WO09051822, WO10123870, WO09158571, WO11034907, WO12021444, WO11029046, WO08110624, WO10080481, WO10144647, WO10056875, WO05047290, WO06053121, WO06099075, WO08033834, WO08033857, WO08033858, WO09137596, WO10056875, WO10068788, WO10068806, WO10068810, WO11140488, WO12030990, WO12031004, WO2010056875, WO05066156, WO10056875, US20120316148, WO09048307, WO09147190, WO11162515, WO11162515, WO06036941, WO10126960, WO07136790, WO12025186, WO2013010380, WO2013010868, WO2013010869, WO2013008095, WO11152351, WO2013060098, WO2013060098, WO07002325, WO07002433, WO07013896, WO09143024, WO10065898, WO2012158764, WO2012158785, WO2012158795, WO2012158810, WO09053269, WO09156284, WO2012020008, WO2012156334, WO2013024078, WO08057252, WO03081210, WO03087051, US20130059847A1, WO06065946, WO07027594, and WO08092199 all of which are incorporated by reference in their entirety.

Further BTK inhibitors for use in any of the methods provided herein can be found, for example, in U.S. Pat. No. 7,514,444; U.S. Pat. No. 7,960,396; U.S. Pat. No. 8,236,812; U.S. Pat. No. 8,497,277; U.S. Pat. No. 8,563,563; U.S. Pat. No. 8,399,470; U.S. Pat. No. 8,088,781; U.S. Pat. No. 8,501,751; U.S. Pat. No. 8,008,309; U.S. Pat. No. 8,552,010; U.S. Pat. No. 7,732,454; U.S. Pat. No. 7,825,118; U.S. Pat. No. 8,377,946; U.S. Pat. No. 8,501,724; US Patent Pub. No. 2011-0039868; U.S. Pat. No. 8,232,280; U.S. Pat. No. 8,158,786; US Patent Pub. No. 2011-0281322; US Patent Pub. No. 2012-0088912; US Patent Pub. No. 2012-0108612; US Patent Pub. No. 2012-0115889; US Patent Pub. No. 2013-0005745; US Patent Pub. No. 2012-0122894; US Patent Pub. No. 2012-0135944; US Patent Pub. No. 2012-0214826; US Patent Pub. No. 2012-0252821; US Patent Pub. No. 2012-0252822; US Patent Pub. No. 2012-0277254; US Patent Pub. No. 2010-0022561; US Patent Pub. No. 2010-0324050; US Patent Pub. No. 2012-0283276; US Patent Pub. No. 2012-0065201; US Patent Pub. No. 2012-0178753; US Patent Pub. No. 2012-0101113; US Patent Pub. No. 2012-0101114; US Patent Pub. No. 2012-0165328; US Patent Pub. No. 2012-0184013; US Patent Pub. No. 2012-0184567; US Patent Pub. No. 2012-0202264; US Patent Pub. No. 2012-0277225; US Patent Pub. No. 2012-0277255; US Patent Pub. No. 2012-0296089; US Patent Pub. No. 2013-0035334; US Patent Pub. No. 2012-0329130; US Patent Pub. No. 2013-0018060; US Patent Pub. No. 2010-0254905; U.S. Patent App. No. 60/826,720; U.S. Patent App. No. 60/828,590; U.S. patent application Ser. No. 13/654,173; U.S. patent application Ser. No. 13/849,399; U.S. patent application Ser. No. 13/890,498; U.S. patent application Ser. No. 13/952,531; U.S. patent application Ser. No. 14/033,344; U.S. patent application Ser. No. 14/073,543; U.S. patent application Ser. No. 14/073,594; U.S. patent application Ser. No. 14/079,508; U.S. patent application Ser. No. 14/080,640; U.S. patent application Ser. No. 14/080,649; U.S. patent application Ser. No. 14/069,222; PCT App. No. PCT/US2008/58528; PCT App. No. PCT/US2012/046779; U.S. Patent App. No. 61/582,199; U.S. patent application Ser. No. 13/619,466; PCT App. No. PCT/US2012/72043; U.S. Patent App. No. 61/593,146; U.S. Patent App. No. 61/637,765; PCT App. No. PCT/US2013/23918; U.S. Patent App. No. 61/781,975; U.S. Patent App. No. 61/727,031; PCT App. No. PCT/US2013/7016; U.S. Patent App. No. 61/647,956; PCT App. No. PCT/US2013/41242; U.S. Patent App. No. 61/769,103; U.S. Patent App. No. 61/842,321; and U.S. Patent App. No. 61/884,888, all of which are incorporated herein in their entirety by reference.

In some embodiments, the subject is administered a covalent and/or irreversible BTK inhibitor that covalently binds to cysteine 481 of the wild-type BTK in combination with one or more reversible BTK inhibitors. For example, in some embodiments, the subject is administered a covalent and/or irreversible BTK inhibitor that covalently binds to cysteine 481 of the wild-type BTK in combination with one or more reversible BTK inhibitors that are not dependent on cysteine 481 for binding. Reversible BTK inhibitors are known in the art and include, but are not limited to, dasatinib, PC-005, RN486, PCI-29732 or terreic acid. In some embodiments, the irreversible BTK inhibitor ibrutinib is administered in combination with the reversible BTK inhibitor dasatinib. In some embodiments, the irreversible BTK inhibitor (R)-6-amino-9-(1-but-2-ynoylpyrrolidin-3-yl)-7-(4-phenoxyphenyl)-7H-purin-8(9H)-one is administered in combination with the reversible BTK inhibitor dasatinib.

In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 26 months, 28 months, 30 months, 32 months, 34 months, 36 months or longer following the first administration of the irreversible BTK inhibitor. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 26 months, 28 months, 30 months, 32 months, 34 months, 36 months or longer following the first administration of the irreversible BTK inhibitor to a subject naïve for exposure to the irreversible BTK inhibitor. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 26 months, 28 months, 30 months, 32 months, 34 months, 36 months or longer following the first administration of the irreversible BTK inhibitor to a subject having a relapsed or refractory cancer. In some embodiments, the sample is obtained 1, 2, 3, 4, 5, 6, 7, 8, 9, 10 times or more over the course of treatment with the irreversible BTK inhibitor. In some embodiments, the subject is responsive the treatment with the irreversible BTK inhibitor when it is first administered.

Sequencing Methods

In some embodiments, a method described herein utilizes an amplification method. In some instances, the amplification is a PCR method. In some instances, the method described herein is a high-throughput method. In some instances, the method is a next-generation sequencing method. In some instances, the next-generation sequencing method includes, but is not limited to, semiconductor sequencing (Ion Torrent; Personal Genome Machine); Helicos True Single Molecule Sequencing (tSMS) (Harris T. D. et al. (2008) Science 320:106-109); 454 sequencing (Roche) (Margulies, M. et al. 2005, Nature, 437, 376-380); SOLiD technology (Applied Biosystems); SOLEXA sequencing (Illumina); single molecule, real-time (SMRT™) technology of Pacific Biosciences; nanopore sequencing (Soni G V and Meller A. (2007) Clin Chem 53: 1996-2001); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g. Oxford Nanopore, Genia Technologies, and Nabsys).

In some aspects, the next generation sequencing comprises ion semiconductor sequencing (e.g., using technology from Life Technologies (Ion Torrent)). In some cases, ion semiconductor sequencing takes advantage of the fact that when a nucleotide is incorporated into a strand of DNA, an ion can be released. To perform ion semiconductor sequencing, a high density array of micromachined wells is formed. Each well holds a single DNA template. Beneath the well is an ion sensitive layer, and beneath the ion sensitive layer is an ion sensor. When a nucleotide is added to a DNA, H+ is released, which is measured as a change in pH. The H+ ion is converted to voltage and is recorded by the semiconductor sensor. An array chip is sequentially flooded with one nucleotide after another. No scanning, light, or cameras are required. In some embodiments, an IONPROTON™ Sequencer is used to sequence nucleic acid. In some embodiments, an IONPGM™ Sequencer is used.

In some instances, the next generation sequencing technique is 454 sequencing (Roche) (see e.g., Margulies, M et al. (2005) Nature 437: 376-380). In some cases, 454 sequencing involves two steps. In the first step, DNA is sheared into fragments of approximately 300-800 base pairs, and the fragments is blunt ended. Oligonucleotide adaptors is then ligated to the ends of the fragments. The adaptors serve as sites for hybridizing primers for amplification and sequencing of the fragments. The fragments are attached to DNA capture beads, e.g., streptavidin-coated beads using, e.g., Adaptor B, which contains 5'-biotin tag. The fragments are attached to DNA capture beads through hybridization. A single fragment is captured per bead. The fragments attached to the beads are PCR amplified within droplets of an oil-water emulsion. The result is multiple copies of clonally amplified DNA fragments on each bead. The emulsion is broken while the amplified fragments remain bound to their specific beads. In a second step, the beads are captured in wells (pico-liter sized; PicoTiterPlate (PTP) device). The surface is designed so that only one bead fits per well. The PTP device is loaded into an instrument for sequencing. Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing uses pyrophosphate (PPi) which is released upon nucleotide addition. PPi is converted to ATP by ATP sulfurylase in the presence of adenosine 5' phosphosulfate. Luciferase then uses ATP to convert luciferin to oxyluciferin, and this reaction generates light that is detected and analyzed. In some instances, the 454 Sequencing system used includes GS FLX+ system or the GS Junior System.

In some instances, the next generation sequencing technique is SOLiD technology (Applied Biosystems; Life Technologies). In SOLiD sequencing, genomic DNA is sheared into fragments, and adaptors are attached to the 5' and 3' ends of the fragments to generate a fragment library. Alternatively, internal adaptors are introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. A sequencing primer binds to adaptor sequence. A set of four fluorescently labeled di-base probes competes for ligation to the sequencing primer. Specificity of the di-base probe is achieved by interrogating every first and second base in each ligation reaction. The sequence of a template is determined by sequential hybridization and ligation of partially random oligonucleotides with a determined base (or pair of bases) that is identified by a specific fluorophore. After a color is recorded, the ligated oligonucleotide is cleaved and removed and the process is then repeated. Following a series of ligation cycles, the extension product is removed and the template is reset with a primer complementary to the n-1 position for a second round of ligation cycles. Five rounds of primer reset are completed for each sequence tag. Through the primer reset process, most of the bases are interrogated in two independent ligation reactions by two different primers. In some instances, up to 99.99% accuracy are achieved by sequencing with an additional primer using a multi-base encoding scheme.

In some embodiments, the next generation sequencing technique is SOLEXA sequencing (ILLUMINA sequencing). ILLUMINA sequencing is based on the amplification of DNA on a solid surface using fold-back PCR and anchored primers. ILLUMINA sequencing involves a library preparation step, a cluster generation step, and a sequencing step. During the library preparation step, genomic DNA is fragmented, and sheared ends is repaired and adenylated. Adaptors are added to the 5' and 3' ends of the fragments. The fragments are then size selected and purified. During the cluster generation step, DNA fragments are attached to the surface of flow cell channels by hybridizing to a lawn of oligonucleotides attached to the surface of the flow cell channel. The fragments are extended and clonally amplified through bridge amplification to generate unique clusters. The fragments become double stranded, and the double stranded molecules are denatured. Multiple cycles of the solid-phase amplification followed by denaturation create several million clusters of approximately 1,000 copies of single-stranded DNA molecules of the same template in each channel of the flow cell. Reverse strands are cleaved and washed away. Ends are blocked, and primers hybridized to DNA templates. During the sequencing step, hundreds of millions of clusters are sequenced simultaneously. Primers, DNA polymerase and four fluorophore-labeled, reversibly terminating nucleotides are used to perform sequential sequencing. All four bases compete with each other for the template. After nucleotide incorporation, a laser is used to excite the fluorophores, and an image is captured and the identity of the first base is recorded. The 3' terminators and fluorophores from each incorporated base are removed and the incorporation, detection and identification steps are repeated. A single base is read each cycle. In some instances, a HiSeq system (e.g., HiSeq 2500, HiSeq 1500, HiSeq 2000, or HiSeq 1000) is used for sequencing. In some instances, a MiSeq personal sequencer is used. In some instances, a NextSeq system is used. In some instances, a Genome Analyzer IIx is used.

In some embodiments, the next generation sequencing technique comprises real-time (SMRT™) technology by Pacific Biosciences. In SMRT, each of four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that is rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. The ZMW is illuminated from below. Attenuated light from an excitation beam penetrates the lower 20-30 nm of each ZMW. A microscope with a detection limit of 20 zeptoliters ($10^{-21}$ liters) is created. The tiny detection volume provides 1000-fold improvement in the reduction of background noise. Detection of the corresponding fluorescence of the dye indicates which base is incorporated.

In some instances, the next generation sequencing is nanopore sequencing (See e.g., Soni G V and Meller A. (2007) Clin Chem 53: 1996-2001). A nanopore is a small hole, of the order of about one nanometer in diameter. Immersion of a nanopore in a conducting fluid and application of a potential across results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence. In some instances, the nanopore sequencing technology is from Oxford Nanopore Technologies; e.g., a GridION system. A single nanopore is inserted in a polymer membrane across the top of a microwell. Each microwell has an electrode for individual sensing. The microwells are fabricated into an array chip, with 100,000 or more microwells (e.g., more than about 200,000, 300,000, 400,000, 500,000, 600,000, 700,000, 800,000, 900,000, or 1,000,000) per chip. An instrument (or node) is used to analyze the chip. Data is analyzed in real-time. One or more instruments are operated at a time. In some cases, the nanopore is a protein nanopore, e.g., the protein alpha-hemolysin, a heptameric protein pore. In some instances, the nanopore is a solid-state nanopore made, e.g., a nanometer sized hole formed in a synthetic membrane (e.g., SiNx, or $SiO_2$). In some instances, the nanopore is a hybrid pore (e.g., an integration of a protein pore into a solid-state membrane). In some cases, the nanopore is a nanopore with an integrated sensors (e.g., tunneling electrode detectors, capacitive detectors, or graphene based nano-gap or edge state detectors (see e.g., Garaj et al. (2010) Nature vol. 67, doi:10.1038/nature09379)). In some aspects, the nanopore is functionalized for analyzing a specific type of molecule (e.g., DNA, RNA, or protein). In some cases, nanopore sequencing comprises "strand sequencing" in which intact DNA polymers pass through a protein nanopore with sequencing in real time as the DNA translocates the pore. An enzyme separates strands of a double stranded DNA and feed a strand through a nanopore. In some cases, the DNA has a hairpin at one end, and the system reads both strands. In some embodiments, nanopore sequencing is "exonuclease sequencing" in which individual nucleotides is cleaved from a DNA strand by a processive exonuclease, and the nucleotides are passed through a protein nanopore. The nucleotides transiently bind to a molecule in the pore (e.g., cyclodextran). A characteristic disruption in current is used to identify bases.

In some instances, nanopore sequencing technology from GENIA is used. An engineered protein pore is embedded in a lipid bilayer membrane. "Active Control" technology is used to enable efficient nanop ore-membrane assembly and control of DNA movement through the channel. In some embodiments, the nanopore sequencing technology is from NABsys. Genomic DNA is fragmented into strands of average length of about 100 kb. The 100 kb fragments are made single stranded and subsequently hybridized with a 6-mer probe. The genomic fragments with probes are driven through a nanopore, which creates a current-versus-time tracing. The current tracing provides the positions of the probes on each genomic fragment. The genomic fragments are lined up to create a probe map for the genome. The process is done in parallel for a library of probes. A genome-length probe map for each probe is generated. Errors are fixed with a process termed "moving window Sequencing By Hybridization (mwSBH)." In some embodiments, the nanopore sequencing technology is from IBM/Roche. An electron beam is used to make a nanopore sized opening in a microchip. An electrical field is used to pull or thread DNA through the nanopore. A DNA transistor device in the nanopore comprises alternating nanometer sized layers of metal and dielectric. Discrete charges in the DNA backbone get trapped by electrical fields inside the DNA nanopore. Turning off and on gate voltages allow the DNA sequence to be read.

In some instances, the next generation sequencing is DNA nanoball sequencing (as performed, e.g., by Complete Genomics; see e.g., Drmanac et al. (2010) Science 327: 78-81). DNA is isolated, fragmented, and size selected. For example, DNA is fragmented (e.g., by sonication) to a mean length of about 500 bp. Adaptors (Ad1) are attached to the ends of the fragments. The adaptors are used to hybridize to anchors for sequencing reactions. DNA with adaptors bound to each end is PCR amplified. The adaptor sequences are modified so that complementary single strand ends bind to each other forming circular DNA. The DNA is methylated to protect it from cleavage by a type IIS restriction enzyme used in a subsequent step. An adaptor (e.g., the right adaptor) has a restriction recognition site, and the restriction recognition site remains non-methylated. The non-methylated restriction recognition site in the adaptor is recognized by a restriction enzyme (e.g., AcuI), and the DNA is cleaved by AcuI 13 bp to the right of the right adaptor to form linear double stranded DNA. A second round of right and left adaptors (Ad2) are ligated onto either end of the linear DNA, and all DNA with both adapters bound can be PCR amplified (e.g., by PCR). Ad2 sequences are modified to allow them to bind each other and form circular DNA. The DNA is methylated, but a restriction enzyme recognition site remains non-methylated on the left Ad1 adapter. A restriction enzyme (e.g., AcuI) is applied, and the DNA is cleaved 13 bp to the left of the Ad1 to form a linear DNA fragment. A third round of right and left adaptor (Ad3) is ligated to the right and left flank of the linear DNA, and the resulting fragment is PCR amplified. The adaptors are modified so that they bind to each other and form circular DNA. A type III restriction enzyme (e.g., EcoP15) is added; EcoP15 cleaves the DNA 26 bp to the left of Ad3 and 26 bp to the right of Ad2. This cleavage removes a large segment of DNA and linearize the DNA once again. A fourth round of right and left adaptors (Ad4) is ligated to the DNA, the DNA is amplified (e.g., by PCR), and modified so that they bind each other and form the completed circular DNA template.

Rolling circle replication (e.g., using Phi 29 DNA polymerase) is used to amplify small fragments of DNA. The four adaptor sequences contain palindromic sequences that hybridize and a single strand fold onto itself to form a DNA nanoball (DNB™) which in some cases, is approximately 200-300 nanometers in diameter on average. A DNA nanoball is attached (e.g., by adsorption) to a microarray (sequencing flowcell). The flow cell is a silicon wafer coated with silicon dioxide, titanium and hexamethyldisilazane (HMDS) and a photoresist material. Sequencing is performed by unchained sequencing by ligating fluorescent probes to the DNA. The color of the fluorescence of an interrogated position is visualized by a high resolution camera. The identity of nucleotide sequences between adaptor sequences is determined.

In some embodiments, the next generation sequencing technique is Helicos True Single Molecule Sequencing (tSMS) (see e.g., Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contain millions of oligo-T capture sites immobilized to the flow cell surface. The templates are at a density of about 100 million templates/$cm^2$. The flow cell is then loaded into an instrument, e.g., HELISCOPE™ sequencer, and a laser illuminate the surface of the flow cell, revealing the position of each template. A CCD camera maps the position of the templates on the flow cell surface. The template fluorescent label is cleaved and washed away. The sequencing reaction begins by introducing a DNA polymerase and a fluorescently labeled nucleotide. The oligo-T nucleic acid serves as a primer. The DNA polymerase incorporates the labeled nucleotides to the primer in a template directed manner. The DNA polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until a desired read length is achieved. Sequence information is collected with each nucleotide addition step. The sequencing is asynchronous. The sequencing comprises at least 1 billion bases per day or per hour.

In some embodiments, a sequencing technique comprises paired-end sequencing in which both the forward and reverse template strand is sequenced. In some embodiments, the sequencing technique comprises mate pair library sequencing. In mate pair library sequencing, DNA comprises fragments, and 2-5 kb fragments are end-repaired (e.g., with biotin labeled dNTPs). The DNA fragments are circularized, and non-circularized DNA are removed by digestion. Circular DNA are fragmented and purified (e.g., using the biotin labels). Purified fragments are end-repaired and ligated to sequencing adaptors.

In some embodiments, a sequencing method comprises Sanger sequencing, Maxam-Gilbert sequencing, Shotgun sequencing, bridge PCR, mass spectrometry based sequencing, microfluidic based Sanger sequencing, microscopy-based sequencing, RNAP sequencing, or hybridization based sequencing. Sanger sequencing utilizes a chain-termination method which relies on selective incorporation of chain-terminating dideoxynucleotides by DNA polymerases during replication. Maxam-Gilbert sequencing utilizes chemical modification of DNA and subsequent cleavage at specific bases. In a shotgun sequencing method, DNA is randomly fragmented and then sequenced using chain termination methods to obtain reads. Multiple overlapping reads are pooled and assembled into a continuous sequence. In a bridge PCR method, DNA is fragmented and then amplified by solid surface tethered primers to form "DNA colonies" or "DNA clusters". Multiple overlapping "DNA colonies" or "DNA clusters" are pooled and assembled into a continuous sequence. In a mass spectrometry-based sequencing, DNA fragments are generated by chain-termination sequencing methods and the fragments are read by mass spectrometries such as matrix-assisted laser desorption ionization time-of-flight mass spectrometry (MALDI-TOF MS). In a microfluidic Sanger sequencing method, amplification of the DNA fragments and their separation are achieved on a single glass wafer. In a microscopy-based method, electron microscopy such as transmission electron microscopy DNA sequencing are used to visualize DNA bases labeled with heavy atoms. A RNAP sequencing method utilizes the distinct motions that RNA polymerase generates during transcription of each nucleotide base and generates a sequence based on this motion. A hybridization-based sequencing utilizes a DNA microarray in which a single pool of DNA of interest is fluorescently labeled and hybridized to an array containing known sequences. Strong hybridization signals from a particular spot on the array allow identification of the sequence of the DNA of interest.

In some instances, amplification methodologies are used to amplify the nucleic acid sequences. Exemplary amplification methodologies include, but are not limited to, polymerase chain reaction (PCR), nucleic acid sequence based amplification (NASBA), self-sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR, ligation mediated PCR, or methylation specific PCR.

In some instances, additional methods that are used to obtain a nucleic acid sequence include, e.g., array-based comparative genomic hybridization, detecting single nucleotide polymorphisms (SNPs) with arrays, subtelomeric fluorescence in situ hybridization (ST-FISH) (e.g., to detect submicroscopic copy-number variants (CNVs)), DNA microarray, high-density oligonucleotide microarray, whole-genome RNA expression array, peptide microarray, enzyme-linked immunosorbent assay (ELISA), genome sequencing, de novo sequencing, Pacific Biosciences SMRT sequencing, Genia Technologies nanopore single-molecule DNA sequencing, Oxford Nanopore single-molecule DNA sequencing, polony sequencing, copy number variation (CNV) analysis sequencing, small nucleotide polymorphism (SNP) analysis, immunohistochemistry (IHC), immunocytochemistry (ICC), mass spectrometry, tandem mass spectrometry, matrix-assisted laser desorption ionization time of flight mass spectrometry (MALDI-TOF MS), in-situ hybridization, fluorescent in-situ hybridization (FISH), chromogenic in-situ hybridization (CISH), silver in situ hybridization (SISH), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, and Northern blotting.

Maintenance Therapy

Provided herein are methods for maintenance therapy of subject having a B-cell proliferative disorder. In some embodiments, B-cell proliferative disorder is cancer. In some embodiments, the cancer is hematologic cancer. In some embodiments, the methods for maintenance therapy comprise treating a hematologic cancer with a covalent and/or irreversible BTK inhibitor for an initial treatment period, followed by a maintenance therapy regimen. In some embodiments, the methods for maintenance therapy comprise treating a hematologic cancer with a covalent and/or irreversible BTK inhibitor for a period of six months or longer, such as, for example, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 3 years, 4 years, 5 years, 6 years, 7 years, 8 years, 9 years, 10 years or longer. In some embodiments, the irreversible BTK inhibitor covalently binds to cysteine 481 of the wild-type BTK. In some embodiments, the irreversible BTK inhibitor is selected from among ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the irreversible BTK inhibitor is selected from among ibrutinib, PCI-45292, PCI-45466, AVL-101, AVL-291, AVL-292, ONO-WG-37 or (R)-6-amino-9-(1-but-2-ynoylpyrrolidin-3-yl)-7-(4-phenoxyphenyl)-7H-purin-8(9H)-one. In some embodiments, the irreversible BTK inhibitor is ibrutinib. In some embodiments, the irreversible BTK inhibitor is (R)-6-amino-9-(1-but-2-ynoylpyrrolidin-3-yl)-7-(4-phenoxyphenyl)-7H-purin-8(9H)-one.

In some embodiments, provided is a method of maintenance therapy in a patient having a hematologic cancer, comprising: (a) administering to the patient a maintenance therapy regimen comprising administering a therapeutically effective dose of a BTK inhibitor; and (b) monitoring the patient at predetermined intervals of time over the course of the maintenance therapy regimen to determine whether the subject has mutation in an endogenous gene encoding PLCγ2 that results in a modification at an amino acid position corresponding to amino acid position 742, 845, or 1140 of the amino acid sequence set forth in SEQ ID NO: 2. In some embodiments, the modification in the PLCγ2 polypeptide is R742P. In some embodiments, the modification in the PLCγ2 polypeptide is L845F. In some embodiments, the modification in the PLCγ2 polypeptide is D1140G. In some embodiments, the modification in the PLCγ2 polypeptide further comprises additional modifications. In some embodiments, the method further comprises determining whether the subject has mutations in PLCγ2 and an additional polypeptide. In some embodiments, the additional polypeptide is a polypeptide that encoded by a gene associated in the BCR pathway. In some embodiments, the additional polypeptide is BTK. In some embodiments, the additional mutation results in a modified BTK polypeptide having an amino acid substitution at C481. In some embodiments, the additional mutation results in a modified BTK polypeptide having an amino acid substitution selected from among C481F, C481S, C481Y, and C481R. In some embodiments, the additional mutation results in a modified BTK polypeptide having an amino acid substitution at L527. In some embodiments, the additional mutation results in a modified BTK polypeptide having an amino acid substitution that is L527W. In some embodiments, the addition mutation is in a gene is selected from TP53, c-MYC, BCL6, IGHV, CD38, CSF1, DAB1, ARTN, COL8A2 or LDLRAP1 located on chromosome 1; PRR21, NDUFA10, ASIC4, POTEE or XPO1 located on chromosome 2; RAB6B, TMPRSS7 or CACNA1D located on chromosome 3; GUCY1B3, MAML3, FRAS1 or EVC2 located on chromosome 4; NPM1, G3BP1, H2AFY, HEATR7B2 or ADAMTS12 located on chromosome 5; KIAA1244, ENPP1, NKAIN2, REV3L, COL12A1 or IRF4 located on chromosome 6; ZNF775, SSPO, ZNF777 or ABCA13 located on chromosome 7; TRPS1 located on chromosome 8; UAP1L1, AGPAT2, SNAPC4, RALGPS1 or GNAQ located on chromosome 9; PIK3AP1, EGR2 or NRP1 located on chromosome 10; KRTAP5-9, CAPN1 or MUC2 located on chromosome 11; DPY19L2, KRT73, SLC11A2, MLL2, SYT10 or OVOS2 located on chromosome 12; TRPC4 located on chromosome 13; SLC8A3 located on chromosome 14; BLM, DISP2 or C15orf55 located on chromosome 15; MMP25 or MAPK8IP3 located on chromosome 16; LLGL2, KRTAP9-3, TRAF4, CENPV or TP53 located on chromosome 17; CEACAM18, SPIB, TPRX1, DMKN, LSM4, CACNA1A, CCDC151, LONP1 or STAP2 located on chromosome 19; TSPEAR, KCNJ15, DYRK1A or IFNAR1 located on chromosome 21; SLC5A4 or HIRA located on chromosome 22; or BTK, IL13RA2, MAGEE1, SHROOM4 or NYX located on chromosome X. In some embodiments, the method further comprises discontinuing maintenance therapy regimen if the subject has one or more mutations with at least one modification at amino acid position 742, 845, or 1140 in PLCγ2 polypeptide. In some embodiments, the method further comprises discontinuing maintenance therapy regimen if the subject has no mutation at amino acid position 742, 845, or 1140 in PLCγ2 polypeptide but has additional mutations in PLCγ2 polypeptide and/or has mutations in an additional polypeptide. In some embodiments, the method further comprises administering an inhibitor of PLCγ2 if the subject has one or more modifications with at least one modification at amino acid position 742, 845, or 1140 in the PLCγ2 polypeptide. In some embodiments, the method further comprises administering an inhibitor of LYN, SYK, JAK, PI3K, MAPK, MEK or NFκB if the subject has one or more modifications with at least one modification at amino acid position 742, 845, or 1140 in PLCγ2 polypeptide. In some embodiments, the method further comprises continuing maintenance therapy regimen if the subject has no mutations in the PLCγ2 polypeptide. In some embodiments, the method further comprises continuing maintenance therapy regimen if the subject has no mutations in the PLCγ2 polypeptide but has mutations in an additional polypeptide. In some embodiments, the method further comprises continuing maintenance therapy regimen if the subject has no mutations in the PLCγ2 polypeptide or in the additional polypeptide. In some embodiments, the additional polypeptide is a BTK polypeptide. In some embodiments, the predetermined interval of time is every month, every 2 months, every 3 months, every 4 months, every 5 months, every 6 months, every 7 months or every 8 months.

In some embodiments, the BTK inhibitor is administered at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, ibrutinib is administered at a daily dosage of about 140 mg per day, 420 mg per day, 560 mg per day or 840 mg per day. In some embodiments, the BTK inhibitor is a covalent and/or irreversible BTK inhibitor. In some embodiments, the BTK inhibitor is selected from among ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK417891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), JTE-051 (Japan Tobacco Inc), PRN1008 (Principia), CTP-730 (Concert Pharmaceuticals), or GDC-0853 (Genentech). In some embodiments, the BTK inhibitor is selected from among ibrutinib (PCI-32765), PCI-45292, PCI-45466, AVL-101, AVL-291, AVL-292, ONO-WG-37 or (R)-6-amino-9-(1-but-2-ynoylpyrrolidin-3-yl)-7-(4-phenoxyphenyl)-7H-purin-8(9H)-one. In some embodiments, the BTK inhibitor is ibrutinib. In some embodiments, the BTK inhibitor is (R)-6-amino-9-(1-but-2-ynoylpyrrolidin-3-yl)-7-(4-phenoxyphenyl)-7H-purin-8(9H)-one.

In some embodiments, the subject is monitored every month, every 2 months, every 3 months, every 4 months, every 5 months, every 6 months, every 7 months, every 8 months, every 9 months, every 10 months, every 11 months, or every year to determine whether the subject acquires mutation in an endogenous gene encoding PLCγ2 that results in modifications at R742, L845, D1140 of the PLCγ2 polypeptide.

In some embodiments, the subject possesses high-risk cytogenetic features. In some embodiments, the subject possessing high-risk cytogenetic features has cytogenetic abnormalities selected from trisomy 12, del(11q22.3), del(13q14.3), del(17p13.1), t(11;14)(q13;q32), t(14;19)(q32;q13) or t(2;14)(p13;q32). In some embodiments, the subject possessing high-risk cytogenetic features has del(11q22.3), del(17p13.1) or a complex karyotype. In some embodiments, the subject possessing high-risk cytogenetic features has del(11q22.3). In some embodiments, the subject possessing high-risk cytogenetic features has del(17p13.1). In some embodiments, the subject possessing high-risk cytogenetic features has a complex karyotype.

In some embodiments, the subject has cancer. In some embodiments, the cancer is a hematologic cancer. In some embodiments, the cancer is a B-cell malignancy. In some embodiments, cancer is selected from among a leukemia, a lymphoma, or a myeloma. In some embodiments, the hematologic cancer is a B-cell malignancy. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor. In some embodiments, the B-cell malignancy is chronic lymphocytic leukemia (CLL).

In some embodiments, maintenance therapy comprises multiple cycles of administration. In some embodiments, a cycle of administration is one month, 2 months, 3 months, 4 months, 6 months, 6 months, 7 months, 8 months, 9 months, 10 months, 11 months, 12 months or longer. In some embodiments, a cycle of administration comprises administration of a single therapeutic dosage of the irreversible BTK inhibitor over the cycle. In some embodiments, a cycle of administration comprises two or more different dosages of the irreversible BTK inhibitor over the cycle. In some embodiments, the dosage of the irreversible BTK inhibitor differs over consecutive cycles. In some embodiments, the dosage of the irreversible BTK inhibitor increases over consecutive cycles. In some embodiments, the dosage of the irreversible BTK inhibitor is the same over consecutive cycles.

In some embodiments, maintenance therapy comprises administration of a daily dosage of the irreversible BTK inhibitor. In some embodiments, the daily dosage of the irreversible BTK inhibitor administered is at or about 10 mg per day to about 2000 mg per day, such as for example, about 50 mg per day to about 1500 mg per day, such as for example about 100 mg per day to about 1000 mg per day, such as for example about 250 mg per day to about 850 mg per day, such as for example about 300 mg per day to about 600 mg per day. In a particular embodiment, the maintenance dosage of the irreversible BTK inhibitor is about 840 mg per day. In a particular embodiment, where the irreversible inhibitor is ibrutinib, the maintenance dosage is about 840 mg ibrutinib per day. In a particular embodiment, the maintenance dosage of the irreversible BTK inhibitor is about 560 mg per day. In a particular embodiment, where the irreversible inhibitor is ibrutinib, the maintenance dosage is about 560 mg ibrutinib per day. In a particular embodiment, the maintenance dosage is about 420 mg per day. In a particular embodiment, where the irreversible inhibitor is ibrutinib, the maintenance dosage is about 420 mg ibrutinib per day. In a particular embodiment, the maintenance dosage of the irreversible BTK inhibitor is about 140 mg per day. In a particular embodiment, where the irreversible inhibitor is ibrutinib, the maintenance dosage is about 140 mg ibrutinib per day.

In some embodiments, the irreversible BTK inhibitor is administered once per day, two times per day, three times per day or more frequent. In a particular embodiment, the irreversible BTK inhibitor is administered once per day. In some embodiments, the irreversible BTK inhibitor that is ibrutinib is administered once per day, two times per day, three times per day or more frequent. In a particular embodiment, the irreversible BTK inhibitor that is ibrutinib is administered once per day.

In some embodiments, the dosage of the irreversible BTK inhibitor is escalated over time. In some embodiments, the dosage of the irreversible BTK inhibitor that is ibrutinib is escalated over time. In some embodiments, the dosage of the irreversible BTK inhibitor is escalated from at or about 1.25 mg/kg/day to at or about 12.5 mg/kg/day over a predetermined period of time. In some embodiments, the dosage of the irreversible BTK inhibitor that is ibrutinib is escalated from at or about 1.25 mg/kg/day to at or about 12.5 mg/kg/day over a predetermined period of time. In some embodiments the predetermined period of time is over 1 month, over 2 months, over 3 months, over 4 months, over 5 months, over 6 months, over 7 months, over 8 months, over 9 months, over 10 months, over 11 months, over 12 months, over 18 months, over 24 months or longer.

In some embodiments, a cycle of administration comprises administration of the irreversible BTK inhibitor in combination with an additional therapeutic agent. In some embodiments the additional therapeutic is administered simultaneously, sequentially, or intermittently with the irreversible BTK inhibitor. In some embodiments the additional therapeutic agent is an anti-cancer agent. In some embodiments the additional therapeutic agent is an anti-cancer agent for the treatment of a leukemia, lymphoma or a myeloma. Exemplary anti-cancer agents for administration in a combination with a covalent and/or irreversible BTK inhibitor are provided elsewhere herein. In a particular embodiment, the anti-cancer agent is an anti-CD 20 antibody (e.g., Rituxan). In a particular embodiment, the anti-cancer agent bendamustine. In some embodiments, the additional anti-cancer agent is a reversible BTK inhibitor. In some embodiments, the additional anti-cancer agent is a reversible BTK inhibitor that does not depend on cysteine 481 for binding to BTK. In some embodiments, the additional anti-cancer agent is dasatinib.

Identification of Molecules that Interact with Mutant PLCγ2

Provided herein are methods of screening compounds that inhibit a modified PLCγ2, comprising: (a) providing a modified PLCγ2, wherein the modified PLCγ2 is modified at amino acid position corresponding to amino acid position 742, 845, or 1140 of the amino acid sequence set forth in SEQ ID NO: 2; (b) contacting the modified PLCγ2 with a test compound; and (c) detecting the level of PLCγ2 activity, wherein a decrease in activity indicates that the compound inhibits the modified PLCγ2. In some embodiments, the modification is a substitution, addition or deletion of the amino acid at position 742, 845, or 1140 of the PLCγ2 polypeptide. In some embodiments, detecting the level of PLCγ2 activity is assessed by an in vitro assay (e.g., calcium flux assay, co-localization assay or kinase assay). In some embodiments, detecting the level of PLCγ2 activity is assessed by measuring the level of calcium within a cell. In some embodiments, the cell is a B lymphocyte, a monocyte, or a macrophage. In some embodiments, the cell is a cancer cell line, such as a lymphoma, leukemia, or myeloma cell line. In some embodiments, the cell line is a MCL, DBCL or a follicular lymphoma cell line. In some embodiments, the cell line is a BTK knockout B lymphoma cell line, such as the DT40 BTK knockout cell line. In some embodiments, antibodies are used to detect the level and location of particular PLCγ2 targets. In some embodiments, the cells are first stimulated to activate BCR signaling pathway prior to, during or following exposure to the test compound. In some embodiments, the cells are first stimulated with anti-IgM or anti-IgG to activate BCR signaling pathway prior to, during or following exposure to the test compound.

In some embodiments, a host cell line that can be transfected with nucleic acid encoding the modified PLCγ2 polypeptide and in which PLCγ2 activity can be monitored is used in the method. In some embodiments, the host cell does not express wild-type PLCγ2. In some embodiments, the host cell is deficient for the expression of endogenous wild-type PLCγ2. In some embodiments, the host cell expressing the modified PLCγ2 polypeptide stably expresses the modified PLCγ2 polypeptide. In some embodiments, the nucleic acid encoding the modified PLCγ2 polypeptide is integrated into the genome of the cell.

In some embodiments, the host cell is a chicken DT40 BTK B cell. In some embodiments, the cell is a non B-cell. In some embodiments, the cell is a mammalian non-B-cell. In some embodiments, the cell is a 293 cell. In some embodiments, the cell is a non-mammalian cell. In some embodiments, the cell is an insect cell, a bacterial cell, a yeast cell, or a plant cell.

Cellular functional assays for BTK inhibition include measuring one or more cellular endpoints in response to stimulating a PLCγ2-mediated pathway in a cell line in the absence or presence of a range of concentrations of a candidate PLCγ2 inhibitor compound. Useful endpoints for determining a response to BCR activation include, e.g., inhibition of IP2 into IP3 or cytoplasmic calcium flux.

In some embodiments, a downstream transcription target assay is employed to determine BTK activity in the presence or absence of the test compounds. In some embodiments, the downstream transcription target assay is an NF-κB based assay. In some example, a gene encoding a reporter protein is operably linked to an NF-κB responsive promoter that is sensitive to BCR pathway signaling and is inhibited when BTK is inhibited. In some embodiments, the reporter gene encodes a protein selected from among a luciferase, a fluorescent protein, a bioluminescent protein, or an enzyme. In some embodiments, the assay comprises a host cell that contains the reporter and the mutant BTK. Detection of the level of gene expression in the presence or absence of the test compound indicates whether the test compound inhibits the BCR pathway in the presence of the mutant BTK. In some embodiments, the test compound inhibits the mutant PLCγ2 directly.

High throughput assays for many cellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including sample and reagent pipetting, liquid dispensing, timed incubations, and final readings of the microplate in detector(s) appropriate for the assay. Automated systems thereby allow the identification and characterization of a large number of BTK inhibitor compounds without undue effort.

In some embodiments, detecting the level of PLCγ2 activity is assessed by an in vivo assay. In some embodiments, detecting the level of PLCγ2 activity is assessed in animal model. In some embodiments the animal model is one that is a mouse model of leukemia. Such animal model is well-known in the art and includes, for example, mouse models, of AML and CLL (see, e.g., Zuber, (2009) *Genes and Development* 23(7):877-89 and Pekarsky et al. (2007) *J*

*Cell Biochem.* 100(5):1109-18. In some embodiments the animal model is a transgenic animal that expresses a modified PLCγ2 that is modified at R742, L845, or D1140. In some embodiments, a test compound is administered to a transgenic animal that expresses a modified PLCγ2 that is modified at R742, L845, or D1140 and the activity of PLCγ2 is assessed by one or more assays described herein. In some embodiments, the assay is performed with the mutant PLCγ2 polypeptide isolated from the transgenic animal administered the test compound and compared to a control. In some embodiments, the level of phosphorylation, translocation or calcium flux of one or more BTK targets is assessed in a B-cell sample from the transgenic animal administered the test compound and compared to a control. In some embodiments, the control is a sample from an animal not administered the test compound. In some embodiments, the control is a sample from an animal administered a covalent and/or irreversible BTK inhibitor.

Kits and Articles of Manufacture

For use in the diagnostic and therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

Described herein, in certain embodiments, is a kit comprising one or more reagents for the detection of a modified PLCγ2 polypeptide comprising a modification at amino acid position 742, 845, or 1140. In some embodiments, the kit comprises a microchip comprising a mutant PLCγ2 polypeptide having a modification that is R742P, L845F, or D1140G.

Described herein, in certain embodiments, is a kit comprising one or more reagents for the detection of nucleic acid encoding a mutant PLCγ2 polypeptide comprising a modification at amino acid position 742, 845, or 1140. In some embodiments, the kit comprises a microchip comprising nucleic acid encoding a mutant PLCγ2 polypeptide having a modification that is R742P, L845F, or D1140G.

In some embodiments, the kits provided herein are for use in detecting nucleic acid encoding modified PLCγ2 polypeptide in a subject or for detecting modified PLCγ2 polypeptide in a subject. In some embodiments, the kits provided herein are for use as a companion diagnostic with one or more covalent and/or irreversible BTK inhibitors. In some embodiments the kits are employed for selecting patients for treatment with a PLCγ2 inhibitor, for identifying subjects as resistant or likely to become resistant to a covalent and/or irreversible BTK inhibitor, for monitoring the development of resistance to a covalent and/or irreversible BTK inhibitor, or combinations thereof. The kits provided herein contain one or more reagents for the detection of the nucleic acid encoding modified PLCγ2 polypeptide, for the detection of modified PLCγ2 polypeptide, for detection of PLCγ2 activities in cells from the subject, for detection of PLCγ2 activities in vitro or in vivo or combinations thereof. Exemplary reagents include but are not limited to, oligonucleotide, PCR reagents, buffers, antibodies, BTK substrates for determining kinase activity, substrates for enzymatic staining, chromagens or other materials, such as slides, containers, microtiter plates, and optionally, instructions for performing the methods. Those of skill in the art will recognize many other possible containers and plates and reagents that can be used for contacting the various materials. Kits also can contain control samples, such as for example, nucleic acids or proteins, such as for example a mutant PLCγ2 polypeptide provided herein or nucleic acids encoding a modified PLCγ2 polypeptide provided herein. In some embodiments, kits contain one or more set of oligonucleotide primers for detection of mutant PLCγ2 expression.

In some embodiments, the container(s) can comprise one or more inhibitors of PLCγ2 identified by the methods described herein, optionally in a composition or in combination with another agent as disclosed herein. The container(s) optionally have materials, such as syringes, needles, dosing cups or vials, for administration. Such kits optionally comprise a compound with an identifying description or label or instructions relating to its use in the methods described herein.

In some embodiment, a kit comprises a modified PLCγ2 polypeptide or a variant thereof having PLCγ2 activity comprising a modification at amino acid position corresponding to amino acid position 742, 845, or 1140 of the amino acid sequence set forth in SEQ ID NO: 2. In some embodiments, a kit comprises an isolated nucleic acid of any encoding a modified BTK polypeptide provided herein or a vector comprising such nucleic acid.

In some embodiment, a kit comprises a microchip comprising the modified PLCγ2 polypeptide provided herein or the nucleic acid encoding modified PLCγ2 polypeptide provided herein. In some embodiments, the modification is a substitution at amino acid position 742, 845, or 1140 of the PLCγ2 polypeptide.

Production of Nucleic Acids and Polypeptides

In some embodiments, an isolated nucleic acid molecule encoding a mutant PLCγ2 polypeptide provided herein is generated by standard recombinant methods. In some embodiments, an isolated nucleic acid molecule encoding a mutant PLCγ2 polypeptide provided herein is generated by amplification of a mutant PLCγ2 sequence from genomic DNA. In some embodiments, an isolated nucleic acid molecule encoding a mutant PLCγ2 polypeptide provided herein is generated by polymerase chain reaction using PLCγ2 sequence specific primers.

In some embodiments, an isolated nucleic acid molecule encoding a mutant PLCγ2 polypeptide provided herein is inserted into an expression vector and expressed in a host cell or a non-cell extract. In some embodiments, an isolated nucleic acid molecule encoding a mutant PLCγ2 polypeptide provided herein is operatively linked to a promoter for expression of the encoding polypeptide in a cell or non-cell extract. In some embodiments, the promoter is a constitutive promoter. In some embodiments, the promoter is an inducible promoter.

In some embodiments, the nucleic acid molecule encoding a mutant PLCγ2 polypeptide provided herein is "exogenous" to a cell, which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

Methods for the expression of a protein in a cell are well known in the art and include, for example, expression in cells, such as animal and plant cells. Exemplary animal cells for the expression of mutant PLCγ2 polypeptide provided herein include but are not limited to bacteria, yeast, insect cells, amphibian, and mammalian cells, such as for example, human, primate, rodent, bovine, and ovine cells. In some embodiments, the nucleic acid encoding the mutant PLCγ2 is integrated into the genome of the host cell.

In some embodiments, a method for the expression of a mutant PLCγ2 polypeptide provided herein comprises culturing a host cell containing an expression vector encoding a mutant PLCγ2 polypeptide such that the mutant PLCγ2 polypeptide is produced by the cell. In some methods, the nucleic acid encoding as mutant polypeptide is connected to nucleic acid encoding a signal sequence such that the signal sequence is expressed as a fusion peptide with the mutant PLCγ2 polypeptide. In some embodiments the signal sequence allows for the secretion of the mutant PLCγ2 polypeptide by the host cell.

In some embodiments the mutant PLCγ2 polypeptide is isolated from a host cell expressing the mutant polypeptide. In some embodiments an extract is prepared from the host cell and the mutant PLCγ2 polypeptide is isolated by purification methods such as but not limited to chromatography or immunoaffinity with an antibody that is specific for PLCγ2 polypeptide or specific to the mutant PLCγ2 polypeptide in particular.

Antibodies

Provided herein are isolated antibodies that bind to a modified PLCγ2 polypeptide. In some embodiments, the antibodies do not bind to or bind with lower affinity to a wild-type PLCγ2 polypeptide. In some embodiments, the modified PLCγ2 polypeptide has modifications at amino acid position 742, 845, or 1140.

In some embodiments, mutant PLCγ2 polypeptide provided herein are detected using antibodies that specifically recognize the mutant PLCγ2 polypeptide, but do not recognize wild-type PLCγ2 polypeptide. In some embodiments, mutant PLCγ2 polypeptides provided herein are detected using antibodies that specifically recognize a mutant PLCγ2 polypeptide having a phenylalanine at amino acid position 742, 845, or 1140 but do not recognize the wild-type PLCγ2 polypeptides. In some embodiments, antibodies are raised against one or more allelic forms of the mutant PLCγ2 polypeptide provided herein. Techniques for using a specific protein or an oligopeptide as an antigen to elicit antibodies that specifically recognize epitopes on the peptide or protein are well known. In one embodiment, the DNA sequence of the desired allelic form of the target gene is cloned by insertion into an appropriate expression vector and translated into protein in a prokaryotic or eukaryotic host cell. The protein is recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. In another embodiment, the DNA sequence of the alternative alleles is used as a basis for the generation of synthetic peptides representing the amino acid sequence of the alleles for use as the antigen to elicit the production of specific antibodies.

In some embodiments, antibodies are generated either by standard monoclonal antibody techniques or generated through recombinant based expression systems. See generally, Abbas, Lichtman, and Pober, Cellular and Molecular Immunology, W. B. Saunders Co. (1991). The term "antibodies" is meant to include intact antibody molecules as well as antibody fragments or derivatives, such as Fab and F(ab')2, which are capable of specifically binding to antigen. The antibodies so produced preferentially bind only the mutant protein produced in the allelic form which was used as an antigen to create the antibody. Methods of generating allele-specific antibodies are also described in U.S. Pat. No. 6,200,754 and U.S. Pat. No. 6,054,273, the entire contents of which are incorporated herein by reference.

In some embodiments, the antibody provided herein is a humanized antibody. A "humanized antibody" refers to a type of engineered antibody having its CDRs derived from a non-human donor immunoglobulin, the remaining immunoglobulin-derived parts of the molecule being derived from one or more human immunoglobulin(s). In some embodiments, framework support residues are altered to preserve binding affinity (see, e.g., Queen et al. Proc. Natl. Acad Sci USA, 86:10029-10032 (1989), Hodgson et al. Bio/Technology, 9:421 (1991)). In some embodiments, a suitable human acceptor antibody is one selected from a conventional database, e.g., the KABAT® database, Los Alamos database, and Swiss Protein database, by homology to the nucleotide and amino acid sequences of the donor antibody. In some embodiments, a human antibody characterized by a homology to the framework regions of the donor antibody (on an amino acid basis) is suitable to provide a heavy chain constant region and/or a heavy chain variable framework region for insertion of the donor CDRs. In some embodiments, a suitable acceptor antibody capable of donating light chain constant or variable framework regions is selected in a similar manner. In some embodiments, the acceptor antibody heavy and light chains originate from the same acceptor antibody. In some embodiments, the acceptor antibody heavy and light chains originate from the different acceptor antibodies. The prior art describes several ways of producing such humanized antibodies—see, for example, EP-A-0239400 and EP-A-054951.

In some embodiments, antibodies specific for mutant PLCγ2 polypeptide provided herein are used to detect the presence of a mutant PLCγ2 polypeptide provided herein in a sample, e.g., an assay sample, a cell sample, a cell extract, a biological sample, or a patient sample, using techniques known in the art. These techniques include, for example, Western blot, immunohistochemistry, indirect immunofluorescence, and antibody microarray. In some embodiments, an antibody which specifically recognizes a mutant PLCγ2 polypeptide is an inhibitor of PLCγ2.

EXAMPLES

These examples are provided for illustrative purposes only and not to limit the scope of the claims provided herein.

Example 1: DNA Constructs and Cell Culture

PLCγ2 Mutant Cell Lines

The pRetro-X Tet-On (Clontech, Mountainview, Calif.) or pBABE vectors were used to generate DNA constructs of PLCγ2 that were introduced through retroviral infection. R665W or L845F mutated PLCγ2 was derived by site-directed mutagenesis (QuikChange II, Stratagene-Agilent Technologies, Santa Clara, Calif.). Both constructs have puromycin selection markers. The expression of wild-type or mutant PLCγ2 was controlled by promotors of either CMV in pRetro-X tet-On or SV40 promotor in pBABE vectors. Cells were maintained in RPMI 1640 (Life Technologies, Grand Island, N.Y.) with 2 mM L-glutamine and 10% fetal bovine serum in addition to Penicillin/Streptomycin antibiotics. Stably infected cells were selected and maintained by adding puromycin (1.0 µg/mL) into the cell culture medium.

Primary CLL Cells

For primary CLL cell experiments, peripheral blood mononuclear cells were obtained using Ficoll density gradient centrifugation. B cells were not specifically selected, but at the time of blood acquisition, clinical flow cytometry revealed 85-98% B cells as a percentage of total blood lymphocytes.

Example 2: Methods

DNA Sequencing

Blood was obtained from patients enrolled on Institutional Review Board approved trials of ibrutinib. Tumor DNA was isolated from blood mononuclear cells using AliPrep DNA/RNA Mini kit (Qiagen). Sample preparation and whole-exome sequencing using Agilent SureSelect Human All Exon V4 and Illumina HiSeq2000 technology was performed by Expression Analysis (Durham, N.C.).

Data Analysis Workflow

Copy number analysis of exome-seq data was performed using VarScan 2.3.6 and the BioConductor package DNAcopy. Sequence alignment files of primary and relapse samples were provided to VarScan as pairs. The ratio of uniquely mapped reads were provided to correct potential biases between primary and relapse samples. VarScan generated relapse specific candidate regions with potential copy number alteration. DNAcopy library was used to apply circular binary segmentation (CBS) algorithm to identify unified regions with copy number alterations. This generated a list of chromosomal regions and relapse vs. primary log 2 ratios of coverage. A cutoff of 0.59 was applied on absolute value of log 2 ratios, suggesting at least a copy gain or loss. To identify genes affected by copy number alterations Bedtools intersect function on RefGene annotations was used.

Figure 2:
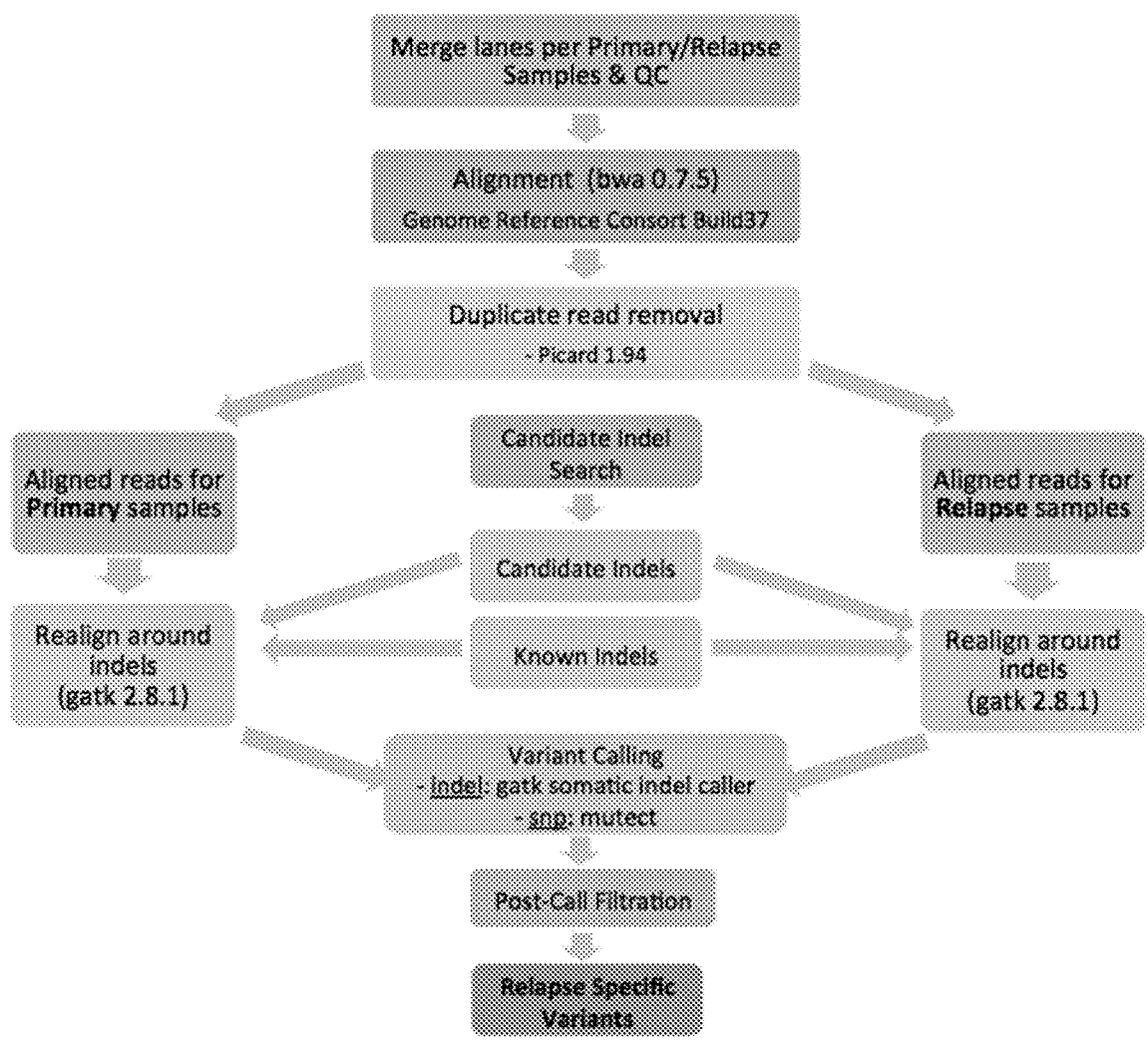
FIG. 2 illustrates exome-seq analysis pipeline flowchart.

FIG. 2 illustrates the exome-seq analysis pipeline flowchart. Sequencing reads were aligned to the human reference genome (1000 Genomes Project human assembly/GRCh37) with BWA (v0.7.5). After potential PCR/optical duplicates were marked with Picard (v1.94, picard.sourceforge.net), local realignment around indels were performed with the Genome Analysis Toolkit (GATK v2.8.1), relapse-specific single point mutations and indels were detected with MuTect (v1.1.4) and GATK Somatic Indel Detector, respectively. After filtering out variants previously reported in dbSNP (build 137), variants were annotated and their potential mutational effects predicted with SnpEff (v3.4,). Finally, newly acquired relapse-specific high quality nonsynonymous mutations were verified by Sanger or Ion Torrent sequencing.

Ion Torrent Analysis

DNA was extracted from cryopreserved cells using QIAmp DNA Mini kit (Qiagen; Hilden, Germany). PLCγ2 gene was analyzed using the Ion Torrent platform from Life Technologies (Carlsbad, Calif.). Library was prepared with Ion AmpliSeq Library kit2.0 (4475345) with custom designed panel of AmpliSeq primers that covers the entire coding sequence and intronic splice acceptor and donor sites for both genes and IonExpress barcode adapters (kit#4471250). DNA was amplified on GeneAmp PCR system 9700 Dual 96-well thermal cycler from Applied Biosystems. PCR product was purified with Agencourt AMPure XP kit (A63881 Beckman Coulter, Indianapolis, Ind.). Library was quantified using real time PCR with Ion Library TAQMAN Quantitation kit 44688022 on (Applied Biosystems ViiA7 Real Time PCR System) instrument to allow for optimal final dilution of library for template preparation on One Touch DL version instrument with Ion One Touch 200Template Kit v2DL (4480285). The ISPs enrichment and purification was performed on One Touch ES using One Touch 200Template Kit v2DL (4480285). Purified ISPs were analyzed on Ion Torrent personal Genome Machine using IonPGM 200 Sequencing kit (4474004) and 316chips (4466616). Data was collected and analyzed using Torrent Server (4462616) with Torrent Suite 3.6.2. Final analysis of sequence data was performed using combination of software: Variant Caller v.3.6.63335, Ion-Torrent IGV3.6.033 and IonReporterUploader v.3.6.2-r62834. The following reference sequence was used for analysis; PLCG2 NM002661.3 (SEQ ID NO: 2). The entire length of sequences was reviewed manually using these programs to asses for deviation from reference sequence and to evaluate the quality of sequence and the depth of coverage.

Phosphoflow and Immunoblot Assays

HEK293T cells were transiently transfected with the indicated expression constructs, treated with ibrutinib for 1 hour, and fixed with paraformaldehyde or washed into fresh media and then fixed. Cells were permeabilized, stained, and analyzed on a BD FACS Canto II.

For immunoblots, whole cell lysates were prepared and equivalent amounts of protein were separated on polyacrylamide gels and transferred onto nitrocellulose membranes. After antibody incubations, proteins were detected with chemiluminescent substrate (SuperSignal; Pierce). Antibodies against phospho-BTK (Tyr223), phospho-AKT (Ser473), AKT, ERK1/2, phospho-PLCγ2(Tyr759; Tyr1217) were obtained from Cell Signaling Technologies (Danvers, Mass.). Phospho-Erk (Thr202/Tyr204) and total PLCγ2 were obtained from Cell Signaling Technologies or Santa Cruz Biotechnology (Santa Cruz, Calif.). Tubulin was obtained from Abcam, and Actin was obtained from Santa Cruz Biotechnologies.

Calcium Flux Assays

DT40 cells stably expressing either wild-type or mutated PLCγ2 were treated with DMSO or 1 µM Ibrutinib at 37° C. for 30 min. The intracellular calcium level was detected by Calcium Assay Kit (BD Biosciences, San Diego, Calif.) and measured by Beckman Coulter DTX880 microplate reader. After 195 seconds of acquisition to determine the baseline, 3 µg/ml anti-chicken IgM (SouthernBiotech, Birmingham, Ala.) was added to stimulate the cells.

Statistical Methods

Linear mixed models with fixed and random effects were used to model all data from different experiments. In experiments designed to determine if autophosphorylation was inhibited in mutated versus wild-type cells and if this inhibition was different under treatment with ibrutinib or dasatinib, interaction contrasts at each concentration of interest were used to directly test the inhibitory hypotheses, including random effects associated with these contrasts. In the experiments testing if the increase in calcium flux over time and following stimulation was different in mutated cell lines treated with ibrutinib or vehicle control, models were fit with treatment and time as fixed effects, allowing for random intercepts and slopes for each condition and replicate. Only data from time points where the effects of stimulation had been observed were included (i.e. time>39 seconds). Statistical significance was declared at $\alpha$=0.05. All analyses were performed using SAS 9.3 (SAS Institute, Cary N.C.).

Example 3: Whole Exome Sequencing Reveals Mutations in BTK and PLCγ2

Figure 3:
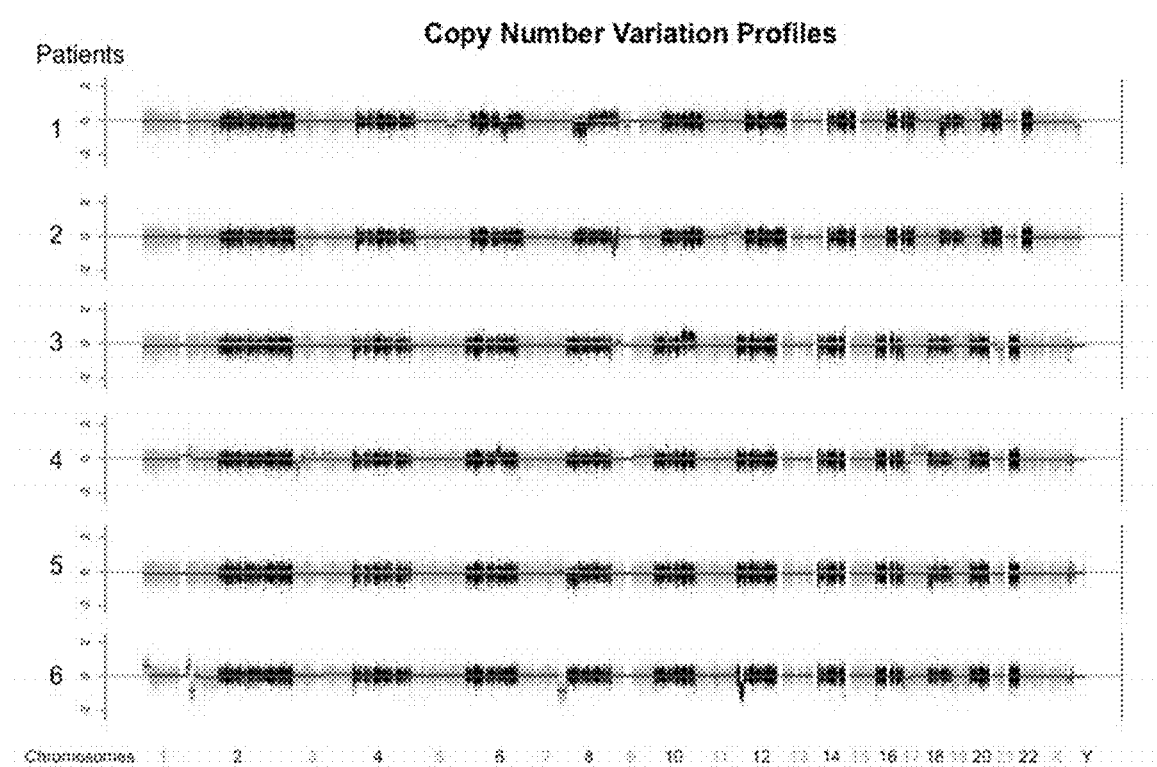
FIG. 3 illustrates copy number profile for all samples. Data were plotted using DNAcopy package of BioConductor.
Figure 4:
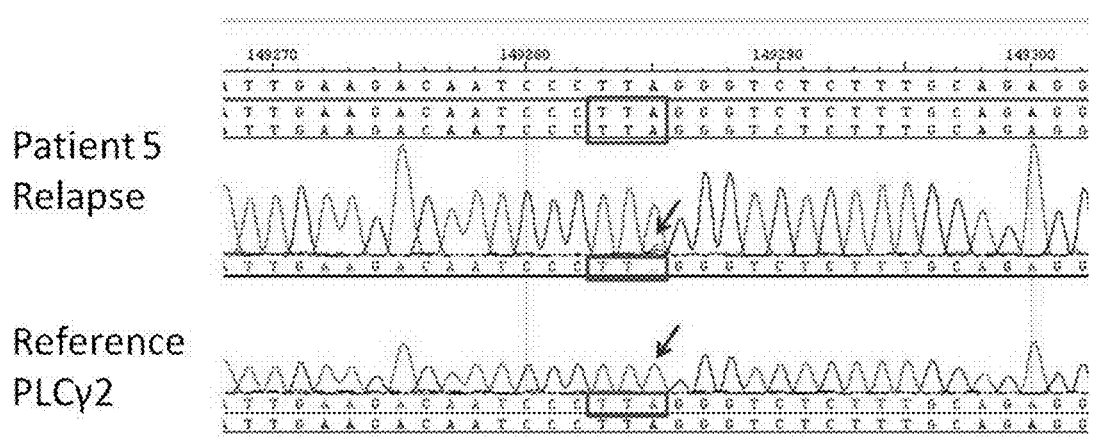
FIG. 4 illustrates partial chromatographs generated by chain-termination DNA sequencing of PLCγ2 from peripheral blood mononuclear cells (PBMC) of patients at relapse. Patient 5 had the A to T mutation in PLCγ2 that results in a Leucine to Phenylalanine substitution. This clone was very small on Sanger sequencing.

Peripheral blood samples were available from patients with progressive CLL at baseline and at the time of relapse. Whole exome sequencing (WES) was performed on each sample. FIG. 1 illustrate the clinical characteristics and new mutations identified at relapse in the patients with matched samples. Table 1 illustrates alignment statistics. On average 99 million reads were generated for each sample. While 98% mapped to the reference genome, on average 78% of them mapped to unique chromosomal positions and used for further analysis. These reads provide approximately 60× coverage of exonic regions. Copy number analysis was performed to ensure identified variants were not result of potential copy number alterations (Table 2, FIG. 3). All patients possess high-risk cytogenetic features including del(11q22.3), del(17p13.1), or complex karyotype. In the tested patient population, the relapse sample revealed distinct PLCγ2 mutations including a leucine to phenylalanine mutation at position 845 (L845F; FIG. 4). In this patient, the PLCγ2 L845F mutation was found by WES. To verify this clone, Ion Torrent sequencing was performed again at a sample 1 month following relapse and the mutation was still present (Table 3). The mutation identified by WES was confirmed by Sanger sequencing and/or Ion Torrent deep sequencing. At baseline, no patient had evidence of mutation in PLCγ2 by WES. In patient 5, Ion Torrent sequencing was performed, and no mutation was >0.5% of reads (Table 4). No other high-confidence recurrent mutation was noted in any of the patients examined from diagnosis to relapse.

Figure 5:
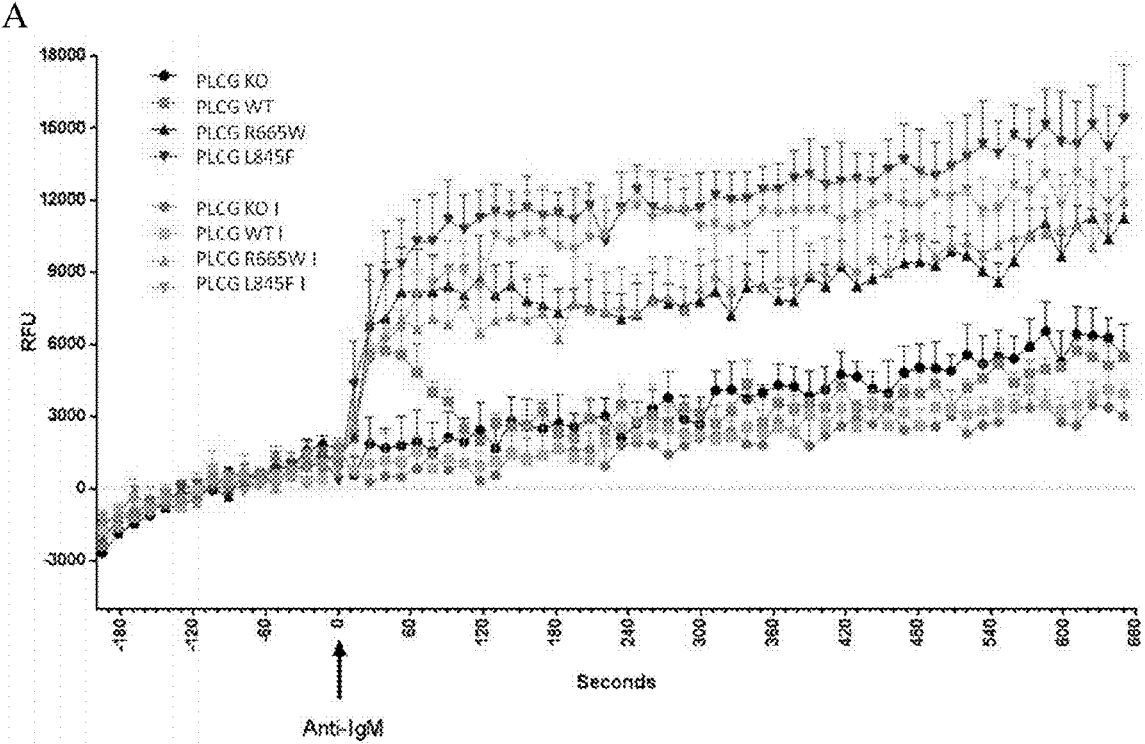
FIG. 5 illustrates functional characterization of the L845F mutation in PLCγ2. pRetro X Tet-on Constructs containing wild-type PLCγ2 or the L845F mutant were transfected or retro-virally delivered into 293 and PLCγ2$^{-/-}$ DT40 cells. After transfection, PLCγ2 was present in these cells, and Y1217 phosphorylation could be detected in 293 cells (FIG. 5A-5C). PLCγ2 DT40 cells stably expressing either wild-type or mutated pRetro-PLCγ2 were treated with vehicle or 1 μM Ibrutinib for 30 minutes followed by stimulation for 15 minutes with 5 μg/ml anti-IgM and then lysed. Immunoblot analysis shows that downstream BCR signaling as evidenced by phosphorylated AKT and ERK are intact in these cells. In cells with the L845F mutation, the repressions of these downstream signals are diminished to a lesser degree by Ibrutinib after anti-IgM stimulation as compared to the wild-type (FIGS. 5A and 5D). All figures are representative and are reflective of at least 3 independent experiments.
Figure 5:
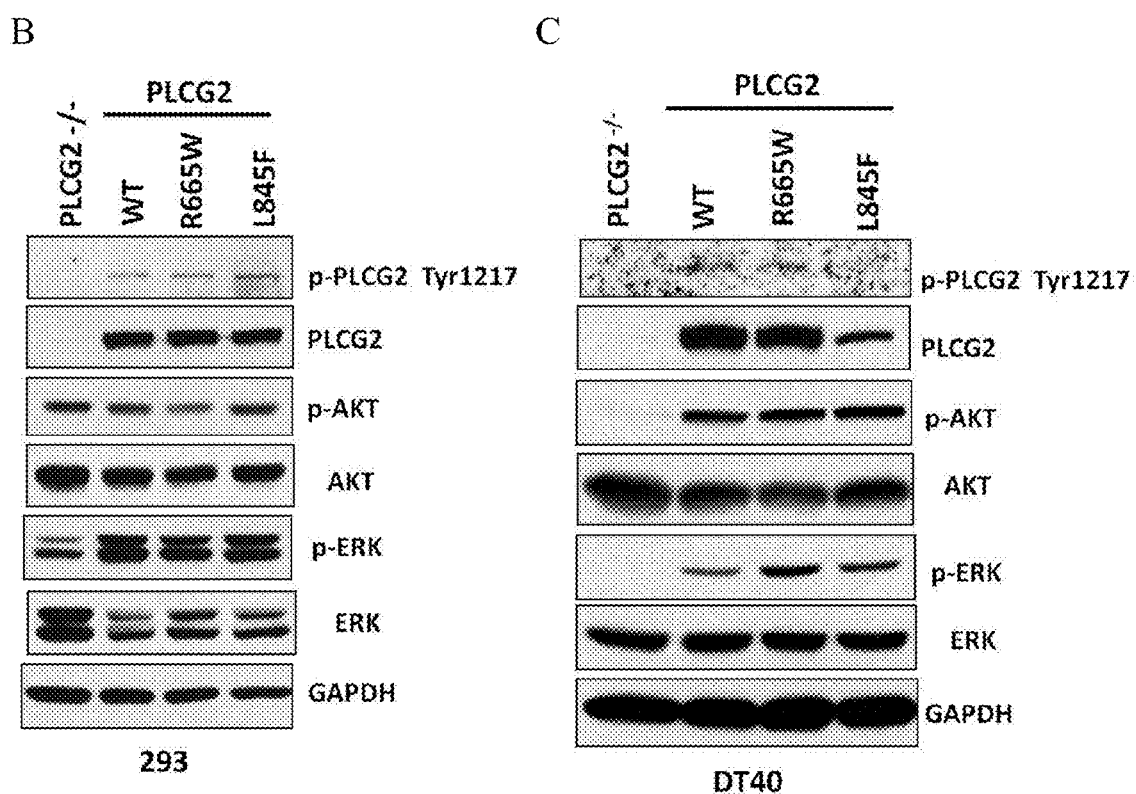
Figure 5:
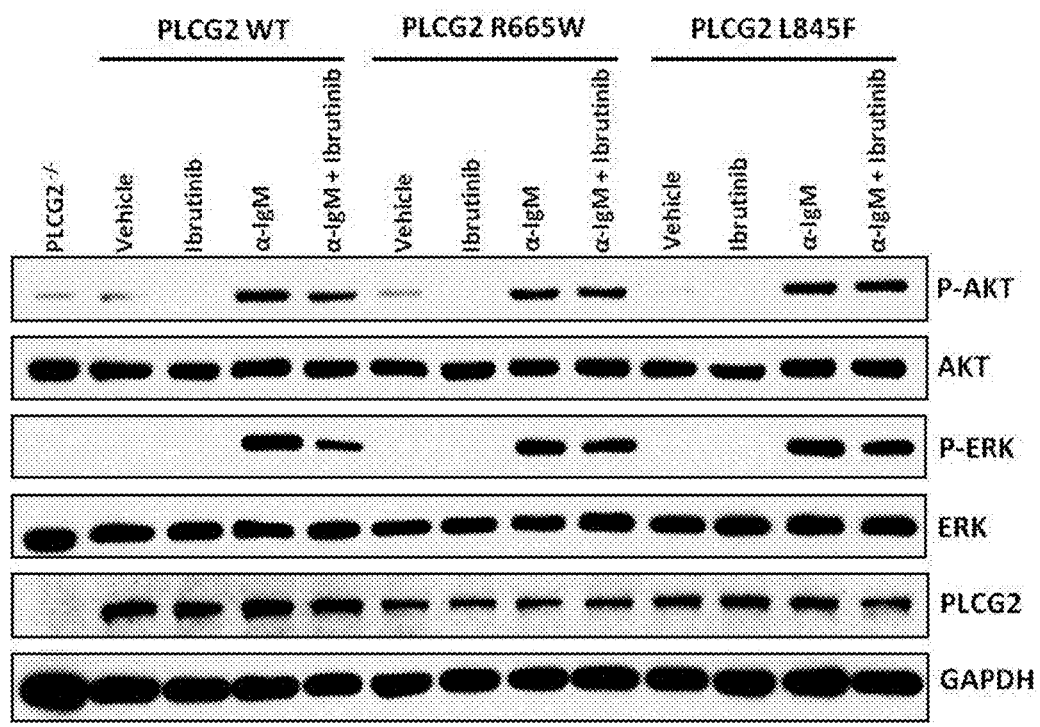

Example 4: Identified Mutations of PLCγ2 are Potentially Gain of Function in the Presence of BCR Stimulation and Represent Resistance Mechanisms in Patients WT PLCγ2 and L845F PLCγ2 were stably transfected into 293 cells and DT40 cells which lack endogenous PLCγ2 expression (FIG. 5). Calcium flux was examined in DT40 cells after anti-IgM stimulation in the presence of WT or mutant PLCγ2. The PLCγ2 mutant showed enhanced IgM-mediated calcium flux that was not inhibited by ibrutinib (FIG. 5A). This showed that the mutation allowed for BCR-mediated signaling which was independent of BTK. Similarly, after stimulation with anti-IgM, cells with L845F mutation showed less inhibition in the presence of ibrutinib than WT cells as measured by phosphorylation of ERK and AKT (FIG. 5B-5D). These data demonstrated that L845F PLCγ2 is potentially a gain of function mutation in the presence of BCR stimulation and could be relevant resistance mutations to ibrutinib in patients. An additional mutation in PLCγ2 was also tested and was shown to be another potential gain of function mutation in the presence of BCR stimulation.

Figure 6:
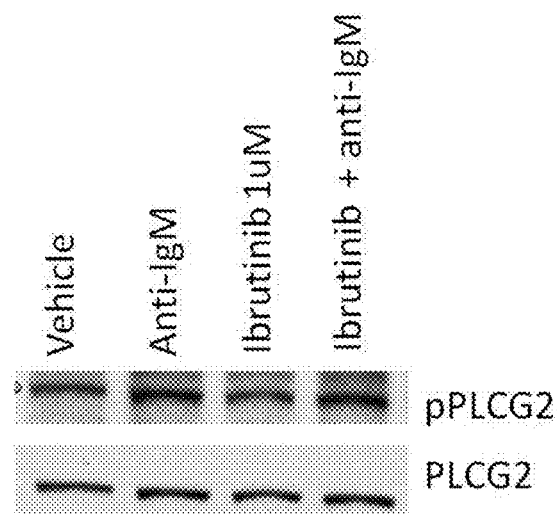
FIG. 6 illustrates PLCγ2 analysis by immunoblot at relapse. At the time of relapse after drug had been discontinued, fresh cells were treated with vehicle, plate-immobilized anti-IgM, 1 μM ibrutinib, or ibrutinib+anti-IgM. Phosphorylation of PLCγ2 (FIG. 6A) and ERK (FIG. 6B) are not inhibited by ibrutinib. Samples were obtained from patient 5.
Figure 6:
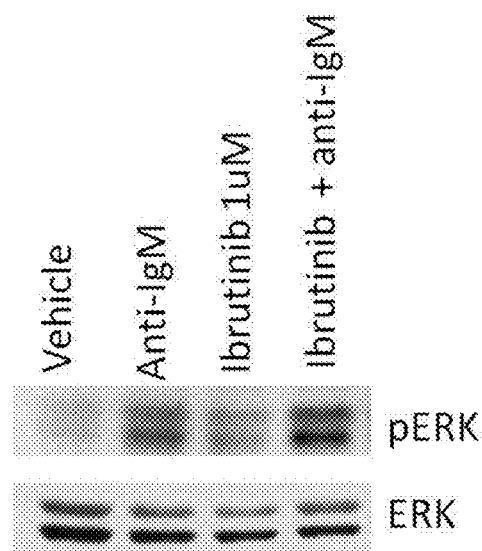

CLL cells were examined at baseline and at the time of relapse from patients #5. In patient 5 who possessed a L845F mutation in PLCγ2, in vitro ibrutinib did not inhibit PLCγ2 phosphorylation (FIG. 6). These data suggest that the gain of function phenotype seen in vitro is also relevant in patients.

Example 5: Patients with Prolonged Lymphocytosis on Ibrutinib do not have PLCγ2 Mutation Patients treated with ibrutinib develop a characteristic lymphocytosis as CLL cells are mobilized from lymph nodes and spleen. While most patients resolve their lymphocytosis within 8 months, a subset of patients have lymphocytosis that lasts >12 months in the presence of continued response to ibrutinib. To determine whether these patients developed new mutations in PLCγ2 and may therefore be at risk for relapse, the PLCγ2 gene was sequenced using Ion Torrent technology on 9 patients with at least 12 months of lymphocytosis at 12 months after the initiation of ibrutinib. Sequencing depth for PLCγ2 at L845 was >100×. No patient had evidence of any mutation of PLCγ2. This suggests that known resistance mutations are not present in patients with persistent lymphocytosis.

TABLE 1

Alignment Statistics

| Patient | State | # Reads | # Mapped Reads | Mapped % | # Duplicate Reads | # Uniquely Mapped Reads | Uniquely Mapped % | Exome Coverage X |
|---|---|---|---|---|---|---|---|---|
| 1 | primary | 79,983,792 | 79,473,899 | 0.99 | 14,216,155 | 65,257,744 | 0.82 | 59.4 |
| 1 | relapse | 92,261,016 | 91,723,753 | 0.99 | 15,369,175 | 76,354,578 | 0.83 | 69.7 |
| 2 | primary | 83,615,748 | 83,013,800 | 0.99 | 13,503,169 | 69,510,631 | 0.83 | 63.0 |
| 2 | relapse | 82,729,482 | 82,256,076 | 0.99 | 15,685,173 | 66,570,903 | 0.80 | 59.5 |
| 3 | primary | 103,691,442 | 102,676,127 | 0.99 | 48,551,111 | 54,125,016 | 0.52 | 52.0 |
| 3 | relapse | 85,019,380 | 84,190,701 | 0.99 | 15,568,341 | 68,622,360 | 0.81 | 62.6 |
| 4 | primary | 100,604,310 | 99,982,483 | 0.99 | 29,263,406 | 70,719,077 | 0.70 | 67.0 |
| 4 | relapse | 103,968,204 | 103,334,312 | 0.99 | 27,245,541 | 76,088,771 | 0.73 | 71.5 |
| 5 | primary | 149,140,122 | 138,197,068 | 0.93 | 15,773,113 | 122,423,955 | 0.82 | 43.0 |
| 5 | relapse | 133,058,006 | 121,507,870 | 0.91 | 14,330,393 | 107,177,477 | 0.81 | 36.5 |
| 6 | primary | 90,076,314 | 89,600,955 | 0.99 | 21,305,687 | 68,295,268 | 0.76 | 61.0 |
| 6 | relapse | 85,427,322 | 85,034,356 | 1.00 | 10,225,110 | 74,809,246 | 0.88 | 68.3 |
| Average | | 99,131,262 | 96,749,283 | 0.98 | 20,086,365 | 76,662,919 | 0.78 | 59.5 |

TABLE 2

Copy number analysis and genes affected by copy number alterations.

| Patient | Chr | Start | End | Width | Log 2 ratio (relapse vs primary) | Genes |
|---|---|---|---|---|---|---|
| 2 | 3 | 20136589 | 24398068 | 4261479 | −0.5996 | KAT2B, LOC152024, NKIRAS1, NR1D2, RPL15, SGOL1, THRB, UBE2E1, UBE2E2, VENTXP7, ZNF385D |
| 2 | 8 | 133918901 | 135651823 | 1732922 | −0.6082 | NDRG1, SLA, ST3GAL1, TG, WISP1, ZFAT, ZFATAS |
| 2 | 8 | 127569519 | 133905776 | 6336257 | −0.6033 | ADCY8, ASAP1, ASAP1IT, EFR3A, FAM49B, FAM84B, GSDMC, HHLA1, HPYR1, KCNQ3, LOC727677, LOC728724, LRRC6, MIR1204, MIR1205, MIR1206, MIR1207, MIR1208, MYC, OC90, PHF20L1, POU5F1B, PVT1, TG, TMEM71 |
| 3 | 8 | 141930840 | 142138799 | 207959 | −0.8497 | DENND3, PTK2 |
| 3 | Y | 8493559 | 9097882 | 604323 | −0.9623 | TTTY11, TTTY18, TTTY19 |
| 4 | 7 | 5364714 | 5364847 | 133 | −1.2545 | TNRC18 |
| 4 | 14 | 74766221 | 74769554 | 3333 | −1.0545 | ABCD4 |
| 6 | 1 | 161640950 | 170916399 | 9275449 | −0.821 | ADCY10, ALDH9A1, ANKRD36BP1, ATF6, ATP1B1, BLZF1, BRP44, C1orf110, C1orf111, C1orf112, C1orf114, C1orf129, C1orf156, C1orf226, CD247, CREG1, DCAF6, DDR2, DPT, DUSP12, DUSP27, F5, FAM78B, FCGR2B, FCRLA, FCRLB, FMO9P, GORAB, GPA33, GPR161, HSD17B7, ILDR2, KIFAP3, LMX1A, LOC284688, LOC400794, LOC440700, LRRC52, MAEL, METTL11B, MGC4473, MGST3, MIR3119-1, MIR3119-2, MIR556, MIR557, MIR921, MPZL1, NME7, NOS1AP, NUF2, OLFML2B, PBX1, POGK, POU2F1, PRRX1, RCSD1, RGS4, RGS5, RPL31P11, RXRG, SCYL3, SELE, SELL, SELP, SFT2D2, SH2D1B, SLC19A2, TADA1, TBX19, TIPRL, TMCO1, UAP1, UCK2, UHMK1, XCL1, XCL2 |
| 6 | 1 | 161559078 | 161600706 | 41628 | −1.267 | FCGR2C, FCGR3B, HSPA7 |
| 6 | 1 | 156721019 | 161519393 | 4798374 | −0.8325 | ADAMTS4, AIM2, APCS, APOA2, ARHGAP30, ARHGEF11, ATP1A2, ATP1A4, B4GALT3, C1orf192, C1orf204, C1orf92, CADM3, CASQ1, CCDC19, CD1A, CD1B, CD1C, CD1D, CD1E, CD244, CD48, CD5L, CD84, COPA, CRP, CYCSP52, DARC, DCAF8, DEDD, DUSP23, ETV3, ETV3L, F11R, FCER1A, FCER1G, FCGR2A, FCGR3A, FCRL1, FCRL2, FCRL3, FCRL4, FCRL5, FCRL6, HDGF, HSPA6, IFI16, IGSF8, IGSF9, INSRR, ITLN1, ITLN2, KCNJ10, KCNJ9, KIRREL, KLHDC9, LOC646268, LY9, MIR765, MNDA, MPZ, NCSTN, NDUFS2, NHLH1, NIT1, NR1I3, NTRK1, OR10J1, OR10J3, OR10J5, OR10K1, OR10K2, OR10R2, OR10T2, OR10X1, OR10Z1, OR6K2, OR6K3, OR6K6, OR6N1, OR6N2, OR6P1, OR6Y1, PCP4L1, PEA15, PEAR1, PEX19, PFDN2, PIGM, PPOX, PRCC, PVRL4, PYHIN1, SDHC, SH2D2A, SLAMF1, SLAMF6, SLAMF7, SLAMF8, SLAMF9, SPTA1, SUMO1P3, TAGLN2, TOMM40L, TSTD1, UFC1, USF1, USP21, VANGL2, VSIG8 |
| 6 | 1 | 156646068 | 156714751 | 68683 | 0.6946 | C1orf66, CRABP2, HDGF, ISG20L2, MRPL24, NES |
| 6 | 1 | 156506937 | 156644828 | 137891 | 0.9182 | APOA1BP, BCAN, GPATCH4, HAPLN2, IQGAP3, NES, TTC24 |
| 6 | 1 | 145301664 | 146737497 | 1435833 | 0.5901 | ANKRD34A, ANKRD35, CD160, CHD1L, FMO5, GNRHR2, GPR89A, GPR89C_dup1, HFE2, ITGA10, LIX1L, LOC728989, NBPF10, NBPF11_dup1, NBPF24_dup1, NUDT17, PDIA3P, PDZK1, PDZK1P1_dup1, PEX11B, PIAS3, POLR3C, POLR3GL, PRKAB2, RBM8A, RNF115, TXNIP |
| 6 | 7 | 141794234 | 159025990 | 17231756 | −0.8421 | ABCB8, ABCF2, ABP1, ACCN3, ACTR3B, ACTR3C, AGAP3, ARHGEF35, ARHGEF5, ASB10, ATG9B, ATP6VOE2, C7orf13, C7orf29, C7orf33, C7orf34, CASP2, CDK5, CHPF2, CLCN1, CNPY1, CNTNAP2, CRYGN, CTAGE15P, CTAGE4_dup1, CTAGE4_dup2, CTAGE6P, CUL1, DNAJB6, DPP6, EN2, |

TABLE 2-continued

Copy number analysis and genes affected by copy number alterations.

| Patient | Chr | Start | End | Width | Log 2 ratio (relapse vs primary) | Genes |
|---|---|---|---|---|---|---|
| | | | | | | EPHA1, EPHB6, ESYT2, EZH2, FABP5P3, FAM115A, FAM115C, FAM131B, FASTK, GALNT11, GALNTL5, GBX1, GIMAP1, GIMAP2, GIMAP4, GIMAP5, GIMAP6, GIMAP7, GIMAP8, GSTK1, HTR5A, INSIG1, KCNH2, KEL, KRBA1, LMBR1, LOC100124692, LOC100128542, LOC100128822, LOC100131176, LOC100132707, LOC154761, LOC154822, LOC155060, LOC202781, LOC285965, LOC285972, LOC401431, LOC728377, LOC728743, LOC730441, LOC93432, LRRC61, MGAM, MIR153-2, MIR548F3, MIR548F4, MIR548I4, MIR548T, MIR595, MIR671, MLL3, MNX1, MOXD2P, MTRNR2L6, NCAPG2, NCRNA00244, NOBOX, NOM1, NOS3, NUB1, OR2A12, OR2A14, OR2A1_dup1, OR2A1_dup2, OR2A2, OR2A20P_dup1, OR2A20P_dup2, OR2A25, OR2A42_dup1, OR2A42_dup2, OR2A5, OR2A7, OR2A9P_dup1, OR2A9P_dup2, OR2F1, OR2F2, OR6B1, OR6V1, OR6W1P, OR9A2, PAXIP1, PDIA4, PIP, PRKAG2, PRSS1, PRSS2, PTPRN2, RARRES2, RBM33, REPIN1, RHEB, RNF32, SHH, SLC4A2, SMARCD3, SSPO, TAS2R39, TAS2R40, TAS2R41, TAS2R60, TMEM139, TMEM176A, TMEM176B, TMUB1, TPK1, TRPV5, TRPV6, TRY6, TRYX3, UBE3C, VIPR2, WDR60, WDR86, XRCC2, ZNF212, ZNF282, ZNF398, ZNF425, ZNF467, ZNF746, ZNF767, ZNF775, ZNF777, ZNF783, ZNF786, ZNF862, ZYX |
| 6 | 7 | 130562110 | 141764144 | 11202034 | −0.8339 | ADCK2, AGBL3, AGK, AKR1B1, AKR1B10, AKR1B15, AKR1D1, ATP6V0A4, BPGM, BRAF, C7orf49, C7orf55, CALD1, CHCHD3, CHRM2, CLEC2L, CLEC5A, CNOT4, CREB3L2, DENND2A, DGKI, EXOC4, FAM180A, FLJ40852, FLJ43663, HIPK2, JHDM1D, KIAA1147, KIAA1549, KLRG2, LOC100129148, LOC100131199, LOC100134229, LOC100134713, LOC646329, LRGUK, LUC7L2, LUZP6, MGAM, MIR29B1, MIR490, MKLN1, MKRN1, MRPS33, MTPN, NDUFB2, NUP205, OR9A4, PARP12, PL-5283, PLXNA4, PODXL, PRSS37, PTN, RAB19, SLC13A4, SLC35B4, SLC37A3, SSBP1, STRA8, SVOPL, TAS2R3, TAS2R38, TAS2R4, TAS2R5, TBXAS1, TMEM140, TMEM213, TRIM24, TTC26, UBN2, WDR91, WEE2, ZC3HAV1, ZC3HAV1L |
| 6 | 12 | 10370520 | 23893778 | 13523258 | −0.8412 | ABCC9, AEBP2, APOLD1, ARHGDIB, ART4, ATF7IP, BCL2L14, C12orf36, C12orf39, C12orf60, C12orf69, CAPZA3, CDKN1B, CMAS, CREBL2, CSDA, DDX47, DERA, DUSP16, EMP1, EPS8, ERP27, ETNK1, ETV6, GABARAPL1, GOLT1B, GPR19, GPRC5A, GPRC5D, GRIN2B, GSG1, GUCY2C, GYS2, H2AFJ, HEBP1, HIST4H4, HTR7P1, IAPP, KCNJ8, KIAA0528, KIAA1467, KLRA1, KLRC1, KLRC2, KLRC3, KLRC4, KLRD1, KLRK1, LDHB, LMO3, LOC100129361, LOC338817, LOC728622, LOH12CR1, LOH12CR2, LRP6, LST-3TM12, MAGOHB, MANSC1, MGP, MGST1, MIR1244-1_dup2, MIR1244-2_dup2, MIR1244-3_dup2, MIR613, MIR614, |

TABLE 2-continued

Copy number analysis and genes affected by copy number alterations.

| Patient | Chr | Start | End | Width | Log 2 ratio (relapse vs primary) | Genes |
|---------|-----|-------|-----|-------|-----------------------------------|-------|
| 6 | 14 | 106922029 | 107034811 | 112782 | −1.1707 | PDE3A, PDE6H, PIK3C2G, PLBD1, PLCZ1, PLEKHA5, PRB1, PRB2, PRB3, PRB4, PRH1, PRH2, PRR4, PTPRO, PYROXD1, RECQL, RERG, RERGL, RPL13AP20, SLC15A5, SLCO1A2, SLCO1B1, SLCO1B3, SLCO1C1, SOX5, ST8SIA1, STRAP, STYK1, TAS2R10, TAS2R13, TAS2R14, TAS2R19, TAS2R20, TAS2R30, TAS2R31, TAS2R42, TAS2R43, TAS2R46, TAS2R50, TAS2R7, TAS2R8, TAS2R9, WBP11 NCRNA00221 |

TABLE 3

Patient 5 Ion Torrent sequencing at relapse and 1 month post-relapse

| | | Relapse | | 1 month post-relapse | |
|---|---|---|---|---|---|
| Chromosome | Gene | AA change | Coverage | Variant Frequency | Coverage | Variant Frequency |
| 16 | PLCγ2 | R665W | 278 | 5.4% | 614 | 3.7% |
| 16 | PLCγ2 | S707Y | 1570 | 8% | 1287 | 6.8% |
| 16 | PLCγ2 | L845F | 579 | 17.4% | 806 | 23.8% |
| X | BTK | C481S | 992 | 2.6% | 1011 | 3.5% |

TABLE 4

Baseline data for patients deep sequenced with Ion Torrent

| ID | Chrom | Position | Gene | AAchange | Reference | Variant | Coverage | Variant Frequency |
|----|-------|----------|------|----------|-----------|---------|----------|-------------------|
| 3 | X | 100611164 | BTK | C481S | C | G | 693 | 0 |
| 5 | 16 | 81946260 | PLCγ2 | R665W | C | T | 928 | 0.1% |
| 5 | 16 | 81953154 | PLCγ2 | S707Y | C | A | 2839 | 0 |
| 5 | 16 | 81962183 | PLCγ2 | L845F | A | T | 207 | 0 |
| 5 | X | 100611164 | BTK | C481S | C | G | 875 | 0 |
| 6 | 16 | 81946260 | PLCγ2 | R665W | C | T | 1758 | 0.2% |

Example 6: Acquisition of Resistance Mutations Associated with Disease Progression on Ibrutinib Therapy: Single Center Study 267 patients from The Ohio State University Comprehensive Cancer Center participating in 3 Institutional Review Board approved trials of ibrutinib were included; 196 patients received single agent ibrutinib and 71 received ibrutinib plus ofatumumab. A subset of patients with PD had Ion Torrent deep sequencing performed on peripheral blood at baseline and relapse.

Fine and Gray models of cumulative incidence were fit to identify variables associated with a particular type of discontinuation and in the presence of competing risks. Patients who had not discontinued study were censored at date of last contact; patients who went off study for transplant or to continue treatment elsewhere (n=7) were also censored at that time. Final models included variables significant at p<0.05 using forward selection or variables of borderline significance that were deemed clinically meaningful, while controlling for type of therapy.

The treatment regimens of the patient groups were as follows:

1. OSU 10032 (PCYC 1102) N=50

Ibrutinib 420 mg or 840 mg daily until disease progression

2. OSU 10053 (PCYC 1109) N=71

Cohort 1: Ibrutinib 420 mg daily starting C1D1 until disease progression; Ofatumumab start C2D1 weekly×8 weeks, then monthly×4 months Cohort 2: Ibrutinib 420 mg daily starting C1D2 until disease progression; Ofatumumab start C1D1 weekly×8 weeks, then monthly×4 months Cohort 3: Ofatumumab start C1D1 weekly×8 weeks, then monthly×4 months. Ibrutinib start C3D1 daily until disease progression.

3. OSU 11133 N=146

Ibrutinib 420 mg daily until disease progression

Results

Figure 7:
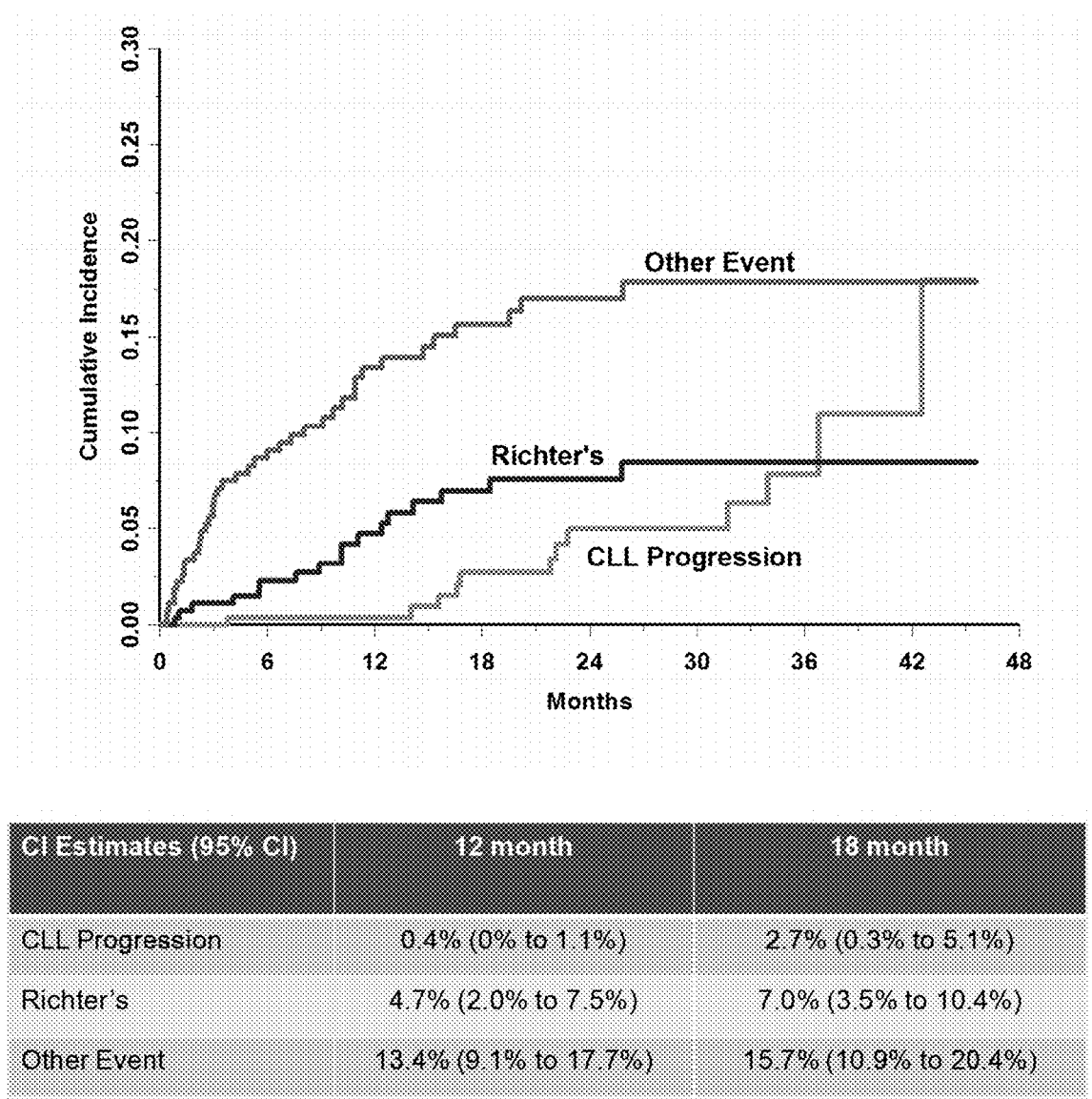
FIG. 7 illustrates the cumulative incidence of CLL progression, Richter's transformation, or other events among patients with progressive disease during the course of ibrutinib therapy.

At median follow-up of 20.2 months (range 2.6-46 months), factors related to discontinuation on the study included progressive disease (n=29), infection (n=25), toxicity (n=8), or other complications (n=7) or receipt of therapy elsewhere (n=7). FIG. 7 summarizes the cumulative incidence of CLL progression, Richter's transformation, or other event among patients with progressive disease. FIG. 8 summarizes baseline characteristics associated with study discontinuation among patients with progressive disease (e.g., CLL, Richter's) or discontinuations for a non-progressive disease reason (e.g., infection, toxicity or other). Both models were adjusted for type of therapy: combination versus monotherapy with Ibrutinib. FIG. 9 illustrates the identification of BTK and PLCγ2 mutations in patients that experienced relapse on the Ibrutinib therapy.

For the patients that were characterized as having Richter's Transformation, 5 patients received no additional therapy and died within 1 month of transformation and 10 patients with DLBCL received additional therapy: R-EP-OCH (N=5) 4 PD, 1 PR, R-CHOP (N=1) PD, R-ICE (N=1) PD, OFAR (N=1) PD. Over the course of the study to date 14 of 17 patients with Richter's Transformation have died. The Median Survival from date off ibrutinib study was 120 days.

For the patients that were characterized as having CLL progression, 2 patients received no additional therapy and 10 patients received further therapy <2 months post-PD, most within 2 weeks. Over the course of the study to date 4 of 12 patients having CLL progression have died. The Median Survival from date off ibrutinib study was 535 days.

From this study it was concluded that Ibrutinib was a well tolerated and effective therapy, and discontinuation was uncommon with the study length of follow up. Disease progression on ibrutinib was associated with karyotypic complexity and BCL6 on FISH. Richter's transformation was more common than progressive CLL and tended to occur earlier in therapy. Progressive CLL was commonly associated with mutations in BTK and PLCγ. Both Richter's and progressive CLL tended to progress rapidly, especially after discontinuation of ibrutinib.

The examples and embodiments described herein are for illustrative purposes only and various modifications or changes suggested to persons skilled in the art are to be included within the spirit and purview of this application and scope of the appended claims.

What is claimed is:

1. A method of maintenance therapy in a subject having a hematologic cancer, wherein the subject does not have a modification in PLCγ2 polypeptide at an amino acid position corresponding to amino acid position 845 of the amino acid sequence set forth in SEQ ID NO: 2, comprising:
   a. administering to the subject a maintenance therapy regimen comprising administering a therapeutically effective dose of a BTK inhibitor; and
   b. monitoring the subject at predetermined intervals of time over the course of the maintenance therapy regimen to determine whether the subject acquires a mutation in an endogenous gene encoding PLCγ2 that results in a modification at an amino acid position corresponding to amino acid position 845 of the amino acid sequence set forth in SEQ ID NO: 2; and
   c. discontinuing treatment with the BTK inhibitor if the subject acquires the mutation.

2. The method of claim 1, wherein the mutation is a mutation of adenine to thymidine at nucleic acid position corresponding to nucleic acid position 2713 in the sequence of nucleotides set forth in SEQ ID NO: 1.

3. The method of claim 1, wherein the mutation encodes a substitution of leucine to an amino acid selected from cysteine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 845 of the PLCγ2 polypeptide.

4. The method of claim 3, wherein the mutation is a L845F modification in the PLCγ2 polypeptide.

5. The method of claim 1, wherein the subject possesses high-risk cytogenetic features.

6. The method of claim 5, wherein the high-risk cytogenetic features comprise del(11q22.3), del(17p13.1) or complex karyotype.

7. The method of claim 1, wherein the hematologic cancer is a B-cell malignancy.

8. The method of claim 7, wherein the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

9. The method of claim 8, wherein the cancer is a B-cell malignancy selected from the group consisting of mantle cell lymphoma (MCL), chronic lymphocytic leukemia (CLL), Waldenström macroglobulinemia (WM), small lymphocytic lymphoma (SLL), follicular lymphoma (FL), diffuse large B-cell lymphoma (DLBCL), and marginal zone lymphoma (MZL).

10. The method of claim 1, wherein the BTK inhibitor is ibrutinib.

11. The method of claim 10, wherein the mutation is a mutation of adenine to thymidine at nucleic acid position corresponding to nucleic acid position 2713 in the sequence of nucleotides set forth in SEQ ID NO: 1.

12. The method of claim 10, wherein the mutation encodes a substitution of leucine to an amino acid selected from cysteine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 845 of the PLCγ2 polypeptide.

13. The method of claim 12, wherein mutation is a L845F modification in the PLCγ2 polypeptide.

14. The method of claim 10, wherein the subject possesses high-risk cytogenetic features.

15. The method of claim 14, wherein the high-risk cytogenetic features comprise del(11q22.3), del(17p13.1) or complex karyotype.

16. The method of claim 10, wherein the hematologic cancer is a B-cell malignancy.

17. The method of claim 16, wherein the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

18. The method of claim 17, wherein the cancer is a B-cell malignancy selected from the group consisting of mantle cell lymphoma (MCL), chronic lymphocytic leukemia (CLL), Waldenström macroglobulinemia (WM), small lymphocytic lymphoma (SLL), follicular lymphoma (FL), diffuse large B-cell lymphoma (DLBCL), and marginal zone lymphoma (MZL).

19. A system of detecting a modified PLCγ2 that confers resistance to inhibition with an irreversible BTK inhibitor in a subject, comprising:
 a. a sample containing a nucleic acid molecule encoding a PLCγ2 polypeptide from the subject; and
 b. a microarray comprising nucleic acid encoding a modified PLCγ2 polypeptide or a portion thereof that is modified at an amino acid position corresponding to amino acid position 845 of the amino acid sequence set forth in SEQ ID NO: 2.

20. The system of claim 19, wherein the microarray further comprises nucleic acid encoding a modified PLCγ2 polypeptide or a portion thereof that is modified at additional amino acid positions.

21. A method of maintenance therapy in a subject having a hematologic cancer, wherein the subject does not have a modification in PLCγ2 polypeptide at an amino acid position corresponding to amino acid position 742 of the amino acid sequence set forth in SEQ ID NO: 2, comprising:
 a. administering to the subject a maintenance therapy regimen comprising administering a therapeutically effective dose of a BTK inhibitor; and
 b. monitoring the subject at predetermined intervals of time over the course of the maintenance therapy regimen to determine whether the subject acquires a mutation in an endogenous gene encoding PLCγ2 that results in a modification at an amino acid position corresponding to amino acid position 742 of the amino acid sequence set forth in SEQ ID NO: 2; and
 c. discontinuing treatment with the BTK inhibitor if the subject acquires the mutation.

22. The method of claim 21, wherein the mutation encodes a substitution of asparagine to an amino acid selected from leucine, cysteine, isoleucine, valine, alanine, glycine, methionine, serine, threonine, phenylalanine, tryptophan, lysine, arginine, histidine, proline, tyrosine, glutamine, aspartic acid and glutamic acid at amino acid position 742 of the PLCγ2 polypeptide.

23. The method of claim 22, wherein the mutation is a R742P modification in the PLCγ2 polypeptide.

24. The method of claim 21, wherein the subject possesses high-risk cytogenetic features.

25. The method of claim 24, wherein the high-risk cytogenetic features comprise del(11q22.3), del(17p13.1) or complex karyotype.

26. The method of claim 21, wherein the hematologic cancer is a B-cell malignancy.

27. The method of claim 26, wherein the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

28. The method of claim 27, wherein the cancer is a B-cell malignancy selected from the group consisting of mantle cell lymphoma (MCL), chronic lymphocytic leukemia (CLL), Waldenström macroglobulinemia (WM), small lymphocytic lymphoma (SLL), follicular lymphoma (FL), diffuse large B-cell lymphoma (DLBCL), and marginal zone lymphoma (MZL).

29. The method of claim 21, wherein the BTK inhibitor is ibrutinib.

30. The method of claim 29, wherein the mutation encodes a substitution of asparagine to an amino acid selected from leucine, cysteine, isoleucine, valine, alanine, glycine, methionine, serine, threonine, phenylalanine, tryptophan, lysine, arginine, histidine, proline, tyrosine, glutamine, aspartic acid and glutamic acid at amino acid position 742 of the PLCγ2 polypeptide.

31. The method of claim 30, wherein the mutation is a R742P modification in the PLCγ2 polypeptide.

32. The method of claim 29, wherein the subject possesses high-risk cytogenetic features.

33. The method of claim 32, wherein the high-risk cytogenetic features comprise del(11q22.3), del(17p13.1) or complex karyotype.

34. The method of claim 29, wherein the hematologic cancer is a B-cell malignancy.

35. The method of claim 34, wherein the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

36. The method of claim 35, wherein the cancer is a B-cell malignancy selected from the group consisting of mantle cell lymphoma (MCL), chronic lymphocytic leukemia (CLL), Waldenström macroglobulinemia (WM), small lymphocytic lymphoma (SLL), follicular lymphoma (FL), diffuse large B-cell lymphoma (DLBCL), and marginal zone lymphoma (MZL).

37. A system of detecting a modified PLCγ2 that confers resistance to inhibition with an irreversible BTK inhibitor in a subject, comprising:
   a. a sample containing a nucleic acid molecule encoding a PLCγ2 polypeptide from the subject; and
   b. a microarray comprising nucleic acid encoding a modified PLCγ2 polypeptide or a portion thereof that is modified at an amino acid position corresponding to amino acid position 742 of the amino acid sequence set forth in SEQ ID NO: 2.

38. The system of claim 37, wherein the microarray further comprises nucleic acid encoding a modified PLCγ2 polypeptide or a portion thereof that is modified at additional amino acid positions.

39. A method of maintenance therapy in a subject having a hematologic cancer, wherein the subject does not have a modification in PLCγ2 polypeptide at an amino acid position corresponding to amino acid position 1140 of the amino acid sequence set forth in SEQ ID NO: 2, comprising:
   a. administering to the subject a maintenance therapy regimen comprising administering a therapeutically effective dose of a BTK inhibitor; and
   b. monitoring the subject at predetermined intervals of time over the course of the maintenance therapy regimen to determine whether the subject acquires a mutation in an endogenous gene encoding PLCγ2 that results in a modification at an amino acid position corresponding to amino acid position 1140 of the amino acid sequence set forth in SEQ ID NO: 2; and
   c. discontinuing treatment with the BTK inhibitor if the subject acquires the mutation.

40. The method of claim 39, wherein the mutation encodes a substitution of aspartic acid to an amino acid selected from leucine, cysteine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 1140 of the PLCγ2 polypeptide.

41. The method of claim 40, wherein the mutation is a D1140G modification in the PLCγ2 polypeptide.

42. The method of claim 39, wherein the subject possesses high-risk cytogenetic features.

43. The method of claim 42, wherein the high-risk cytogenetic features comprise del(11q22.3), del(17p13.1) or complex karyotype.

44. The method of claim 39, wherein the hematologic cancer is a B-cell malignancy.

45. The method of claim 44, wherein the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

46. The method of claim 45, wherein the cancer is a B-cell malignancy selected from the group consisting of mantle cell lymphoma (MCL), chronic lymphocytic leukemia (CLL), Waldenström macroglobulinemia (WM), small lymphocytic lymphoma (SLL), follicular lymphoma (FL), diffuse large B-cell lymphoma (DLBCL), and marginal zone lymphoma (MZL).

47. The method of claim 39, wherein the BTK inhibitor is ibrutinib.

48. The method of claim 47, wherein the mutation encodes a substitution of aspartic acid to an amino acid selected from leucine, cysteine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 1140 of the PLCγ2 polypeptide.

49. The method of claim 48, wherein the mutation is a D1140G modification in the PLCγ2 polypeptide.

50. The method of claim 47, wherein the subject possesses high-risk cytogenetic features.

51. The method of claim 50, wherein the high-risk cytogenetic features comprise del(11q22.3), del(17p13.1) or complex karyotype.

52. The method of claim 47, wherein the hematologic cancer is a B-cell malignancy.

53. The method of claim 52, wherein the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit diffuse large B-cell lymphoma (DH-DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

54. The method of claim 53, wherein the cancer is a B-cell malignancy selected from the group consisting of mantle cell lymphoma (MCL), chronic lymphocytic leukemia (CLL), Waldenström macroglobulinemia (WM), small lymphocytic lymphoma (SLL), follicular lymphoma (FL), diffuse large B-cell lymphoma (DLBCL), and marginal zone lymphoma (MZL).

55. A system of detecting a modified PLCγ2 that confers resistance to inhibition with an irreversible BTK inhibitor in a subject, comprising:
   a. a sample containing a nucleic acid molecule encoding a PLCγ2 polypeptide from a subject with a hematologic cancer; and
   b. a microarray comprising nucleic acid encoding a modified PLCγ2 polypeptide or a portion thereof that is modified at an amino acid position corresponding to amino acid position 1140 of the amino acid sequence set forth in SEQ ID NO:2.

56. The system of claim 55, wherein the microarray further comprises nucleic acid encoding a modified PLCγ2 polypeptide or a portion thereof that is modified at additional amino acid positions.

* * * * *

UNITED STATES PATENT AND TRADEMARK OFFICE
CERTIFICATE OF CORRECTION

PATENT NO. : 9,885,086 B2
APPLICATION NO. : 14/664663
DATED : February 6, 2018
INVENTOR(S) : John C. Bryd et al.

It is certified that error appears in the above-identified patent and that said Letters Patent is hereby corrected as shown below:

In the Claims

In Column 85, Claim 11, Line 3, "nucleic acid position 2713" should appear as follows:
--nucleic acid position 2535--

Signed and Sealed this
Second Day of April, 2019

Andrei Iancu
*Director of the United States Patent and Trademark Office*